United States Patent
Wong

(10) Patent No.: US 11,660,297 B2
(45) Date of Patent: May 30, 2023

(54) ANTIPROLIFERATIVE COMPOUNDS AND SECOND ACTIVE AGENTS FOR COMBINED USE

(71) Applicant: Celgene Corporation, Summit, NJ (US)

(72) Inventor: Lilly L. Wong, Solana Beach, CA (US)

(73) Assignee: Celgene Corporation, Summit, NJ (US)

( * ) Notice: Subject to any disclaimer, the term of this patent is extended or adjusted under 35 U.S.C. 154(b) by 38 days.

(21) Appl. No.: 16/737,710

(22) Filed: Jan. 8, 2020

(65) Prior Publication Data

US 2020/0215060 A1    Jul. 9, 2020

Related U.S. Application Data

(60) Provisional application No. 62/790,326, filed on Jan. 9, 2019.

(51) Int. Cl.

| | | |
|---|---|---|
| *A61K 31/496* | (2006.01) | |
| *A61P 35/00* | (2006.01) | |
| *A61K 31/436* | (2006.01) | |
| *A61K 31/444* | (2006.01) | |
| *A61K 31/454* | (2006.01) | |
| *A61K 31/497* | (2006.01) | |
| *A61K 31/4985* | (2006.01) | |
| *A61K 31/5025* | (2006.01) | |
| *A61K 31/506* | (2006.01) | |
| *A61K 31/517* | (2006.01) | |
| *A61K 31/519* | (2006.01) | |
| *A61K 31/52* | (2006.01) | |
| *A61K 31/551* | (2006.01) | |
| *A61K 31/573* | (2006.01) | |
| *A61K 31/69* | (2006.01) | |
| *A61K 31/706* | (2006.01) | |
| *A61K 45/06* | (2006.01) | |

(52) U.S. Cl.
CPC ......... *A61K 31/496* (2013.01); *A61K 31/436* (2013.01); *A61K 31/444* (2013.01); *A61K 31/454* (2013.01); *A61K 31/497* (2013.01); *A61K 31/4985* (2013.01); *A61K 31/506* (2013.01); *A61K 31/5025* (2013.01); *A61K 31/517* (2013.01); *A61K 31/519* (2013.01); *A61K 31/52* (2013.01); *A61K 31/551* (2013.01); *A61K 31/573* (2013.01); *A61K 31/69* (2013.01); *A61K 31/706* (2013.01); *A61K 45/06* (2013.01); *A61P 35/00* (2018.01)

(58) Field of Classification Search
CPC .... A61K 31/496; A61K 35/00; A61K 31/519; A61K 31/4985; A61K 31/436; A61K 31/444; A61K 31/454; A61K 31/5025; A61K 31/497; A61K 31/52; A61K 31/551; A61K 31/517; A61K 31/506; A61K 31/706; A61K 31/573; A61K 31/69; A61K 45/06

See application file for complete search history.

(56) References Cited

U.S. PATENT DOCUMENTS 10,357,489 B2 *  7/2019  Alexander .............. A61P 35/02
11,185,543 B2 * 11/2021  Alexander .............. A61K 38/05

FOREIGN PATENT DOCUMENTS

WO    WO 2019/006299 A1    1/2019
WO    WO 2019/014100 A1    1/2019

OTHER PUBLICATIONS

ClinicalTrials.gov Identifier: NCT03374085, https://clinicaltrials.gov/ct2/show/NCT03374085, First Posted: Dec. 15, 2017 (Year: 2017).*
Rushworth et al. BTK inhibitor ibrutinib is cytotoxic to myeloma and potently enhances bortezomib and lenalidomide activities through NF-κB. Cellular Signalling 25 (2013) 106-112. (Year: 2013).*
Mezigdomide (CC-92480) | Cereblon E3 Ubiquitin Ligase Modulating Agent | MedChemExpress. https://www.medchemexpress.com/cc-92480.html (accessed on Dec. 8, 2021) (Year: 2021).*
Yu et al. Proteasome-dependent autoregulation of Bruton tyrosine kinase (Btk) promoter via NF-κB. Blood. 2008;111: 4617-4626. (Year: 2008).*
Anonymous, "History of changes for study NCT03374085 a safety, PK and efficacy study of CC-92480 in combination with dexamethasone in subjects with relapsed and refractory multiple myeloma," ClinicalTrials.gov Aug. 23, 2018, pp. 1-6, retrieved from the internet: URL:https://www.clinicaltrials.gov/ct2/history/NCT03374085?V_11=View#StudyPageTop.
Anonymous, "Welcome to the R&D deep dive series multiple myeloma changing the course of human health through bold pursuits in science," Mar. 24, 2018, pp. 1-108, retrieved from the Internet: URL:https://s24.q4cdn.com/483522778/files/doc_presentations/MM_Deep_Dive_FINAL_DECK_PRINT_PDF.pdf.
Hansen et al., "Discovery of CRBN E3 ligase modulator CC-92480 for the treatment of relapsed and refractory multiple myeloma," *J. Med. Chem.*, 63(13):6648-6676 (2020), retrieved from the Internet: https://dk.doi.org/10.1021/acs.jmedchem.9b01928.
Nooka et al., "Mechanism of action and novel IMiD-based compounds and combinations in multiple myeloma," *Cancer J.*, 25(1):19-31 (2019).

* cited by examiner

*Primary Examiner* — Yih-Horng Shiao
(74) *Attorney, Agent, or Firm* — Jones Day

(57) ABSTRACT

Provided herein are methods of using 4-(4-(4-(((2-(2,6-dioxopiperidin-3-yl)-1-oxoisoindolin-4-yl)oxy)methyl)benzyl)piperazin-1-yl)-3-fluorobenzonitrile, or an enantiomer, a mixture of enantiomers, a tautomer, or a pharmaceutically acceptable salt thereof, in combination with a second active agent for treating, preventing or managing multiple myeloma. The second active agent is one or more of a BTK inhibitor, an mTOR inhibitor, a PIM inhibitor, an IGF-1R inhibitor, an MEK inhibitor, an XPO1 inhibitor, a DOT1L inhibitor, an EZH2 inhibitor, a JAK2 inhibitor, a BRD4 inhibitor, a PLK 1 inhibitor, an NEK2 inhibitor, an AURKB inhibitor, a BIRC5 inhibitor, a BET inhibitor, or a DNA methyltransferase inhibitor.

19 Claims, 24 Drawing Sheets

ANTIPROLIFERATIVE COMPOUNDS AND SECOND ACTIVE AGENTS FOR COMBINED USE

Figure 1:
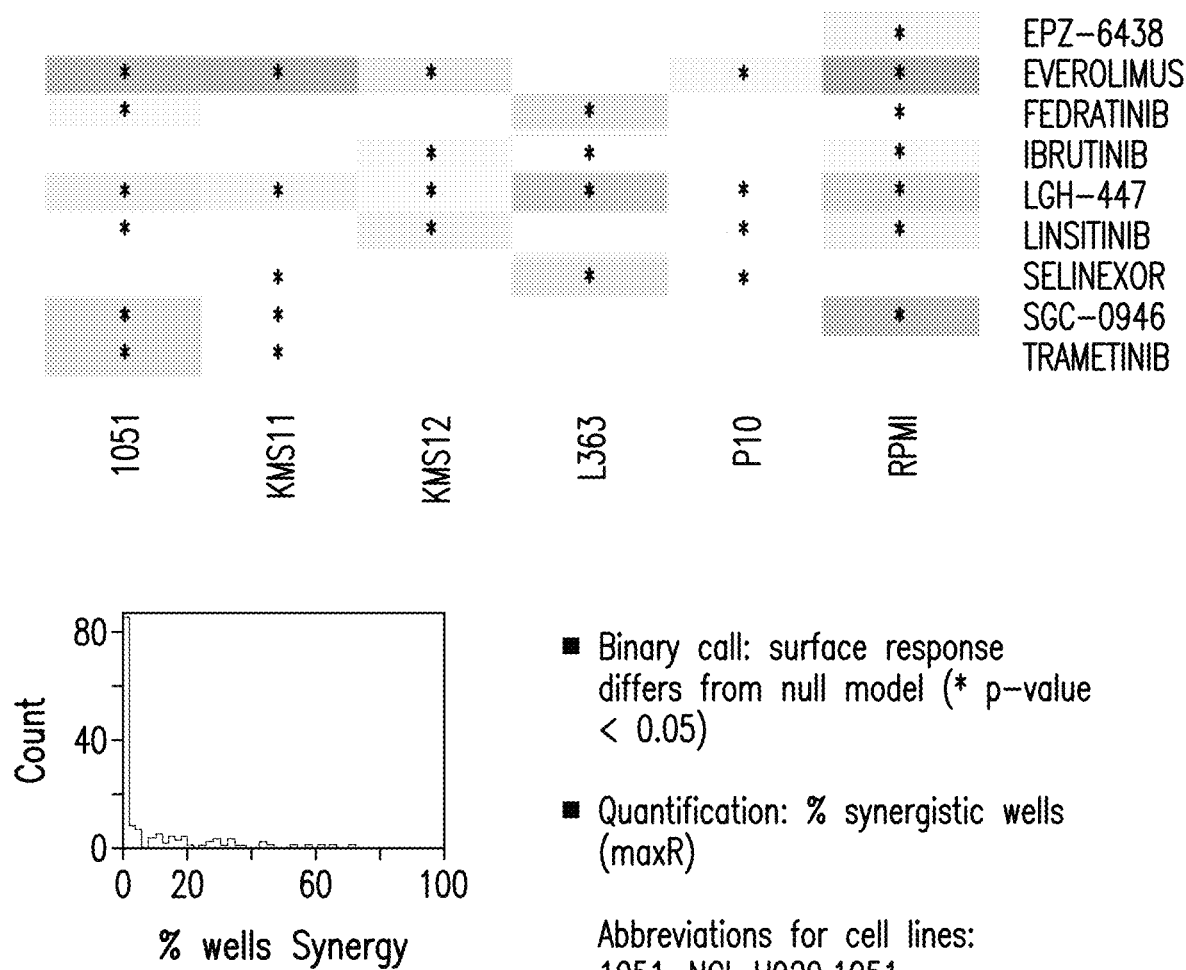

This application claims the benefit of U.S. Provisional Application No. 62/790,326, filed on Jan. 9, 2019, which is incorporated herein by reference in its entirety.

1. FIELD

Provided herein are methods of using 4-(4-(4-(((2-(2,6-dioxopiperidin-3-yl)-1-oxoisoindolin-4-yl)oxy)methyl)benzyl)piperazin-1-yl)-3-fluorobenzonitrile, or an enantiomer, a mixture of enantiomers, a tautomer, or a pharmaceutically acceptable salt thereof, in combination with a second active agent for treating, preventing or managing multiple myeloma.

2. BACKGROUND

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications. Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin, except in some patients (estimated at 1% to 5%) whose myeloma cells do not secrete these proteins (termed non-secretory myeloma). M-protein, short for monoclonal protein, also known as paraprotein, is a particularly abnormal protein produced by the myeloma plasma cells and can be found in the blood or urine of almost all patients with multiple myeloma, except for patients who have non-secretory myeloma or whose myeloma cells produce immunoglobulin light chains with heavy chain.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Current multiple myeloma therapy may involve one or more of surgery, stem cell transplantation, chemotherapy, immune therapy, and/or radiation treatment to eradicate multiple myeloma cells in a patient. All of the current therapy approaches pose significant drawbacks for the patient.

In the last decade, novel therapeutic agents, in particular immunomodulatory drugs such as lenalidomide and pomalidomide, significantly increased the response rates and prolonged progression free survival (PFS) and overall survival (OS) in multiple myeloma patients. However, persistent levels of residual disease that are below the sensitivity of bone marrow (BM) morphology, protein electrophoresis with immunofixation, and light chain quantitation exists in many patients with multiple myeloma, even after these patients have achieved complete response (CR), and will eventually cause relapse of the disease. Minimal residual disease (MRD) in myeloma is an independent predictor of progression-free survival (PFS) and is under consideration as a surrogate trial endpoint to improve the identification of effective treatments, particularly for frontline trials, which now require 5 to 10 years of follow-up to identify survival differences. Monitoring minimal residual disease (MRD) in patients with multiple myeloma thus provides prognostic value in predicting PFS and OS and making treatment decisions. The detection of minimal residual disease (MRD) in myeloma can use a 0.01% threshold ($10^{-4}$) after treatment, i.e., having $10^{-4}$ cells or fewer multiple myeloma cells as a proportion of total bone marrow mononuclear cells is considered MRD-negative, and having $10^{-4}$ cells or higher MRD-positive. The $10^{-4}$ MRD threshold was originally based on technical capability, but quantitative MRD detection is now possible at $10^{-5}$ by flow cytometry and $10^{-6}$ by high-throughput sequencing. (Rawstron et al., *Blood* 2015; 125(12): 1932-1935). Methods for measuring MRD include DNA sequencing of VDJ, polymerase chain reaction (PCR) (including allele specific PCR, ASO PCR) and multiparameter flow cytometry (MPF). Assays for MRD, e.g., based on clonotype profile measurement are also described in U.S. Pat. No. 8,628,927, to Faham et al., which is incorporated herein by reference.

There exists a significant need for safe and effective compounds and methods for treating, preventing and managing multiple myeloma, including for patients whose multiple myeloma is newly diagnosed or refractory to standard treatments, while reducing or avoiding the toxicities and/or side effects associated with the conventional therapies.

Citation or identification of any reference in Section 2 of this application is not to be construed as an admission that the reference is prior art to the present application.

3. SUMMARY

Provided herein are methods of using a compound of 4-(4-(4-(((2-(2,6-dioxopiperidin-3-yl)-1-oxoisoindolin-4-yl)oxy)methyl)benzyl)piperazin-1-yl)-3-fluorobenzonitrile, or an enantiomer, a mixture of enantiomers, a tautomer, or a pharmaceutically acceptable salt thereof, in combination with a second active agent for treating, preventing or managing multiple myeloma, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine).

Also provided for use in the methods provided herein are pharmaceutical compositions formulated for administration by an appropriate route and means containing effective concentrations of the compounds provided herein, for example, Compound 1, Compound 2 or Compound 3, or an enantiomer, mixture of enantiomers, tautomer, isotopolog, or pharmaceutically acceptable salt thereof, and optionally comprising at least one pharmaceutical carrier. Also provided for use in the methods provided herein are pharmaceutical compositions formulated for administration by an appropriate route and means containing effective concentrations of the second active agents provided herein, for example, ibrutinib, everolimus, LGH-447, linsitinib, trametinib, trametinib dimethyl sulfoxide, selinexor, SGC0946, pinometostat, tazemetostat, UNC1999, CPI-1205, fedratinib, JQ1, BI2536, JH295, barasertib, AZD1152-HQPA, YM155, Compound C, or azacitidine, or a stereoisomer, mixture of stereoisomers, tautomer, isotopolog, or pharmaceutically acceptable salt thereof.

In one embodiment, the pharmaceutical compositions deliver amounts effective for the treatment of multiple myeloma. In one embodiment, the pharmaceutical compositions deliver amounts effective for the prevention of multiple myeloma. In one embodiment, the pharmaceutical compositions deliver amounts effective for the amelioration of multiple myeloma.

Also provided herein are combination therapies using the compounds or compositions provided herein, or an enantiomer, mixture of enantiomers, tautomer, isotopolog, or pharmaceutically acceptable salt thereof, and a second active agent provided herein (e.g., ibrutinib, everolimus, LGH-447, linsitinib, trametinib, trametinib dimethyl sulfoxide, selinexor, SGC0946, pinometostat, tazemetostat, UNC1999, CPI-1205, fedratinib, JQ1, BI2536, JH295, barasertib, AZD1152-HQPA, YM155, Compound C, or azacitidine, or a stereoisomer, mixture of stereoisomers, tautomer, isotopolog, or pharmaceutically acceptable salt thereof), in further combination (e.g., a triple therapy) with a therapy, e.g., another pharmaceutical agent with activity against multiple myeloma or its symptoms. Examples of therapies within the scope of the methods include, but are not limited to, surgery, chemotherapy, radiation therapy, biological therapy, stem cell transplantation, cell therapy, and combinations thereof.

The compounds or compositions provided herein, or pharmaceutically acceptable derivatives thereof, may be administered simultaneously with, prior to, or after administration of each other and one or more of the above therapies. Pharmaceutical compositions containing a compound provided herein and one or more of the above therapies are also provided.

In one embodiment of practicing the methods provided herein, effective amounts of the compounds or compositions containing therapeutically effective concentrations of the compounds are administered to an individual exhibiting the symptoms of multiple myeloma to be treated. The amounts are effective to ameliorate or eliminate one or more symptoms of multiple myeloma.

Further provided is a pharmaceutical pack or kit comprising one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like.

These and other aspects of the subject matter described herein will become evident upon reference to the following detailed description.

4. DETAILED DESCRIPTION OF THE INVENTION

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

"$IC_{50}$" refers to an amount, concentration or dosage of a particular test compound that achieves a 50% inhibition of a maximal response, such as receptor binding, receptor activity, cell growth or proliferation, measured via any of the in vitro or cell based assays described herein.

Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates, fumarates and organic sulfonates.

Unless specifically stated otherwise, where a compound may assume alternative tautomeric, regioisomeric and/or stereoisomeric forms, all alternative isomers are intended to be encompassed within the scope of the claimed subject matter. For example, where a compound can have one of two tautomeric forms, it is intended that both tautomers be encompassed herein.

Thus, the compounds provided herein may be enantiomerically pure, or be stereoisomeric or diastereomeric mixtures. As used herein and unless otherwise indicated, the term "stereoisomerically pure" means a composition that comprises one stereoisomer of a compound and is substantially free of other stereoisomers of that compound. For example, a stereoisomerically pure composition of a compound having one chiral center will be substantially free of the opposite enantiomer of the compound. A stereoisomerically pure composition of a compound having two chiral centers will be substantially free of other diastereomers of the compound. A typical stereoisomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. A stereoisomerically pure compound as used herein comprises greater than about 80% by weight of one stereoisomer of the compound, more preferably greater than about 90% by weight of one stereoisomer of the compound, even more preferably greater than about 95% by weight of one stereoisomer of the compound, and most preferably greater than about 97% by weight of one stereoisomer of the compound. As used herein and unless otherwise indicated, the term "stereoisomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereoisomerically pure composition of a compound having one chiral center. Similarly, the term "stereoisomerically enriched" means a stereoisomerically enriched composition of a compound having one chiral center. As used herein, stereoisomeric or diastereomeric mixtures means a composition that comprises more than one stereoisomer of a compound. A typical stereoisomeric mixture of a compound comprises about 50% by weight of one stereoisomer of the compound and about 50% by weight of other stereoisomers of the compound, or comprises greater than about 50% by weight of one stereoisomer of the compound and less than about 50% by weight of other stereoisomers of the compound, or comprises greater than about 45% by weight of one stereoisomer of the compound and less than about 55% by weight of the other stereoisomers of the compound, or comprises greater than about 40% by weight of one stereoisomer of the compound and less than about 60% by weight of the other stereoisomers of the compound, or comprises greater than about 35% by weight of one stereoisomer of the compound and less than about 65% by weight of the other stereoisomers of the compound.

It is to be understood that the compounds provided herein may contain chiral centers. Such chiral centers may be of either the (R) or (S) configuration, or may be a mixture thereof. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Optically active (+) and (−), (R)- and (S)-, or (D)- and (L)-isomers may be prepared using chiral synthons or chiral reagents, or resolved using conventional techniques, such as chromatography on a chiral stationary phase.

As used herein, an "isotopolog" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., multiple myeloma therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds, for example, the isotopologues of Compound 1, Compound 2 or Compound 3 are deuterium, carbon-13, or nitrogen-15 enriched compounds. In some embodiments, isotopologues provided herein are deuterium enriched compounds. In some embodiments, isotopologues provided herein are deuterium enriched compounds, where the deuteration occurs on the chiral center.

In the description herein, if there is any discrepancy between a chemical name and chemical structure, the structure controls.

As used herein "multiple myeloma" refers to hematological conditions characterized by malignant plasma cells and includes the following disorders: monoclonal gammopathy of undetermined significance (MGUS); low risk, intermediate risk, and high risk multiple myeloma; newly diagnosed multiple myeloma (including low risk, intermediate risk, and high risk newly diagnosed multiple myeloma); transplant eligible and transplant ineligible multiple myeloma; smoldering (indolent) multiple myeloma (including low risk, intermediate risk, and high risk smouldering multiple myeloma); active multiple myeloma; solitary plasmacytoma; extramedullary plasmacytoma; plasma cell leukemia; central nervous system multiple myeloma; light chain myeloma; non-secretory myeloma; Immunoglobulin D myeloma; and Immunoglobulin E myeloma; and multiple myeloma characterized by genetic abnormalities, such as Cyclin D translocations (for example, t(11;14)(q13;q32); t(6;14)(p21;32); t(12;14)(p13;q32); or t(6;20); MMSET translocations (for example, t(4; 14)(p16;q32)); MAF translocations (for example, t(14;16)(q32;q32); t(20;22); t(16; 22)(q11;q13); or t(14;20)(q32;q11)); or other chromosome factors (for example, deletion of 17p13, or chromosome 13; del(17/17p), nonhyperdiploidy, and gain(1q)). In one embodiment, the multiple myeloma is characterized according to the multiple myeloma International Staging System (ISS). In one embodiment, the multiple myeloma is Stage I multiple myeloma as characterized by ISS (e.g., serum β2 microglobulin <3.5 mg/L and serum albumin ≥3.5 g/dL). In one embodiment, the multiple myeloma is Stage III multiple myeloma as characterized by ISS (e.g., serum β2 microglobulin >5.4 mg/L). In one embodiment, the multiple myeloma is Stage II multiple myeloma as characterized by ISS (e.g., not Stage I or III).

As used herein and unless otherwise indicated, the terms "treat," "treating" and "treatment" refer to alleviating or reducing the severity of a symptom associated with the disease or condition being treated, for example, multiple myeloma.

The term "prevention" includes the inhibition of a symptom of the particular disease or disorder, for example multiple myeloma. In some embodiments, patients with familial history of multiple myeloma are candidates for preventive regimens. Generally, the term "preventing" refers to administration of the drug prior to the onset of symptoms, particularly to patients at risk of multiple myeloma.

As used herein and unless otherwise indicated, the term "managing" encompasses preventing the recurrence of the particular disease or disorder, such as multiple myeloma, in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein, "subject" or "patient" is an animal, typically a mammal, including a human, such as a human patient.

The term "relapsed" refers to a situation where patients who have had a remission of multiple myeloma after therapy have a return of myeloma cells and/or reduced normal cells in the marrow.

The term "refractory or resistant" refers to a circumstance where patients, even after intensive treatment, have residual myeloma cells and/or reduced normal cells in the marrow.

As used herein, "induction therapy" refers to the first treatment given for a disease, or the first treatment given with the intent of inducing complete remission in a disease, such as cancer. When used by itself, induction therapy is the one accepted as the best available treatment. If residual cancer is detected, patients are treated with another therapy, termed reinduction. If the patient is in complete remission after induction therapy, then additional consolidation and/or maintenance therapy is given to prolong remission or to potentially cure the patient.

As used herein, "consolidation therapy" refers to the treatment given for a disease after remission is first achieved. For example, consolidation therapy for cancer is the treatment given after the cancer has disappeared after initial therapy. Consolidation therapy may include radiation therapy, stem cell transplant, or treatment with cancer drug therapy. Consolidation therapy is also referred to as intensification therapy and post-remission therapy.

As used herein, "maintenance therapy" refers to the treatment given for a disease after remission or best response is achieved, in order to prevent or delay relapse. Maintenance therapy can include chemotherapy, hormone therapy or targeted therapy.

"Remission" as used herein, is a decrease in or disappearance of signs and symptoms of a cancer, for example, multiple myeloma. In partial remission, some, but not all, signs and symptoms of the cancer have disappeared. In complete remission, all signs and symptoms of the cancer have disappeared, although the cancer still may be in the body.

As used herein "transplant" refers to high-dose therapy with stem cell rescue. Hematopoietic (blood) or bone marrow stem cells are used not as treatment but to rescue the patient after the high-dose therapy, for example high dose chemotherapy and/or radiation. Transplant includes "autologous" stem cell transplant (ASCT), which refers to use of the patients' own stem cells being harvested and used as the replacement cells. In some embodiments, transplant also includes tandem transplant or multiple transplants.

As used herein, and unless otherwise specified, the terms "therapeutically effective amount" and "effective amount" of a compound refer to an amount sufficient to provide a therapeutic benefit in the treatment, prevention and/or management of a disease, for example multiple myeloma, or to delay or minimize one or more symptoms associated with the disease or disorder to be treated. The terms "therapeutically effective amount" and "effective amount" can encompass an amount that improves overall therapy, reduces or avoids symptoms or causes of disease or disorder, or enhances the therapeutic efficacy of another therapeutic agent.

The terms "co-administration" and "in combination with" include the administration of one or more therapeutic agents (for example, a compound provided herein and another anti-multiple myeloma agent, cancer agent or supportive care agent) either simultaneously, concurrently or sequentially with no specific time limits. In one embodiment, the agents are present in the cell or in the patient's body at the same time or exert their biological or therapeutic effect at the same time. In one embodiment, the therapeutic agents are in the same composition or unit dosage form. In another embodiment, the therapeutic agents are in separate compositions or unit dosage forms.

The term "supportive care agent" refers to any substance that treats, prevents or manages an adverse effect from treatment with Compound 1, Compound 2 or Compound 3, or an enantiomer or a mixture of enantiomers, tautomers, isotopolog or a pharmaceutically acceptable salt thereof.

The term "biological therapy" refers to administration of biological therapeutics such as cord blood, stem cells, growth factors and the like.

In the context of a cancer, such as multiple myeloma, inhibition may be assessed by inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP, as used herein, means the time from treatment onset until tumor progression; TTP does not include deaths. In one embodiment, PFS means the time from treatment onset until tumor progression or death. In one embodiment, PFS means the time from the first dose of compound to the first occurrence of disease progression or death from any cause. In one embodiment, PFS rates will be computed using the Kaplan-Meier estimates. Event-free survival (EFS) means the time from treatment onset until any treatment failure, including disease progression, treatment discontinuation for any reason, or death. In one embodiment, overall response rate (ORR) means the percentage of patients who achieve a response. In one embodiment, ORR means the sum of the percentage of patients who achieve complete and partial responses. In one embodiment, ORR means the percentage of patients whose best response ≥partial response (PR), according to the IMWG Uniform Response Criteria. In one embodiment, duration of response (DoR) is the time from achieving a response until relapse or disease progression. In one embodiment, DoR is the time from achieving a response ≥partial response (PR) until relapse or disease progression. In one embodiment, DoR is the time from the first documentation of a response until to the first documentation of progressive disease or death. In one embodiment, DoR is the time from the first documentation of a response ≥partial response (PR) until to the first documentation of progressive disease or death. In one embodiment, time to response (TTR) means the time from the first dose of compound to the first documentation of a response. In one embodiment, TTR means the time from the first dose of compound to the first documentation of a response ≥partial response (PR). In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of multiple myeloma may be assessed by the International Uniform Response Criteria for Multiple Myeloma (IURC) (see Durie B G M, Harousseau J-L, Miguel J S, et al. International uniform response criteria for multiple myeloma. *Leukemia*, 2006; (10) 10: 1-7), using the response and endpoint definitions shown below:

| Response Subcategory | Response Criteria[a] |
|---|---|
| sCR | CR as defined below plus Normal FLC ratio and Absence of clonal cells in bone marrow[b] by immunohistochemistry or immunofluorescence[c] |
| CR | Negative immunofixation on the serum and urine and Disappearance of any soft tissue plasmacytomas and <5% plasma cells in bone marrow[b] |
| VGPR | Serum and urine M-protein detectable by immunofixation but not on electrophoresis or 90% or greater reduction in serum M-protein plus urine M-protein level <100 mg per 24 h |
| PR | ≥50% reduction of serum M-protein and reduction in 24-h urinary M-protein by ≥90% or to <200 mg per 24 h<br>If the serum and urine M-protein are unmeasurable,[d] a ≥50% decrease in the difference between involved and uninvolved FLC levels is required in place of the M-protein criteria<br>If serum and urine M-protein are unmeasurable, and serum free light assay is also unmeasurable, ≥50% reduction in plasma cells is required in place of M-protein, provided baseline bone marrow plasma cell percentage was ≥30%<br>In addition to the above listed criteria, if present at baseline, a ≥50% reduction in the size of soft tissue plasmacytomas is also required |
| SD (not recommended for use as an indicator of response; stability of disease is best described by providing the time to progression estimates) | Not meeting criteria for CR, VGPR, PR or progressive disease |

Abbreviations:
CR, complete response; FLC, free light chain; PR, partial response; SD, stable disease; sCR, stringent complete response; VGPR, very good partial response.
[a]All response categories require two consecutive assessments made at any time before the institution of any new therapy; all categories also require no known evidence of progressive or new bone lesions if radiographic studies were performed. Radiographic studies are not required to satisfy these response requirements.
[b]Confirmation with repeat bone marrow biopsy not needed.
[c]Presence/absence of clonal cells is based upon the κ/λ ratio. An abnormal κ/λ ratio by immunohistochemistry and/or immunofluorescence requires a minimum of 100 plasma cells for analysis. An abnormal ratio reflecting presence of an abnormal clone is κ/λ of >4:1 or <1:2.
[d]Measurable disease defined by at least one of the following measurements: Bone marrow plasma cells ≥30%; Serum M-protein ≥1 g/dl (≥10 gm/l)[10 g/l]; Urine M-protein ≥200 mg/24 h; Serum FLC assay: Involved FLC level ≥10 mg/dl (≥100 mg/l); provided serum FLC ratio is abnormal.

As used herein, ECOG status refers to Eastern Cooperative Oncology Group (ECOG) Performance Status (Oken M, et al Toxicity and response criteria of the Eastern Cooperative Oncology Group. *Am J Clin Oncol* 1982; 5(6):649-655), as shown below:

| Score | Description |
|---|---|
| 0 | Fully active, able to carry on all pre-disease performance without restriction |
| 1 | Restricted in physically strenuous activity but ambulatory and able to carry out work of a light or sedentary nature, eg, light housework, office work. |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair |
| 5 | Dead |

The term "about," as used herein, unless otherwise indicated, refers to a value that is no more than 10% above or below the value being modified by the term. For example, the term "about 10 mg/m$^2$" means a range of from 9 mg/m$^2$ to 11 mg/m$^2$.

B. BRIEF DESCRIPTION OF THE FIGURES

FIG. 1 shows the effect of treatment of MM cells with Compound 2 in combination with 9 small molecule inhibitors. Synergy calculations were performed for treatment with Compound 2 in combination with 9 small molecule inhibitors across a panel of MM cell lines. The shade boxes illustrate the percentage of wells that show synergistic activity after combined treatment with Compound 2. The * represents the significance of the surface response difference from the null model.

Figure 2A:
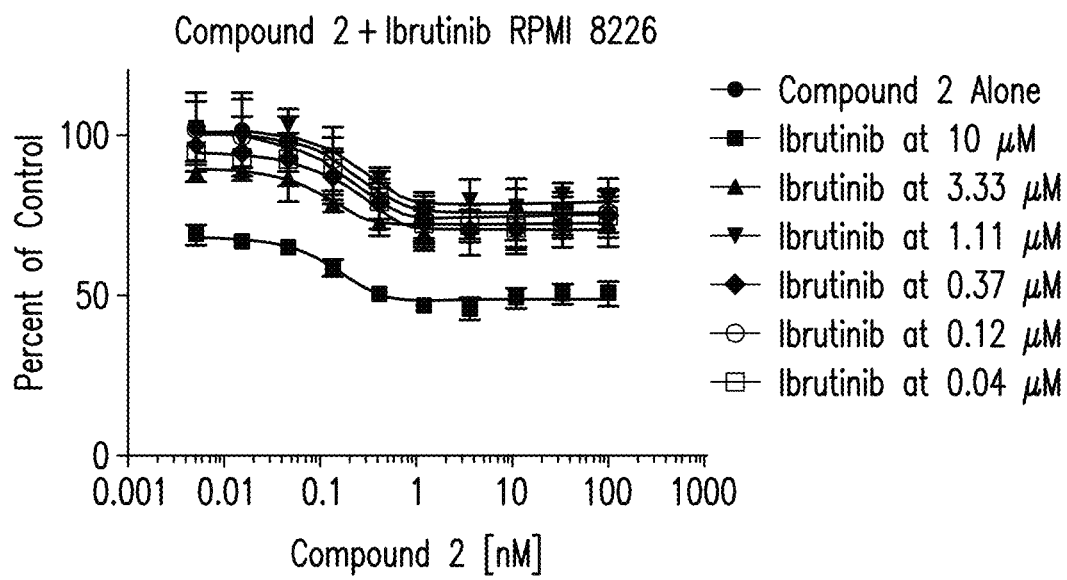
Figure 2B:
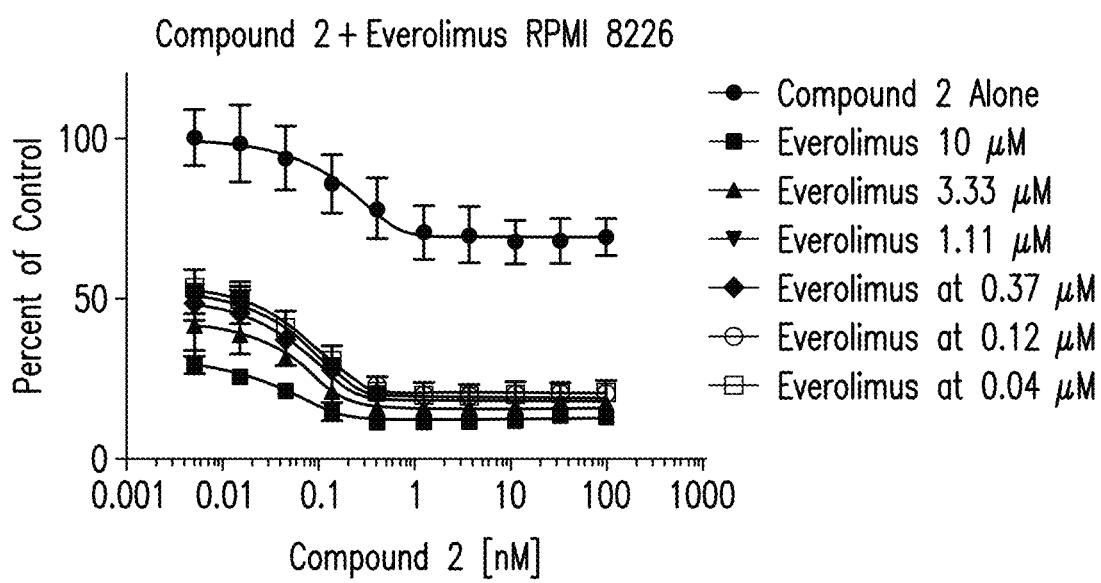
Figure 2C:
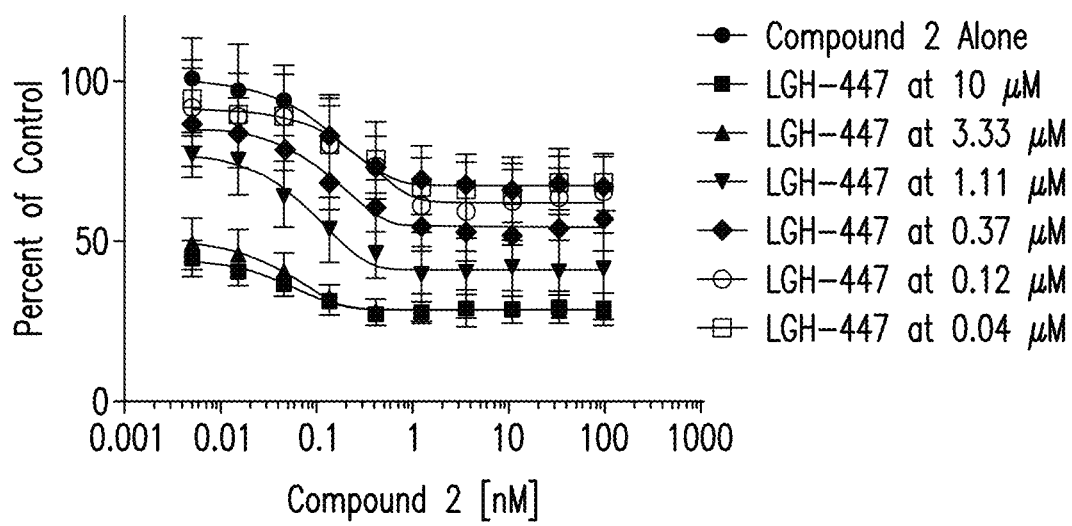
Figure 2D:
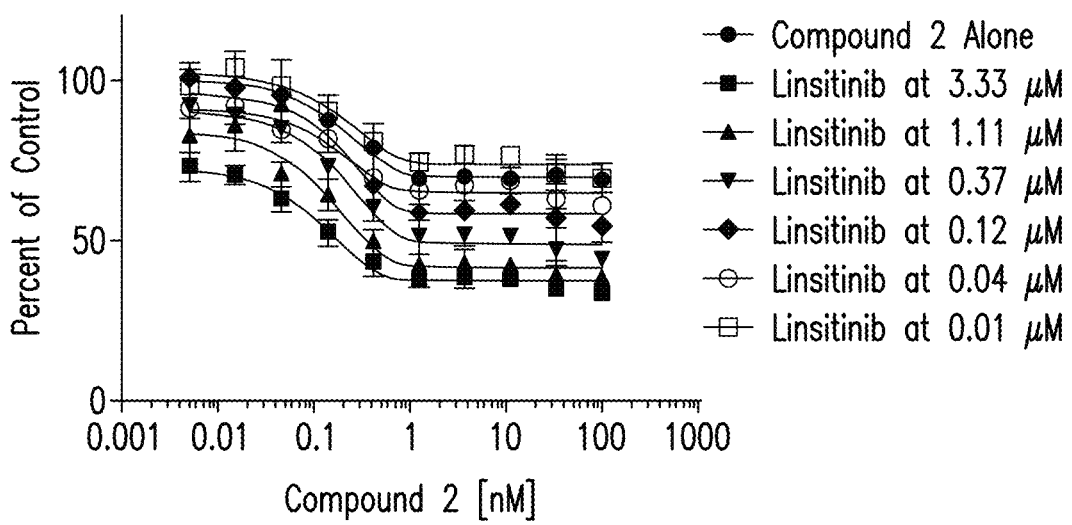
Figure 2E:
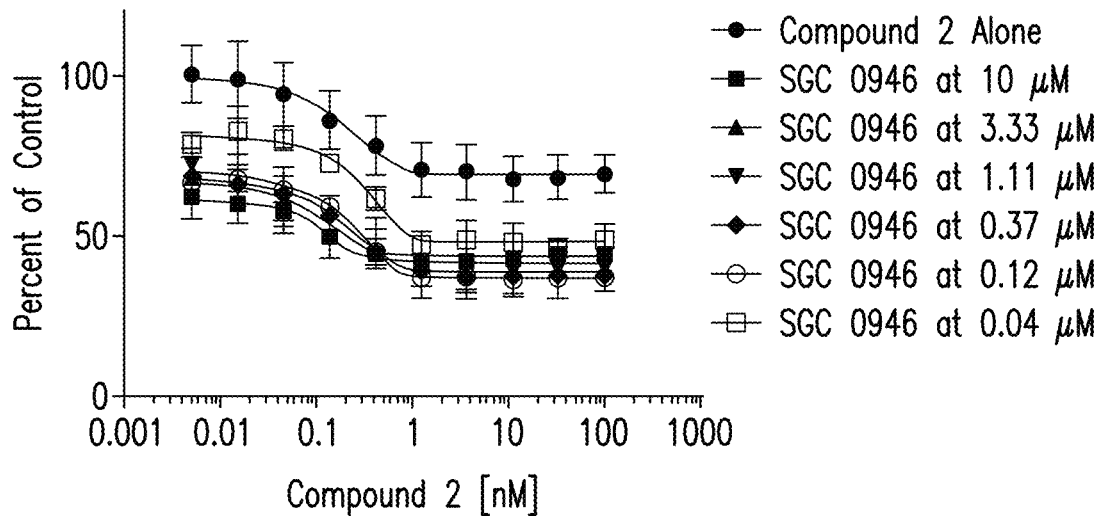
Figure 2F:
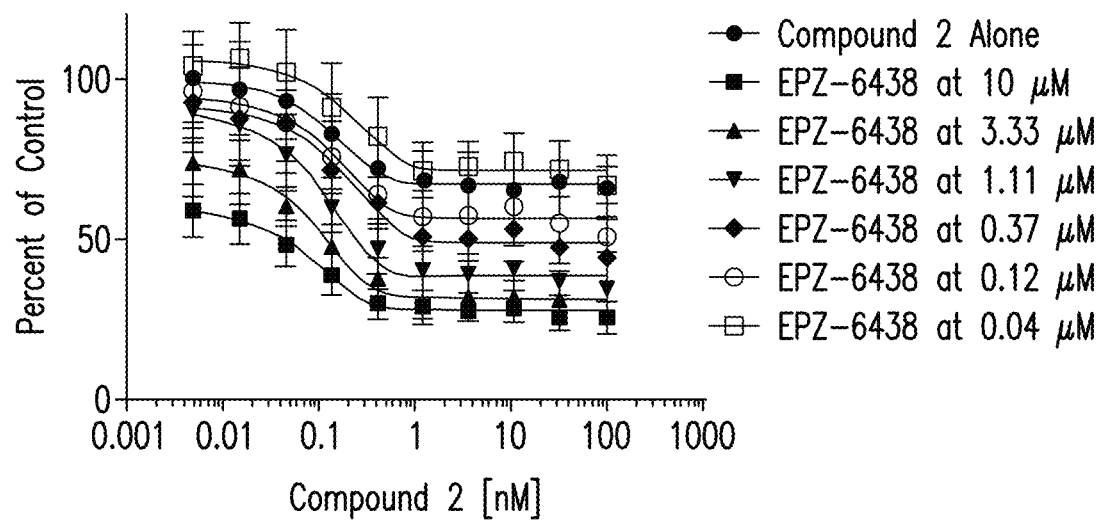
Figure 2G:
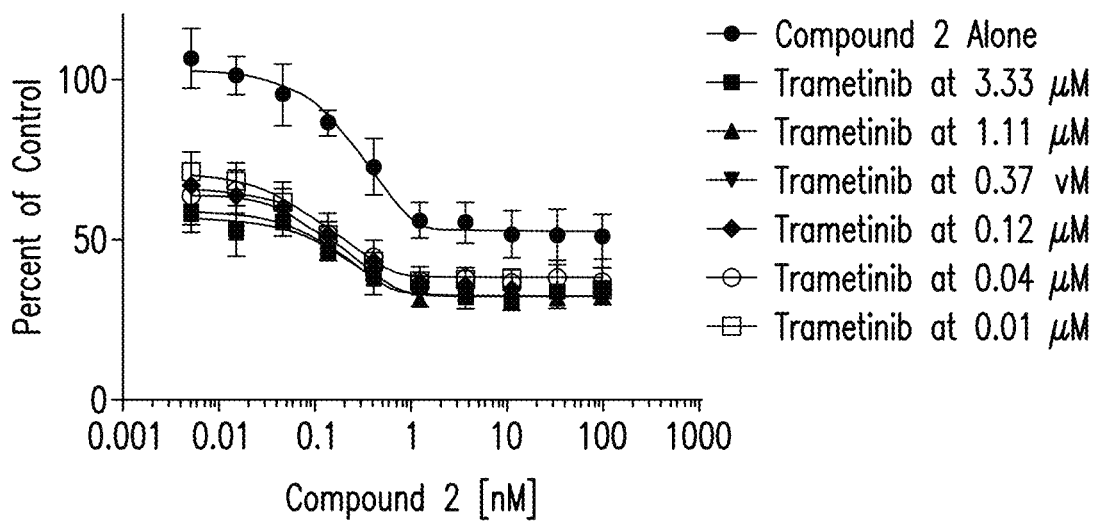
Figure 2H:
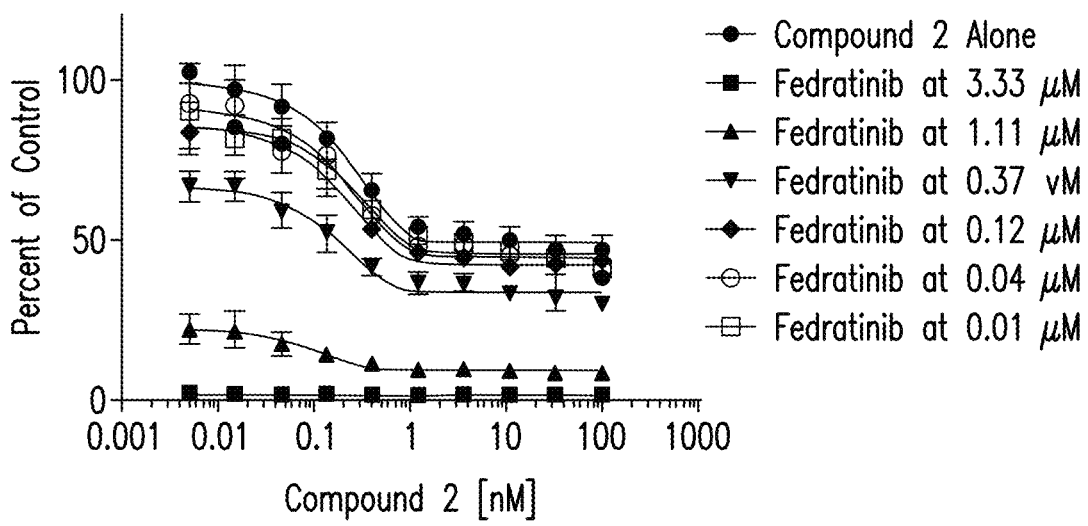
Figure 2I:
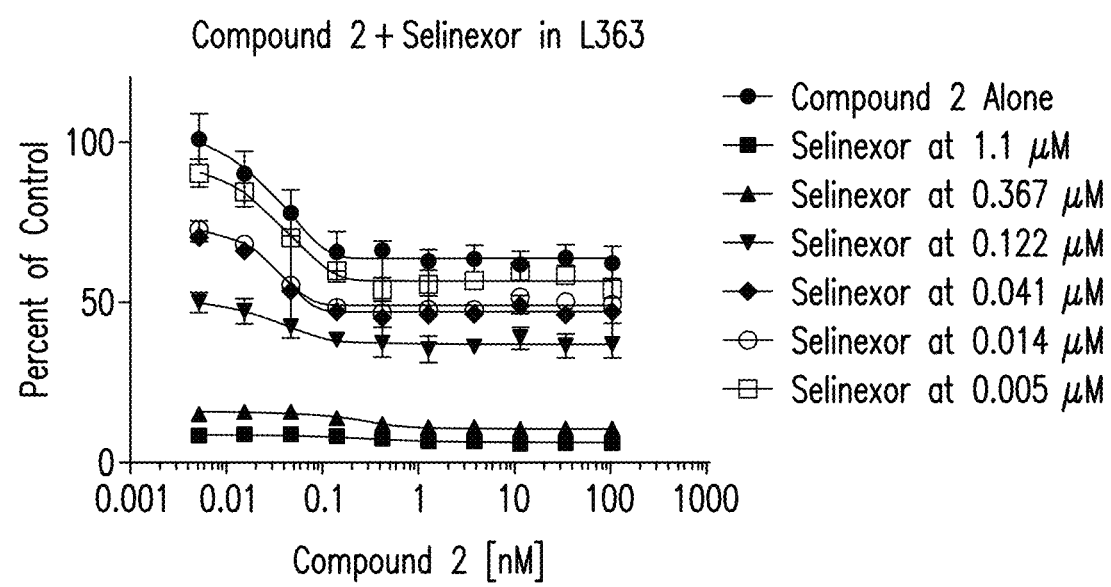

FIG. 2A shows the effect of treatment of RPMI MM cells with Compound 2 in combination with ibrutinib; FIG. 2B shows the effect of treatment of RPMI MM cells with Compound 2 in combination with everolimus; FIG. 2C shows the effect of treatment of RPMI MM cells with Compound 2 in combination with LGH-447; FIG. 2D shows the effect of treatment of RPMI MM cells with Compound 2 in combination with linsitinib; FIG. 2E shows the effect of treatment of RPMI MM cells with Compound 2 in combination with SGC0946; FIG. 2F shows the effect of treatment of RPMI MM cells with Compound 2 in combination with EPZ-6438; FIG. 2G shows the effect of treatment of H929 MM cells with Compound 2 in combination with trametinib; FIG. 2H shows the effect of treatment of H929 MM cells with Compound 2 in combination with fedratinib; and FIG. 2I shows the effect of treatment of L363 MM cells with Compound 2 in combination with selinexor.

Figure 3B:
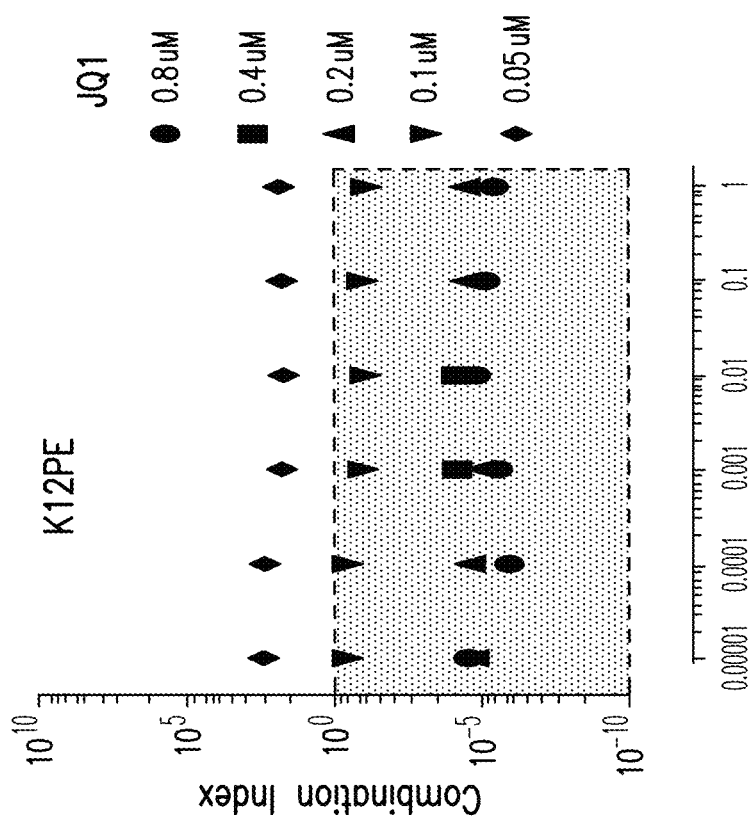
Figure 3A:
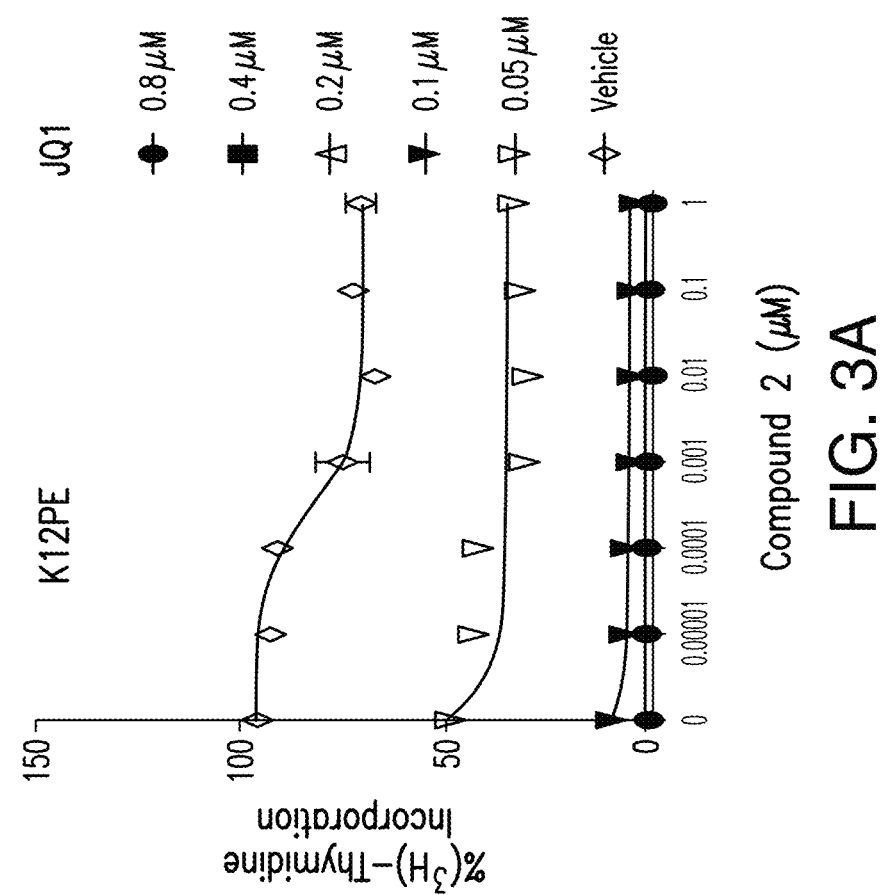
Figures 3C, 3D:
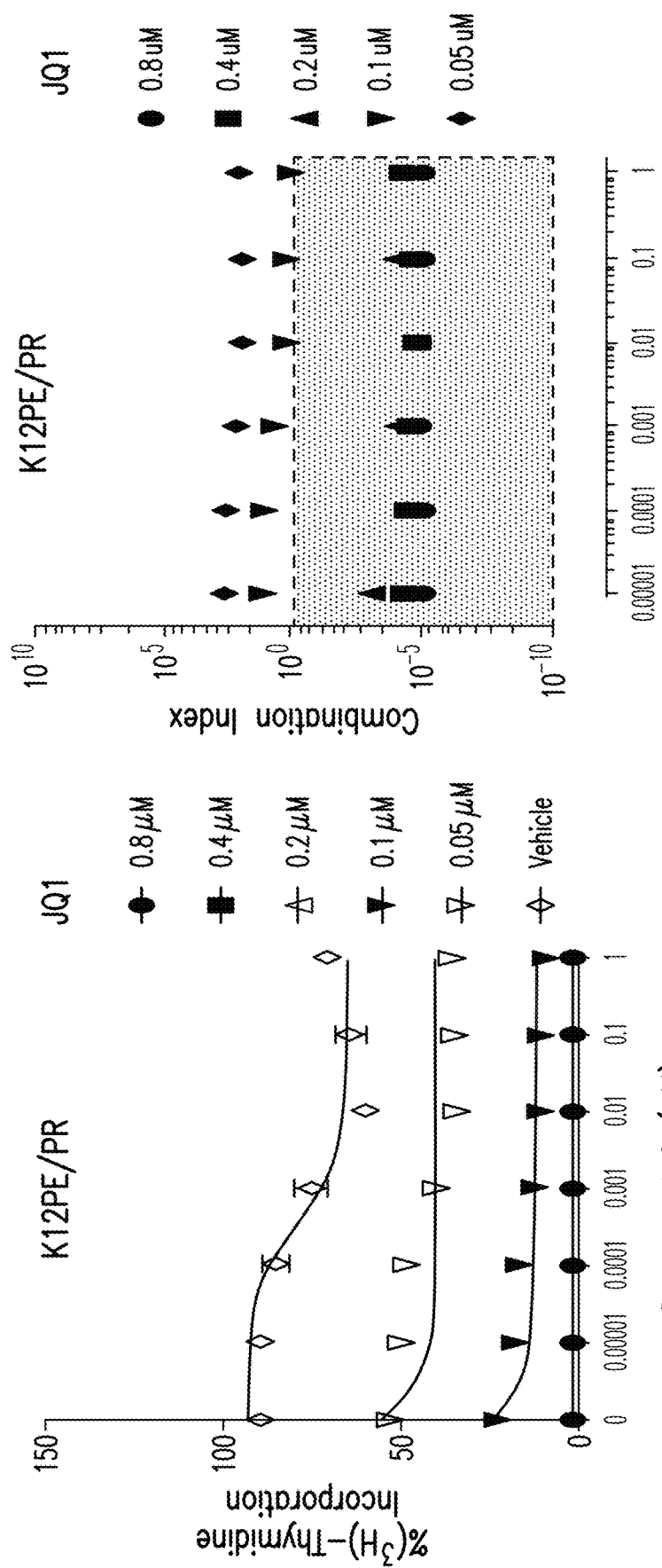

FIG. 3A shows the effect of treatment of K12PE cell lines with Compound 2 in combination with JQ1; FIG. 3B shows the corresponding combination index values; FIG. 3C shows the effect of treatment of K12PE-PR cell lines with Compound 2 in combination with JQ1; and FIG. 3D shows the corresponding combination index values.

Figure 4B:
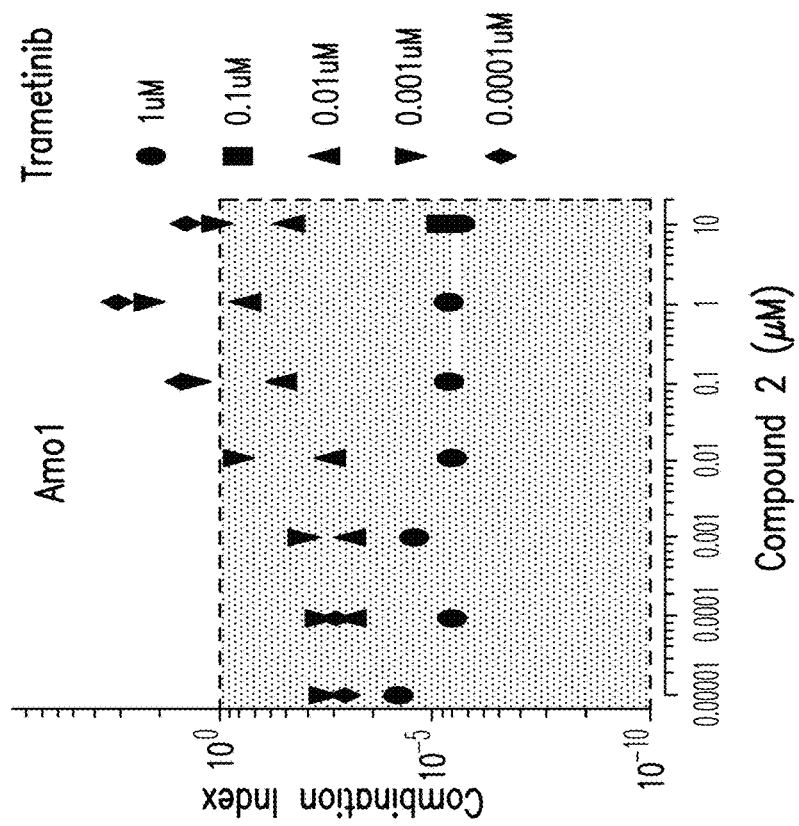
Figure 4A:
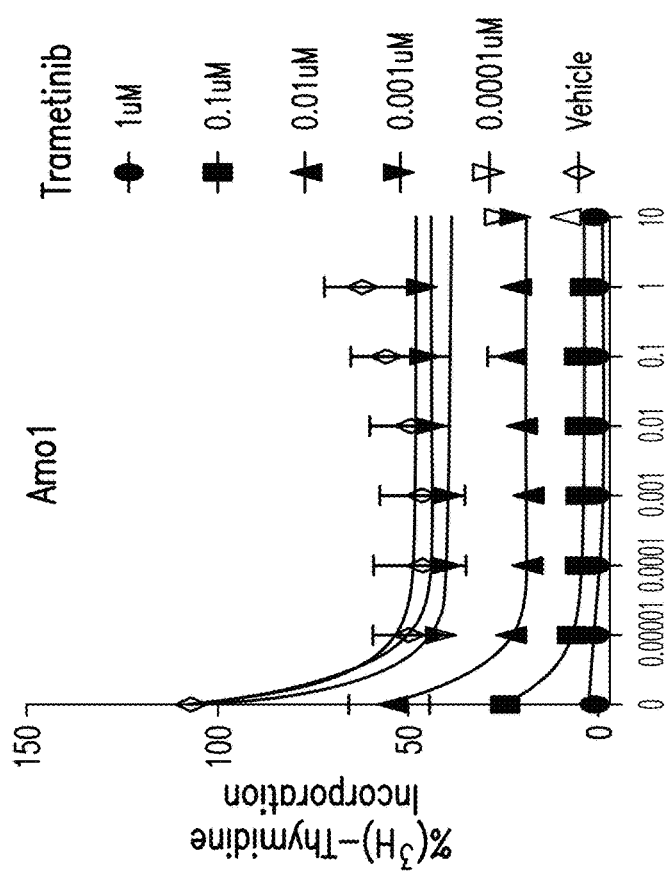
Figure 4D:
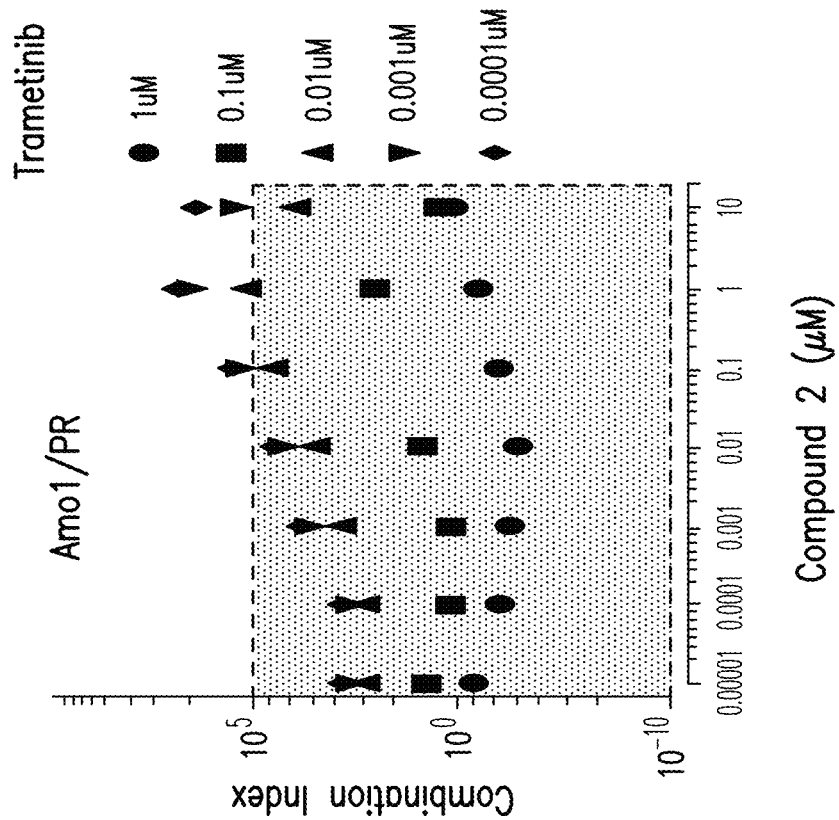
Figure 4C:
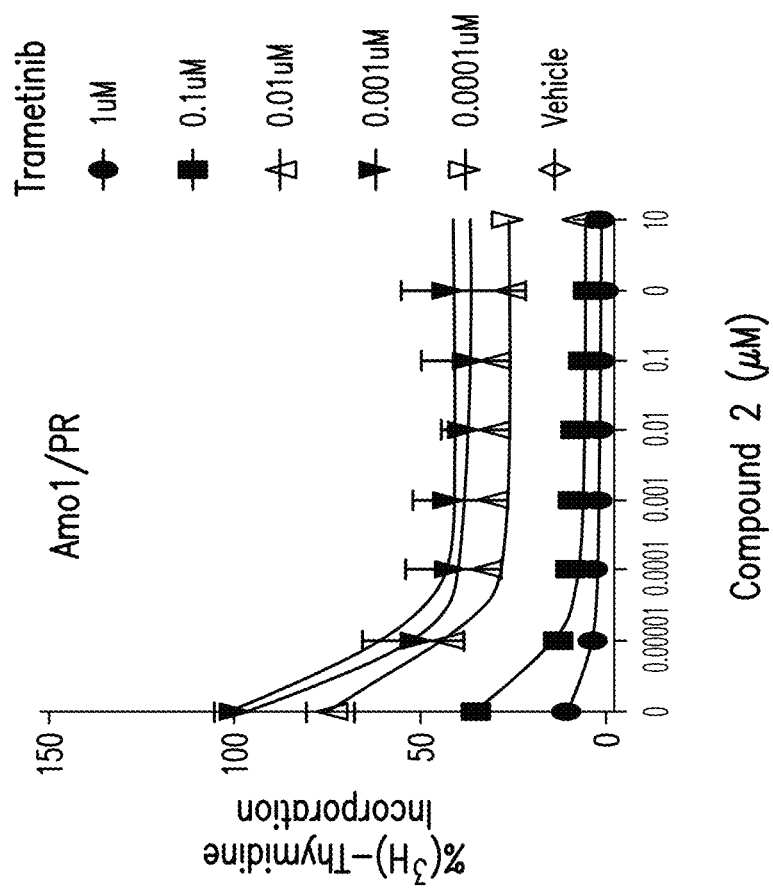

FIG. 4A shows treatment of AMO1 cell lines with Compound 2 in combination with trametinib; FIG. 4B shows the corresponding combination index values; FIG. 4C shows the effect of treatment of AMO1-PR cell lines with Compound 2 in combination with trametinib; and FIG. 4D shows the corresponding combination index values.

Figure 5B:
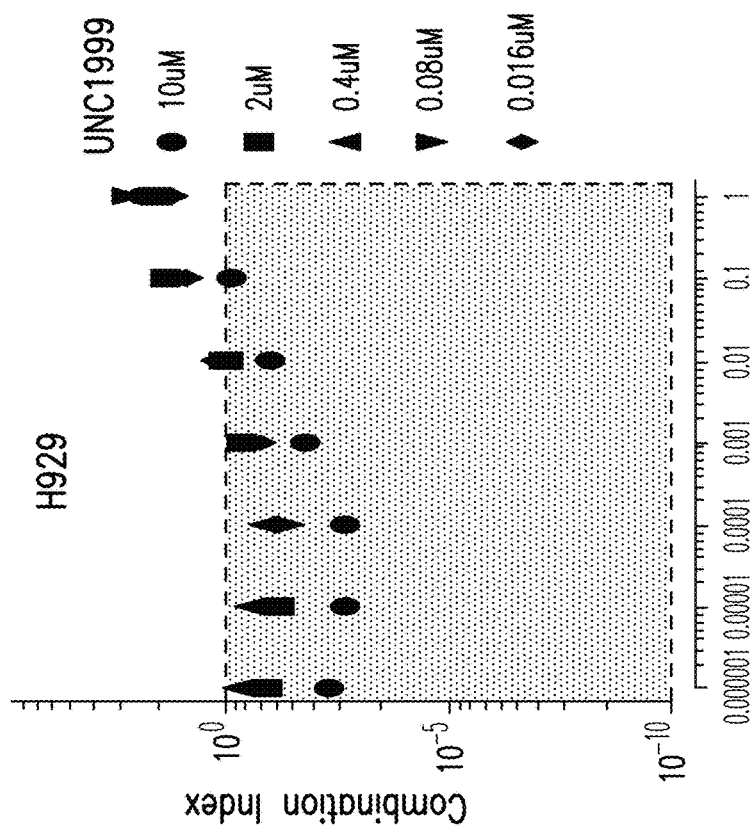
Figure 5A:
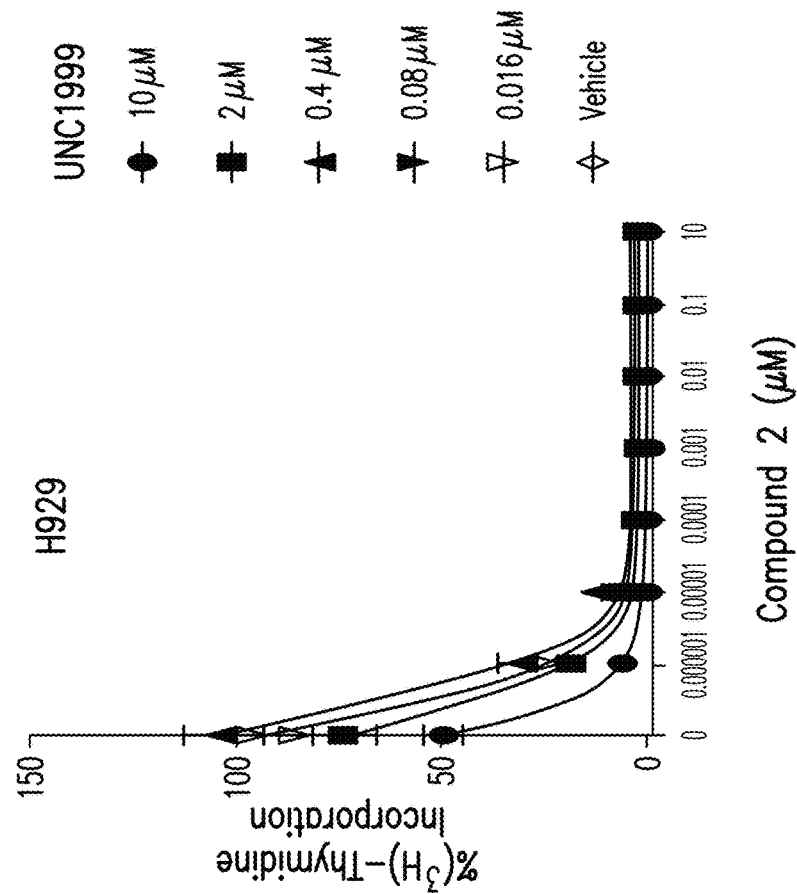

FIG. 5A shows the effect of treatment of H929 cell lines with Compound 2 in combination with UNC1999; and FIG. 5B shows the corresponding combination index values.

Figures 6A, 6B:
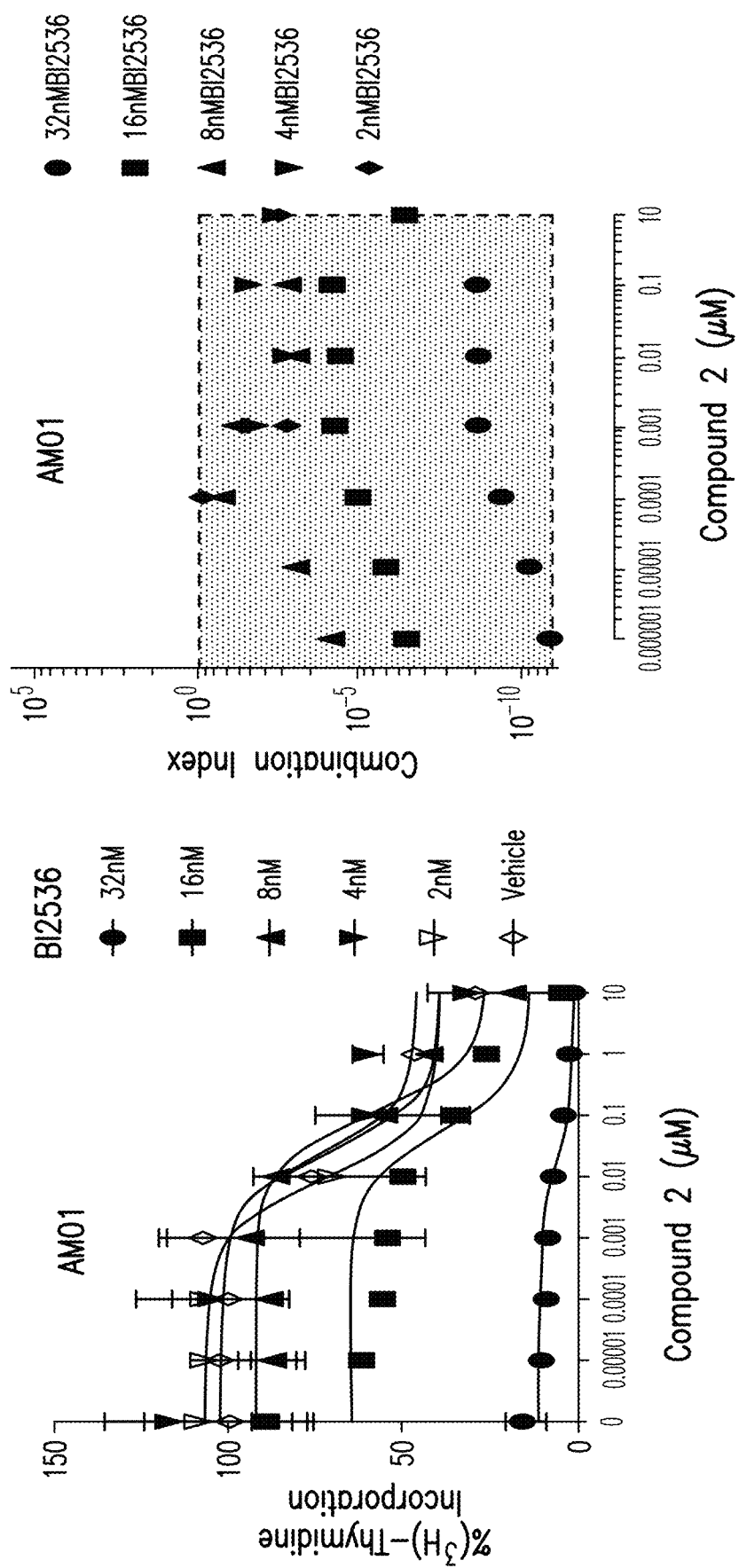
Figures 6C, 6D:
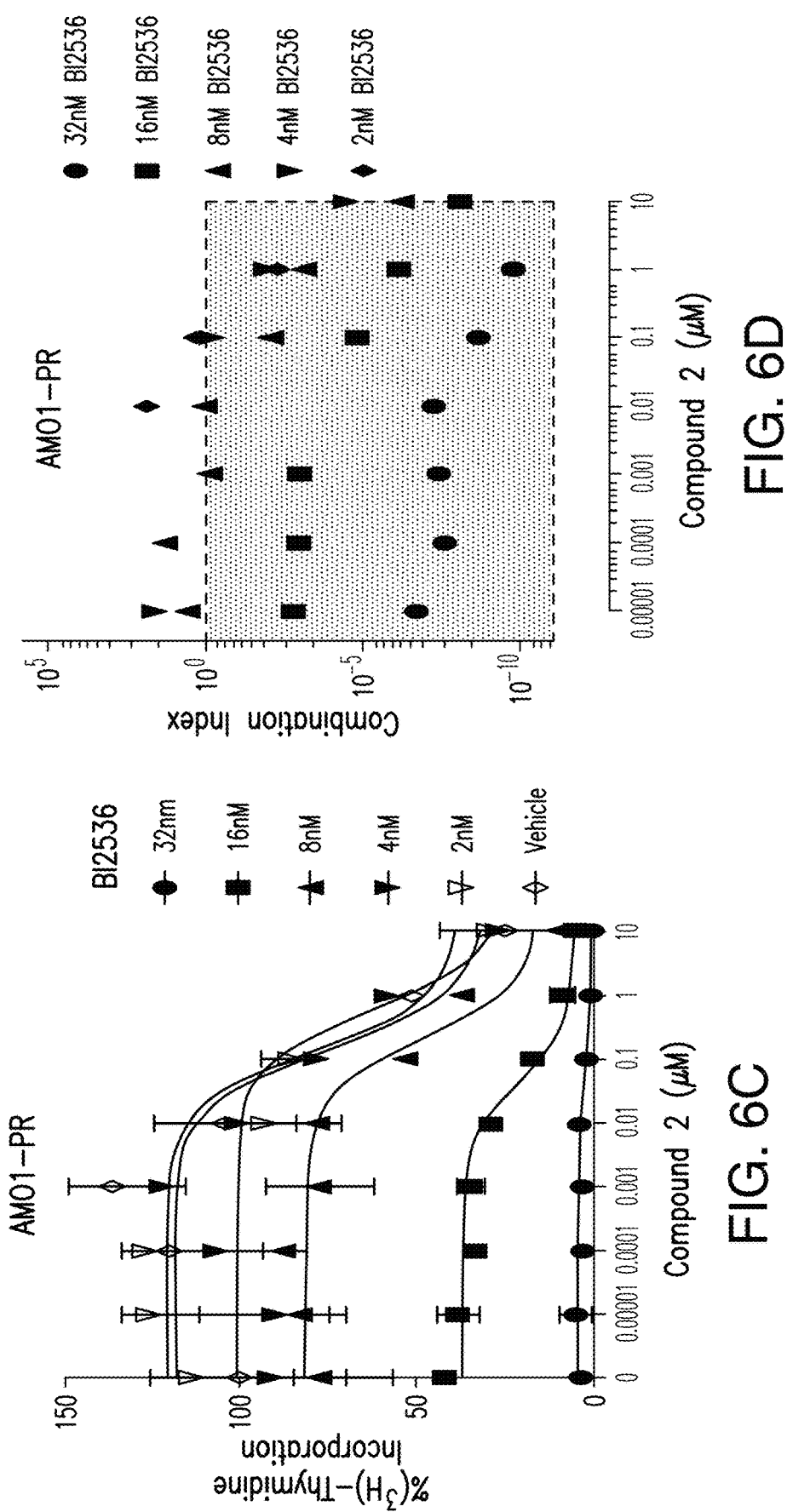

FIG. 6A shows the effect of treatment of AMO1 cell lines with Compound 2 in combination with B12536; FIG. 6B shows the corresponding combination index values; FIG. 6C shows the effect of treatment of AMO1-PR cell lines with Compound 2 in combination with B12536; and FIG. 6D shows the corresponding combination index values.

Figures 7A, 7B:
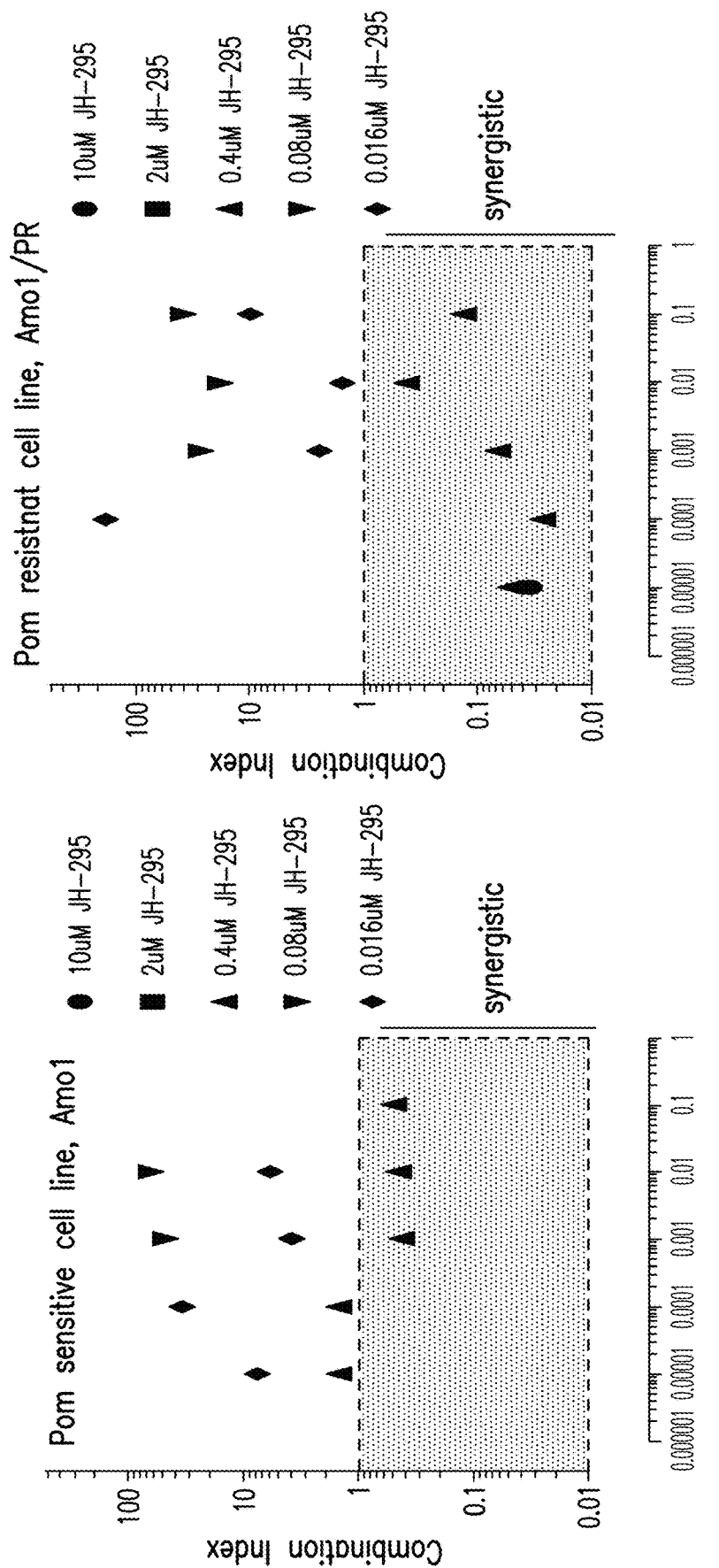

FIG. 7A shows the combination index for treatment of AMO1 cell lines with Compound 2 in combination with JH295; and FIG. 7B shows the combination index for treatment of AMO1-PR cell lines with Compound 2 in combination with JH295.

Figures 8A, 8B:
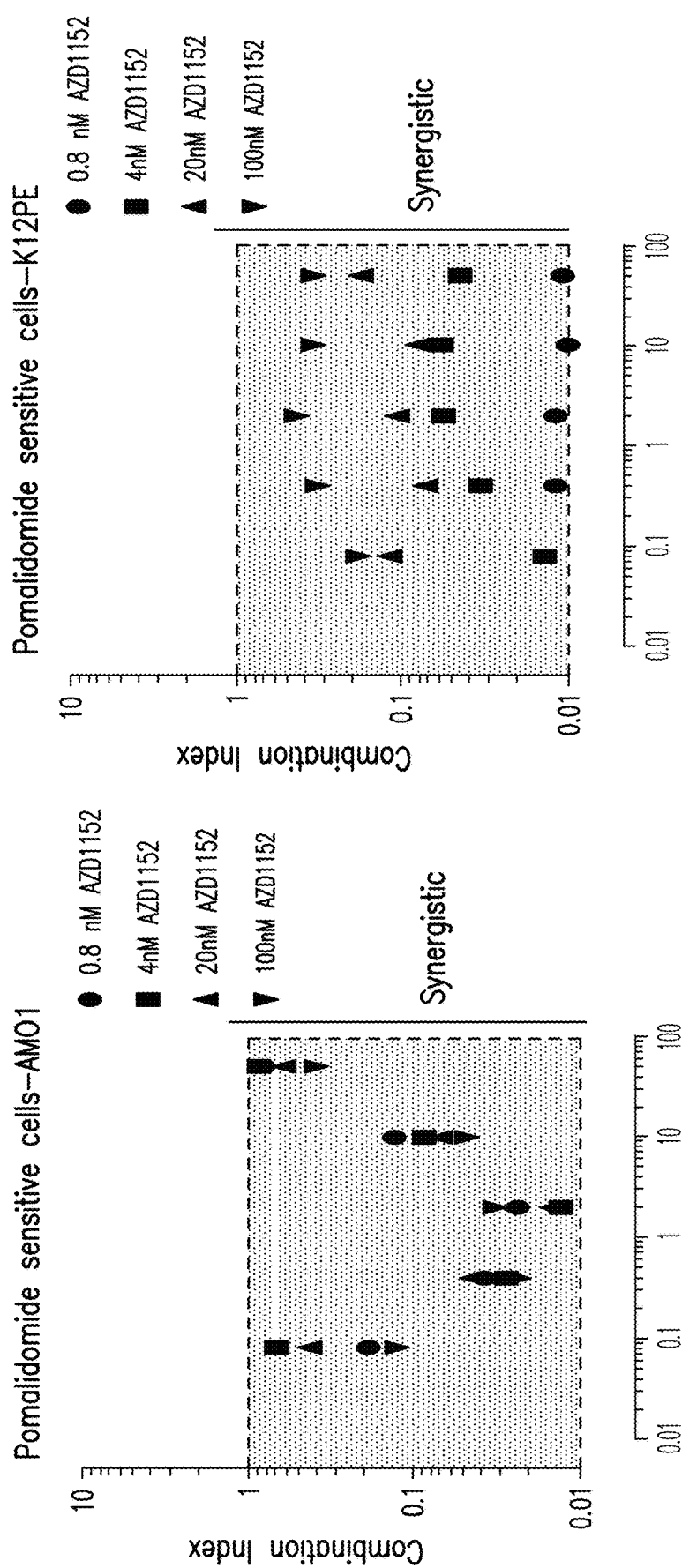
Figures 8C, 8D:
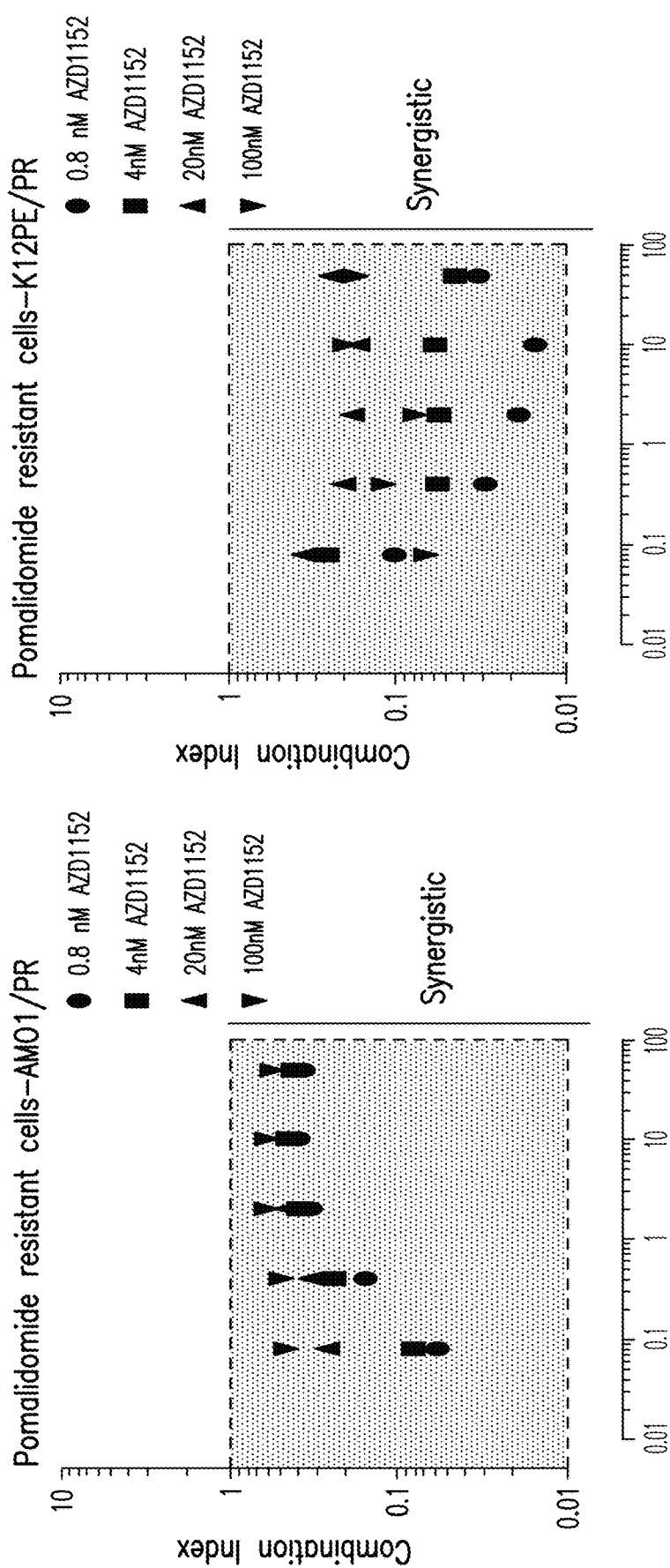

FIG. 8A shows the combination index for treatment of AMO1 cell lines with Compound 2 in combination with AZD1152; FIG. 8B shows the combination index for treatment of K12PE cell lines with Compound 2 in combination with AZD1152; FIG. 8C shows the combination index for treatment of AMO1-PR cell lines with Compound 2 in combination with AZD1152; and FIG. 8D shows the combination index for treatment of K12PE-PR cell lines with Compound 2 in combination with AZD1152.

Figures 9A, 9B:
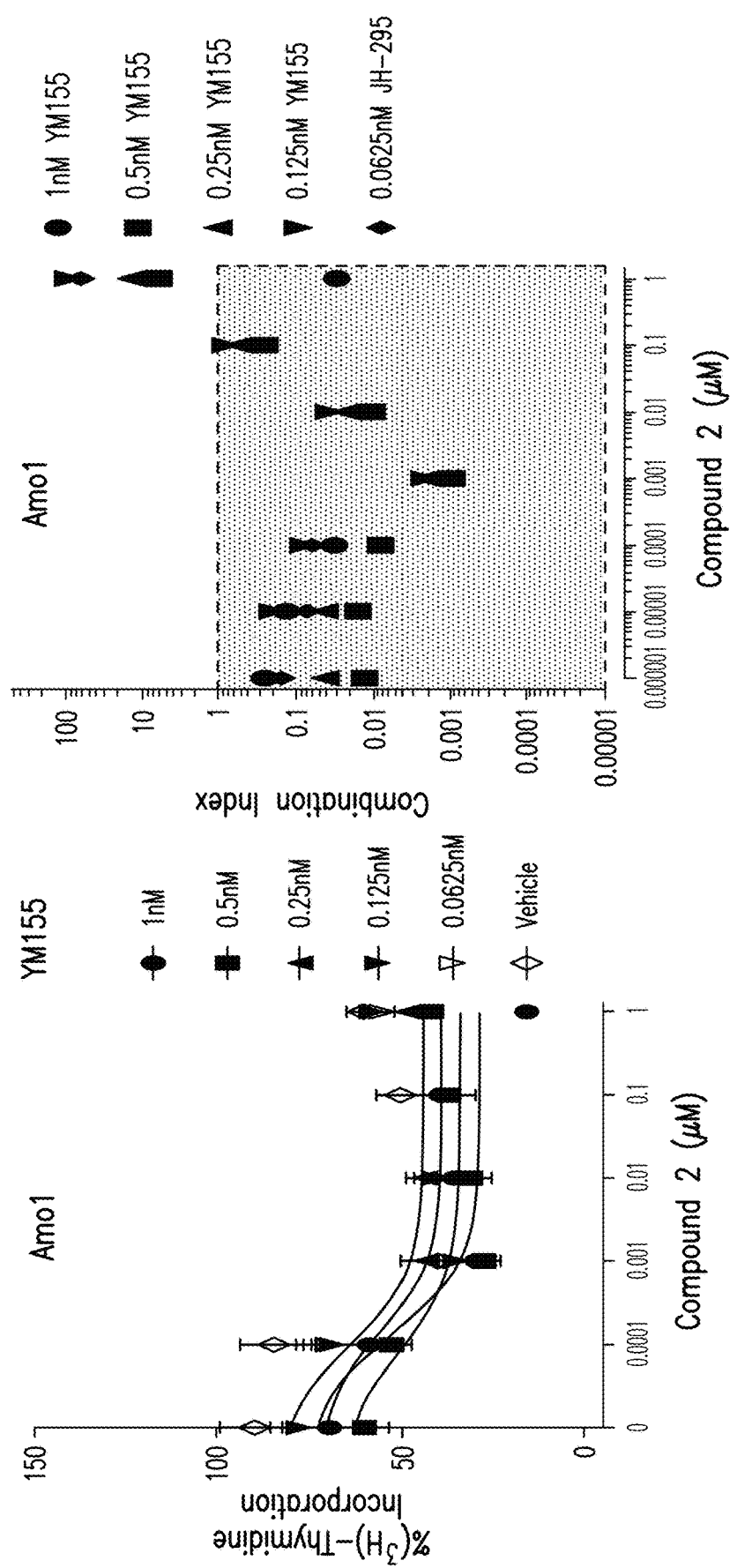
Figures 9C, 9D:
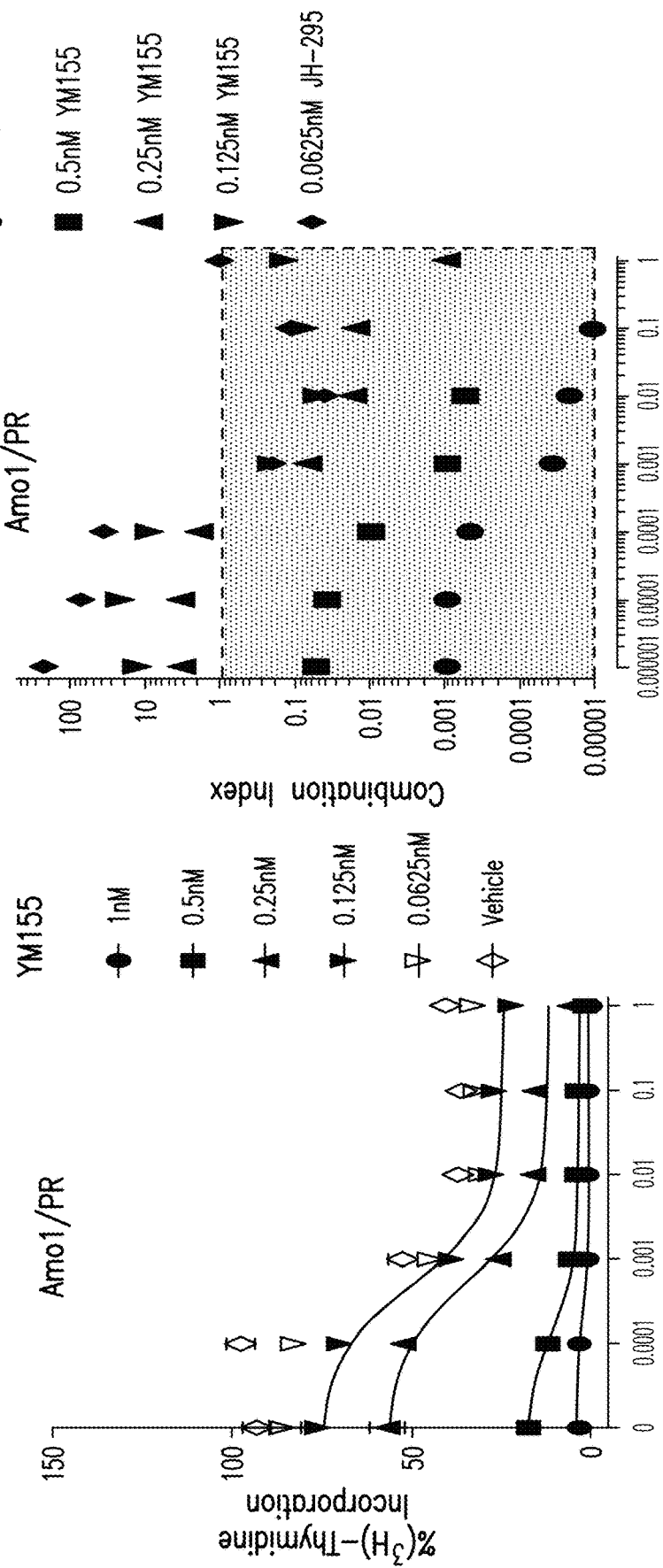

FIG. 9A shows the effect of treatment of AMO1 cell lines with Compound 2 in combination with YM155; FIG. 9B shows the corresponding combination index values; FIG. 9C shows the effect of treatment of AMO1-PR cell lines with Compound 2 in combination with YM155; and FIG. 9D shows the corresponding combination index values.

Figure 10A:
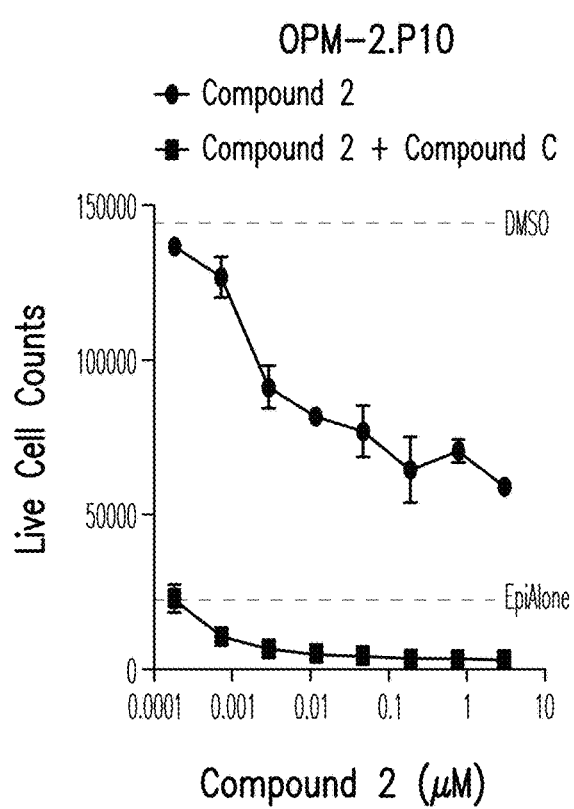
Figure 10B:
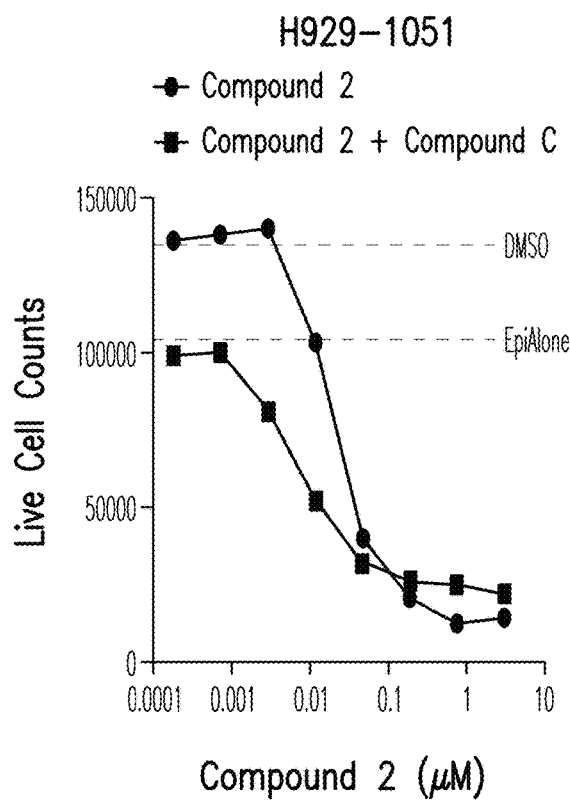
Figure 11A:
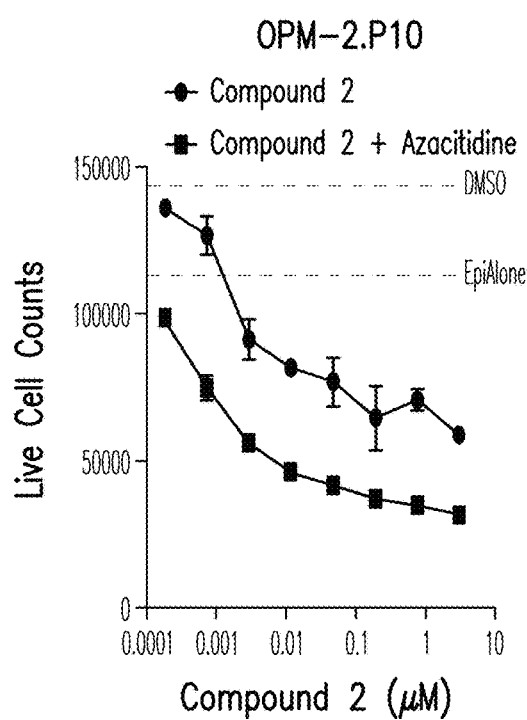
Figure 11B:
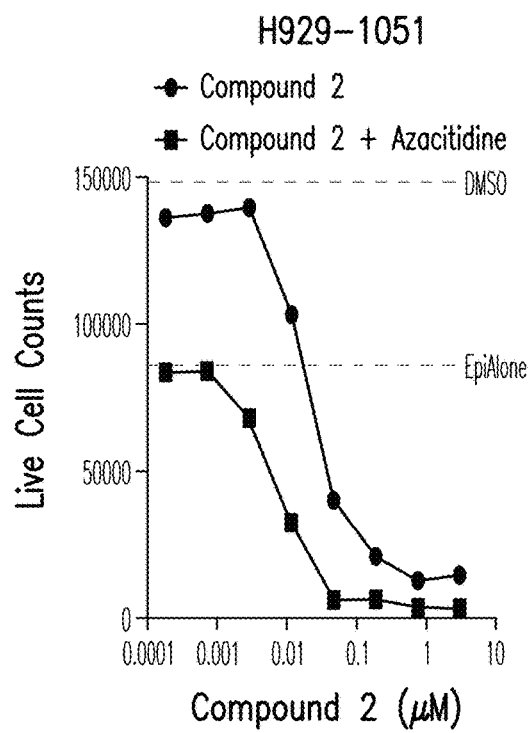
Figure 11C:
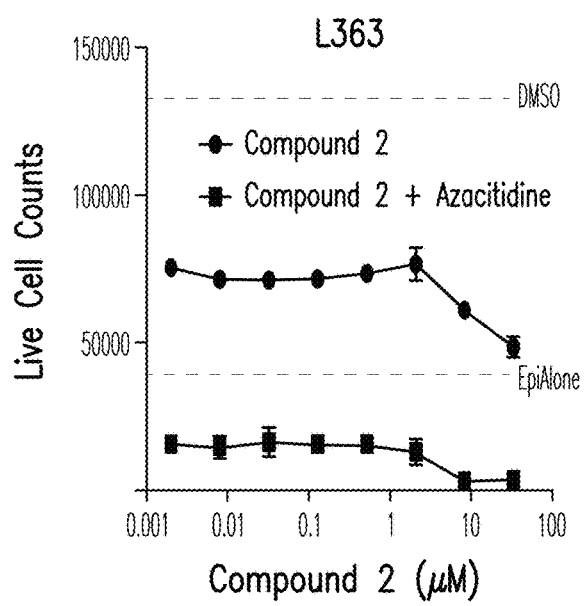
Figure 11D:
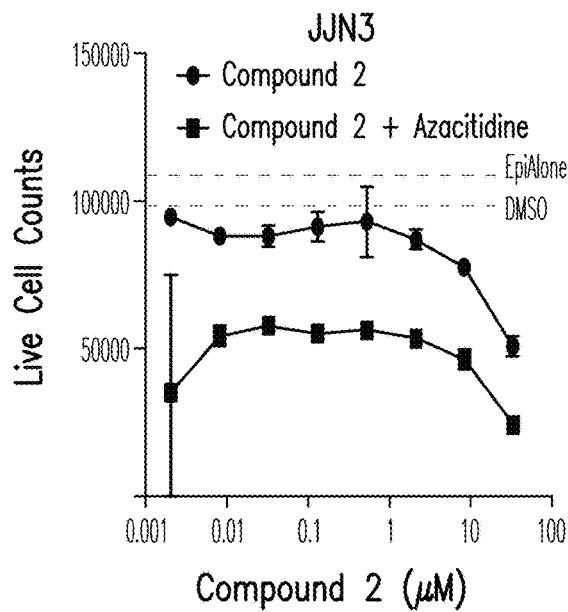
Figure 12A:
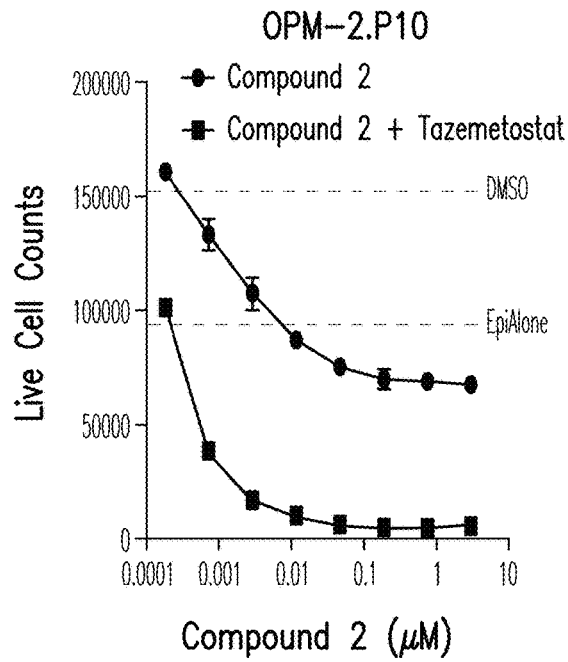
Figure 12B:
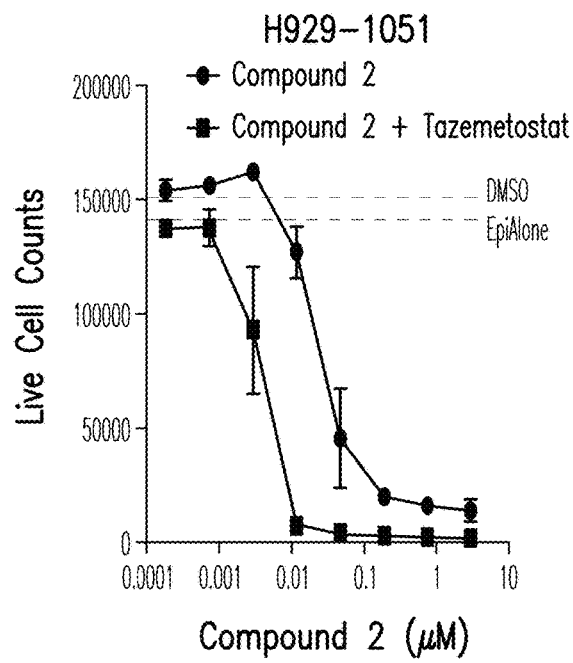
Figure 12C:
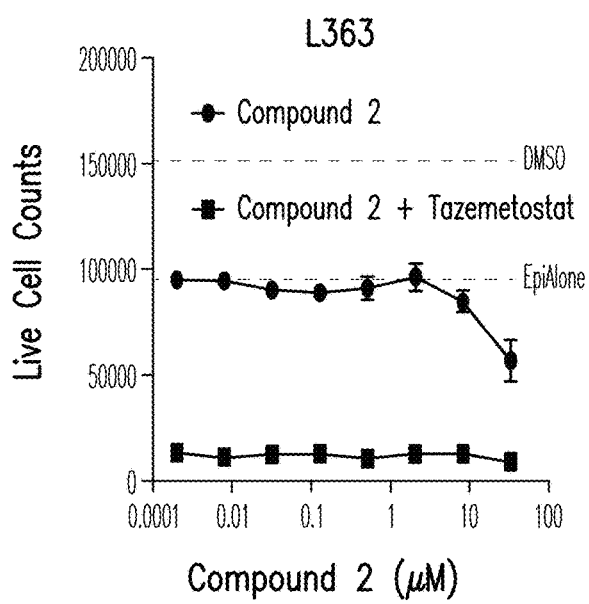
Figure 12D:
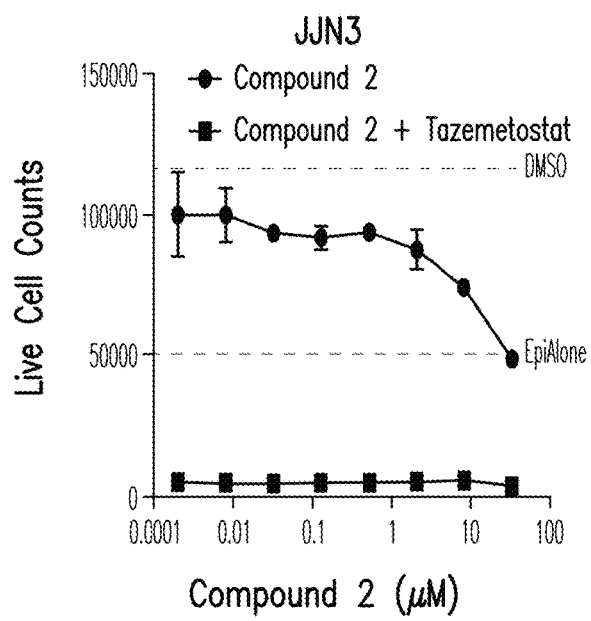
Figure 13A:
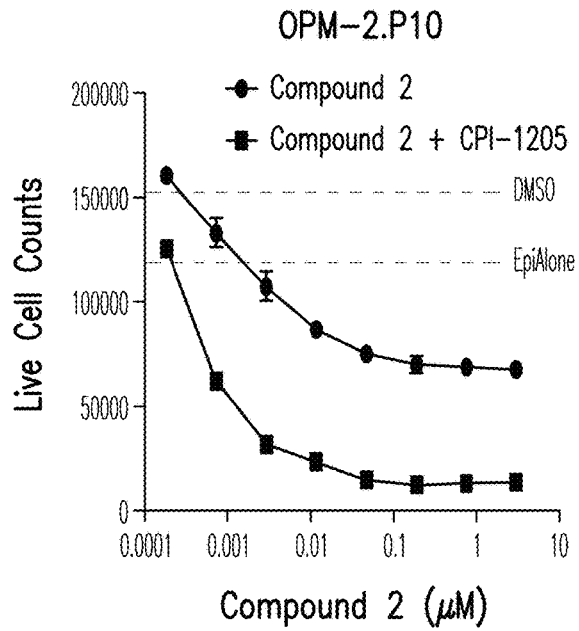
Figure 13B:
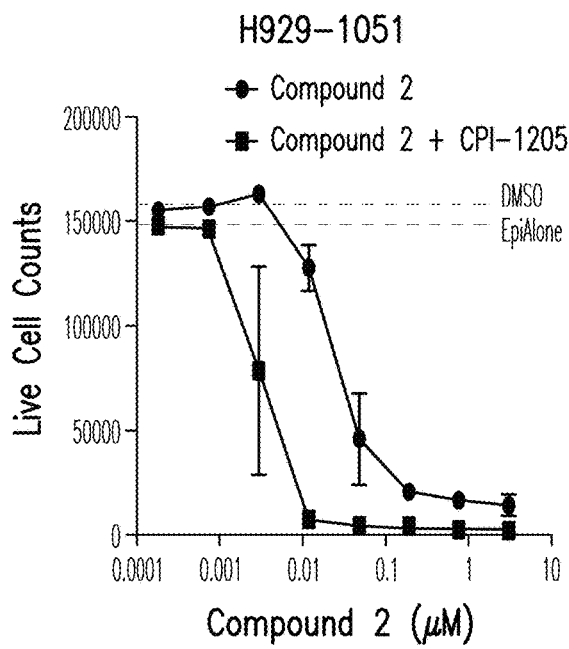
Figure 13C:
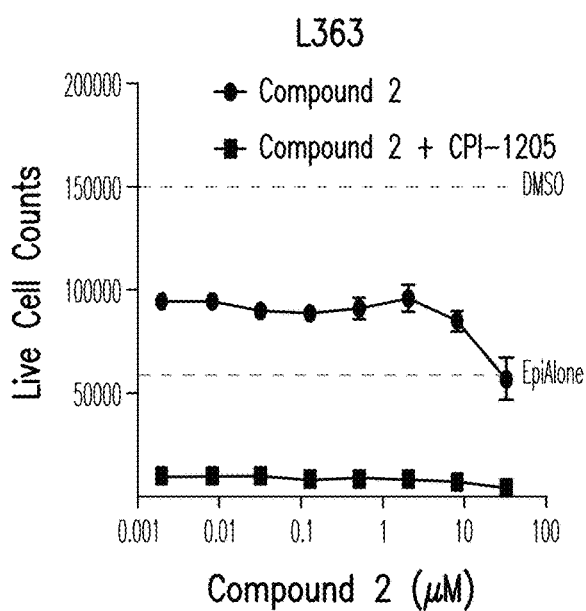
Figure 13D:
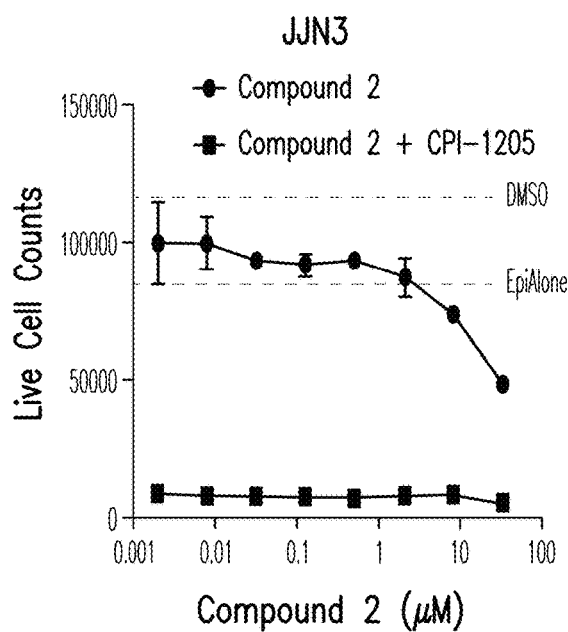

FIG. 10A and FIG. 10B show the effect of treatment with Compound 2 in combination with Compound C in OPM.2-P10 and H929-1051 MM cells, respectively.

FIG. 11A, FIG. 11B, FIG. 11C, and FIG. 11D show the effect of treatment with Compound 2 in combination with azacitidine in OPM.2-P10, H929-1051, L363, and JJN3 MM cells, respectively.

FIG. 12A, FIG. 12B, FIG. 12C, and FIG. 12D show the effect of treatment with Compound 2 in combination with tazemetostat in OPM.2-P10, H929-1051, L363, and JJN3 MM cells, respectively.

FIG. 13A, FIG. 13B, FIG. 13C, and FIG. 13D show the effect of treatment with Compound 2 in combination with CPI-1205 in OPM.2-P10, H929-1051, L363, and JJN3 MM cells, respectively.

Figure 14A:
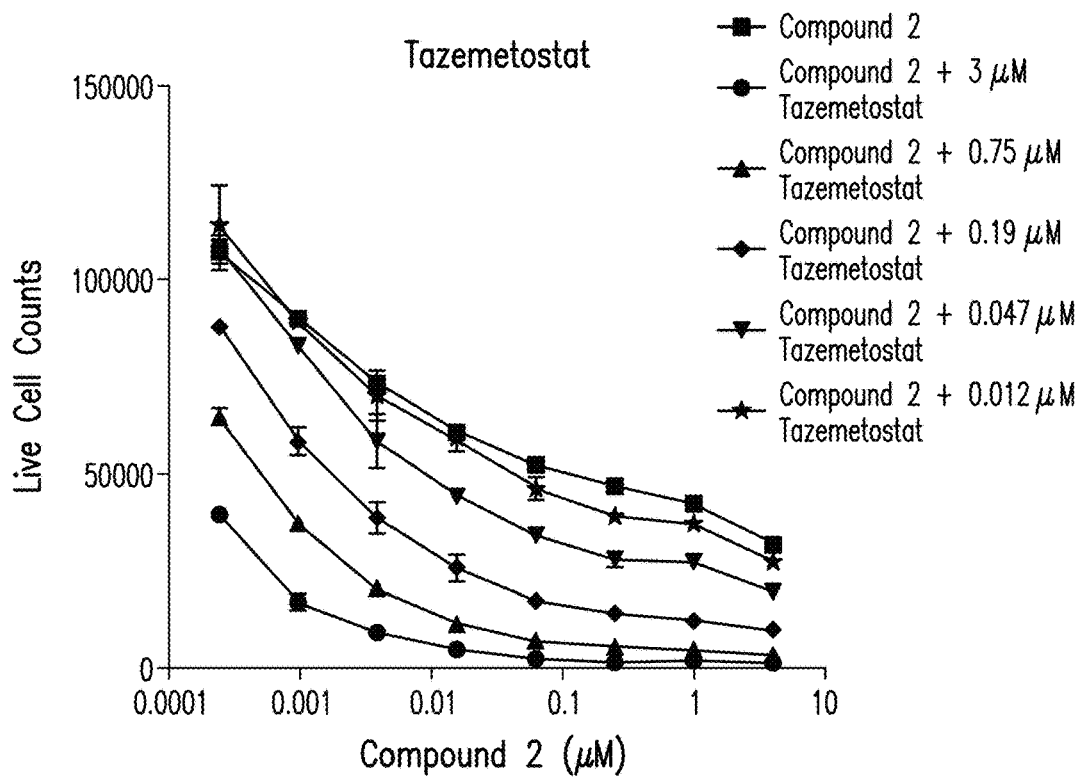
Figure 14B:
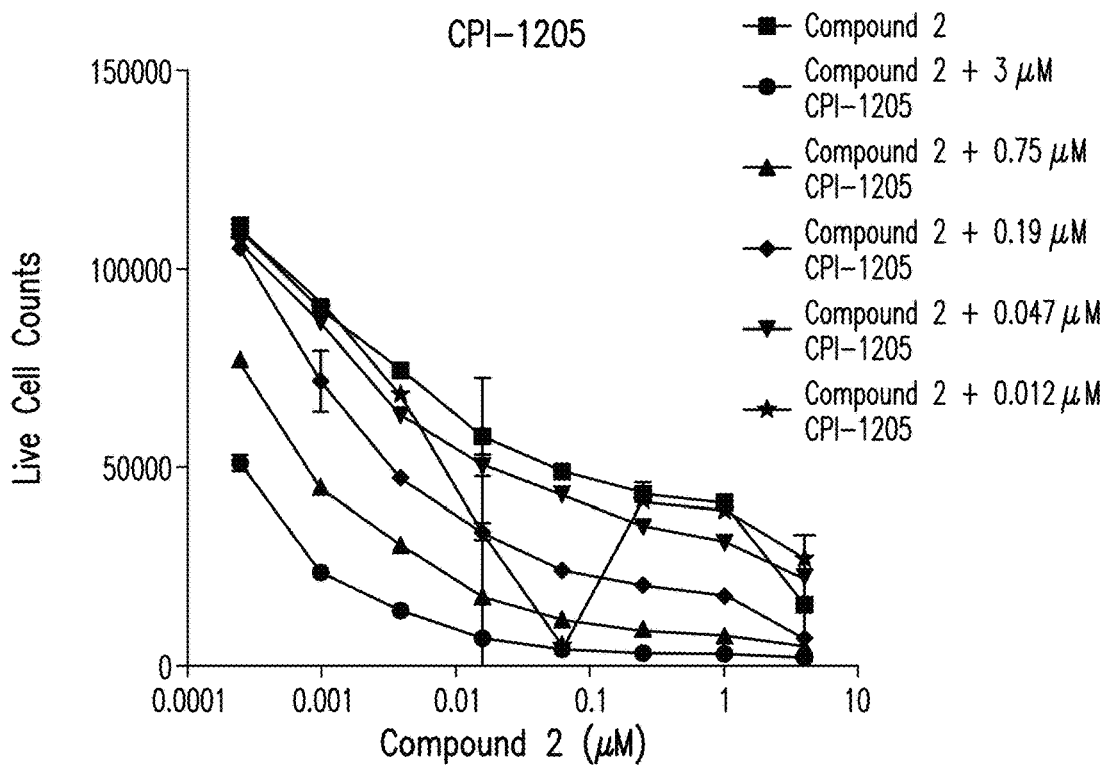
Figure 15A:
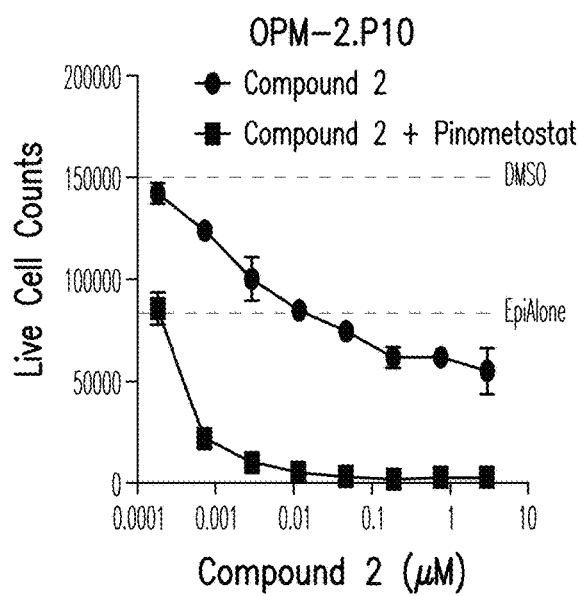
Figure 15B:
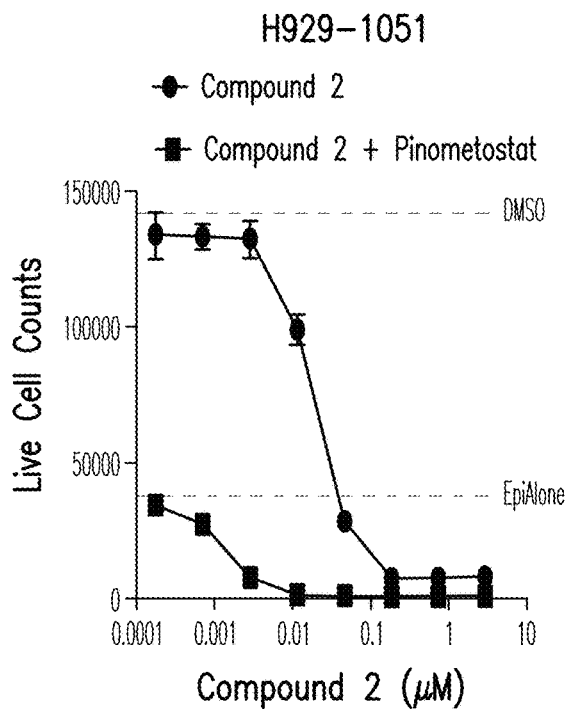
Figure 15C:
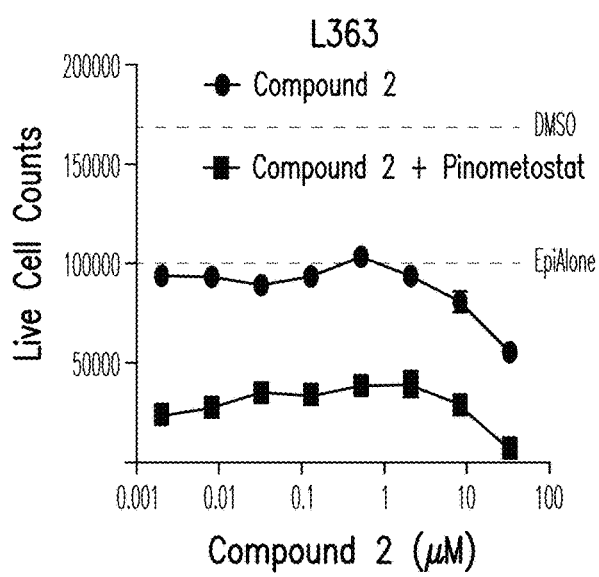
Figure 15D:
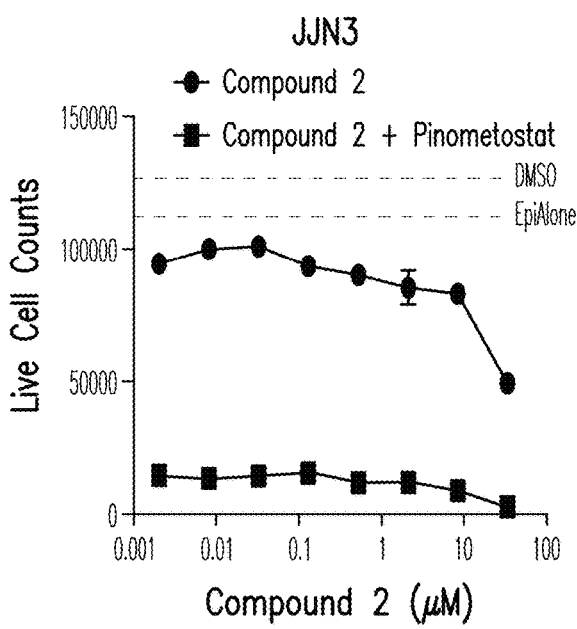

FIG. 14A and FIG. 14B show the effect of treatment in KMS12BM PR cells with Compound 2 in combination with tazemetostat and CPI-1205, respectively.

FIG. 15A, FIG. 15B, FIG. 15C, and FIG. 15D show the effect of treatment with Compound 2 in combination with pinometostat in OPM.2-P10, H929-1051, L363, and JJN3 MM cells, respectively.

C. COMPOUNDS

Provided for use in the methods herein is the compound 4-(4-(4-(((2-(2,6-dioxopiperidin-3-yl)-1-oxoisoindolin-4-yl)oxy)methyl)benzyl)piperazin-1-yl)-3-fluorobenzonitrile, referred to as "Compound 1":

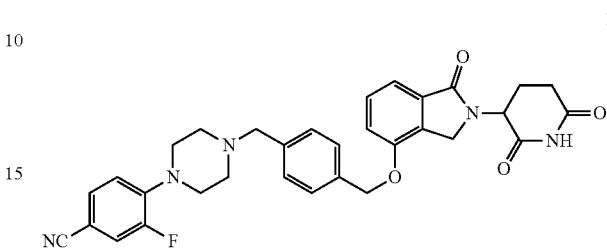

or an enantiomer or a mixture of enantiomers, tautomer, isotopolog or a pharmaceutically acceptable salt thereof.

Also provided for use in the methods provided herein is the compound (S)-4-(4-(4-(((2-(2,6-dioxopiperidin-3-yl)-1-oxoisoindolin-4-yl)oxy)methyl)benzyl)piperazin-1-yl)-3-fluorobenzonitrile, referred to as "Compound 2":

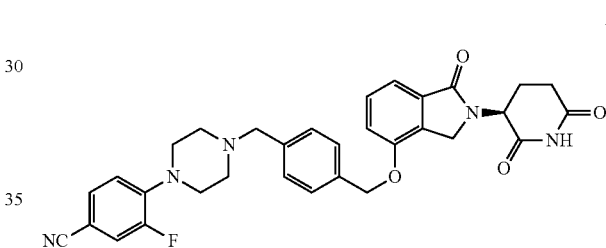

or a tautomer, isotopolog, or pharmaceutically acceptable salt thereof.

Also provided for use in the methods provided herein is the compound (R)-4-(4-(4-(((2-(2,6-dioxopiperidin-3-yl)-1-oxoisoindolin-4-yl)oxy)methyl)benzyl)piperazin-1-yl)-3-fluorobenzonitrile, referred to as "Compound 3":

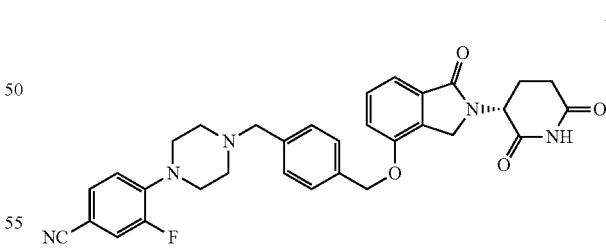

or a tautomer, isotopolog, or pharmaceutically acceptable salt thereof.

In one embodiment, Compound 1 is used in the methods provided herein. In one embodiment, a tautomer of Compound 1 is used in the methods provided herein. In one embodiment, an enantiomer of Compound 1 is used in the methods provided herein. In one embodiment, a mixture of enantiomers of Compound 1 is used in the methods provided herein. In one embodiment, a pharmaceutically acceptable salt of Compound 1 is used in the methods provided herein.

In one embodiment, Compound 2 is used in the methods provided herein. In one embodiment, a tautomer of a Compound 2 is used in the methods provided herein. In one embodiment, a pharmaceutically acceptable salt of Compound 2 is used in the methods provided herein.

In one embodiment, Compound 3 is used in the methods provided herein. In one embodiment, a tautomer of a Compound 3 is used in the methods provided herein. In one embodiment, a pharmaceutically acceptable salt of Compound 3 is used in the methods provided herein.

In one embodiment, isotopically enriched analogs of the compounds are used in the methods provided herein. In one embodiment, the isotopically enriched analogs of the compounds used in the methods provided herein include those described in U.S. application Ser. No. 16/030,695, which is incorporated herein by reference in its entirety.

D. Preparation of Compound 1, Compound 2 and Compound 3

The compounds for use in the methods provided herein can be prepared by methods known to one of skill in the art and following procedures similar to those described in the Examples section herein and routine modifications thereof. An exemplary reaction scheme for the preparation of the compounds is illustrated below in Scheme 1 for Compound 2.

Reaction of the methyl 2-(bromomethyl)-3-[tert-butyl(dimethyl)silyl]oxy-benzoate intermediate with the chiral tert-butyl (4S)-4,5-diamino-5-oxo-pentanoate (also referred to as H-L-Glu(OtBu)-NH$_2$; reaction with H-D-Glu(OtBu)-NH$_2$ provides the opposite enantiomer), in the presence of a base (such as DIEA), resulted in derivatized isoindoline formation, which was followed by TBS deprotection using tetrabutylammonium fluoride. Reaction of the derivatized isoindoline with 4-(4-(4-(chloromethyl)benzyl)piperazin-1-yl)-3-fluorobenzonitrile in the presence of a base (such as potassium carbonate), followed by deprotection and glutarimide formation afforded the target Compound 2. Compound 1 and Compound 3 can be prepared according to Scheme 1, but with corresponding racemic or R-enantiomer starting material, respectively. Preparation of Compound 1, Compound 2, and Compound 3 are also described in U.S. application Ser. No. 16/030,695, which is incorporated herein by reference in its entirety.

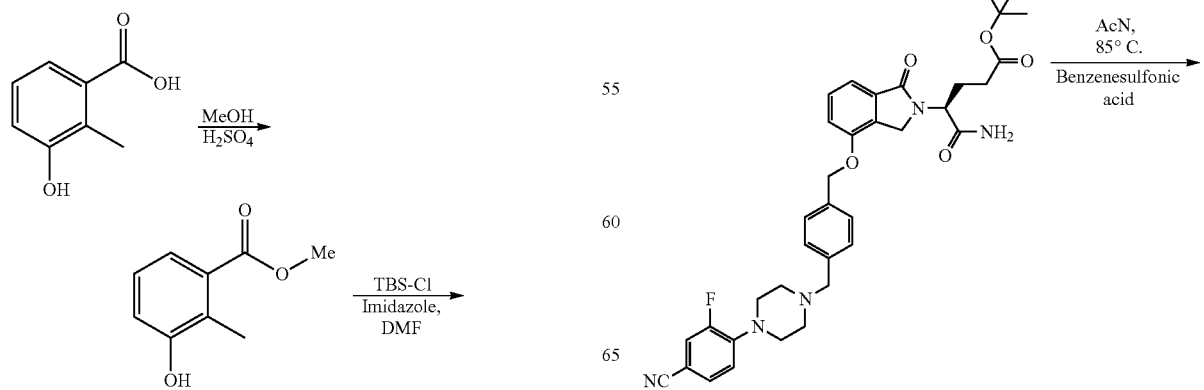

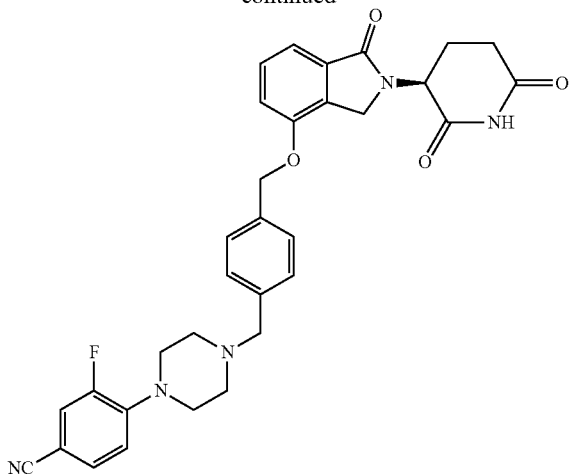

One skilled in the art would know how to modify the procedures set forth in the illustrative schemes and examples to arrive at the desired products.

E. Second Active Agents

In one embodiment, the second active agent used in the methods provided herein is a Bruton's tyrosine kinase (BTK) inhibitor. In one embodiment, the BTK inhibitor is ibrutinib, or acalabrutinib, or a stereoisomer, mixture of stereoisomers, tautomer, isotopolog, or pharmaceutically acceptable salt thereof. In one embodiment, the BTK inhibitor is ibrutinib, or a stereoisomer, mixture of stereoisomers, tautomer, isotopolog, or pharmaceutically acceptable salt thereof. In one embodiment, the BTK inhibitor is ibrutinib. In one embodiment, the BTK inhibitor is acalabrutinib. Ibrutinib has a chemical name of 1-[(3R)-3-[4-amino-3-(4-phenoxyphenyl)-1Hpyrazolo[3,4-d]pyrimidin-1-yl]-1-piperidinyl]-2-propen-1-one, and has the structure:

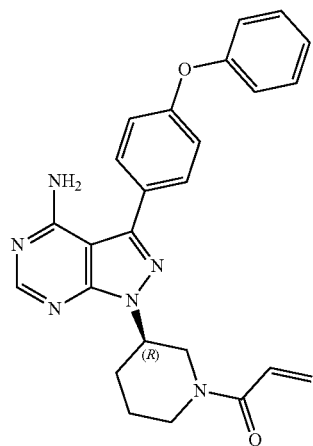

In one embodiment, the second active agent used in the methods provided herein is a mammalian target of rapamycin (mTOR) inhibitor. In one embodiment, the mTOR inhibitor is rapamycin or an analog thereof (also termed rapalog). In one embodiment, the mTOR inhibitor is everolimus, or a stereoisomer, mixture of stereoisomers, tautomer, isotopolog, or pharmaceutically acceptable salt thereof. In one embodiment, the mTOR inhibitor is everolimus. Everolimus has a chemical name of 40-O-(2-hydroxyethyl)-rapamycin, and has the structure:

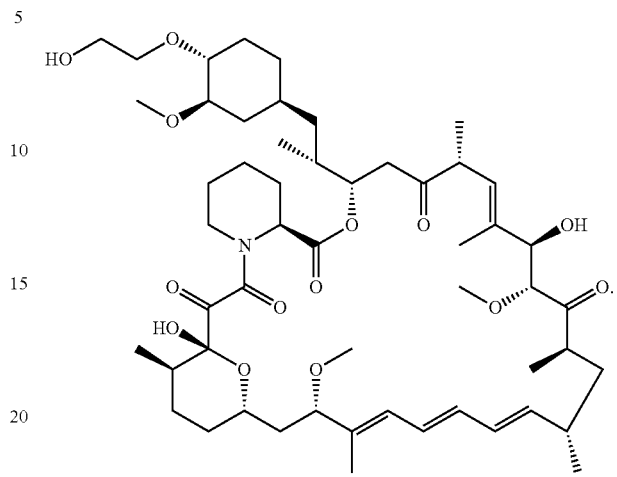

In one embodiment, the second active agent used in the methods provided herein is a proviral integration site for Moloney murine leukemia kinase (PIM) inhibitor. In one embodiment, the PIM inhibitor is a pan-PIM inhibitor. In one embodiment, the PIM inhibitor is LGH-447, AZD1208, SGI-1776, or TP-3654, or a stereoisomer, mixture of stereoisomers, tautomer, isotopolog, or pharmaceutically acceptable salt thereof. In one embodiment, the PIM inhibitor is LGH-447, or a stereoisomer, mixture of stereoisomers, tautomer, isotopolog, or pharmaceutically acceptable salt thereof. In one embodiment, the PIM inhibitor is LGH-447. In one embodiment, the PIM inhibitor is a pharmaceutically acceptable salt of LGH-447. In one embodiment, the PIM inhibitor is a hydrochloride salt of LGH-447. In one embodiment, the hydrochloride salt of LGH-447 is a di-hydrochloride salt. In one embodiment, the hydrochloride salt of LGH-447 is a mono-hydrochloride salt. In one embodiment, the PIM inhibitor is AZD1208. In one embodiment, the PIM inhibitor is SGI-1776. In one embodiment, the PIM inhibitor is TP-3654. LGH-447 has a chemical name of N-[4-[(1R,3S,5S)-3-amino-5-methylcyclohexyl]-3-pyridinyl]-6-(2,6-difluorophenyl)-5-fluoro-2-pyridinecarboxamide, and has the structure:

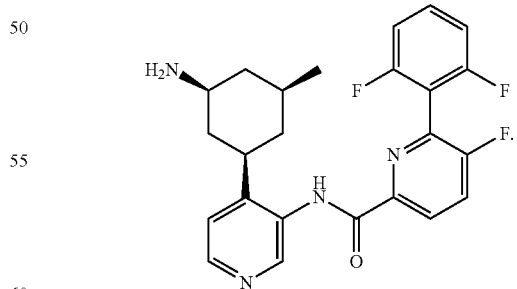

In one embodiment, the second active agent used in the methods provided herein is an insulin-like growth factor 1 receptor (IGF-1R) inhibitor. In one embodiment, the IGF-1R inhibitor is linsitinib, or a stereoisomer, mixture of stereoisomers, tautomer, isotopolog, or pharmaceutically acceptable salt thereof. In one embodiment, the IGF-1R inhibitor is linsitinib. Linsitinib has a chemical name of cis-3-[8-amino-1-(2-phenyl-7-quinolinyl)imidazo[1,5-a]pyrazin-3-yl]-1-methylcyclobutanol, and has the structure:

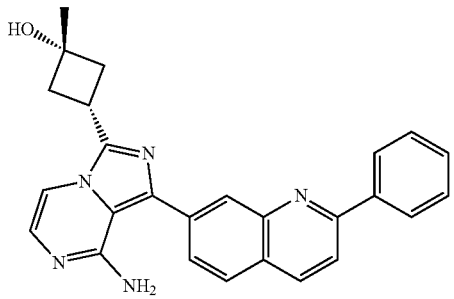

In one embodiment, the second active agent used in the methods provided herein is a mitogen-activated extracellular signal-regulated kinase (MEK) inhibitor. In one embodiment, the MEK inhibitor is trametinib, trametinib dimethyl sulfoxide, cobimetinib, binimetinib, or selumetinib, or a stereoisomer, mixture of stereoisomers, tautomer, isotopolog, or pharmaceutically acceptable salt thereof. In one embodiment, the MEK inhibitor is trametinib or trametinib dimethyl sulfoxide, or a stereoisomer, mixture of stereoisomers, tautomer, isotopolog, or pharmaceutically acceptable salt thereof. In one embodiment, the MEK inhibitor is trametinib. In one embodiment, the MEK inhibitor is trametinib dimethyl sulfoxide. In one embodiment, the MEK inhibitor is cobimetinib. In one embodiment, the MEK inhibitor is binimetinib. In one embodiment, the MEK inhibitor is selumetinib. Trametinib dimethyl sulfoxide has a chemical name of N-[3-[3-cyclopropyl-5-[(2-fluoro-4-iodophenyl)amino]-3,4,6,7-tetrahydro-6,8-dimethyl-2,4,7-trioxopyrido[4,3-d]pyrimidin-1(2H)-yl]phenyl]-acetamide, compound with dimethyl sulfoxide (1:1). Trametinib dimethyl sulfoxide has the structure:

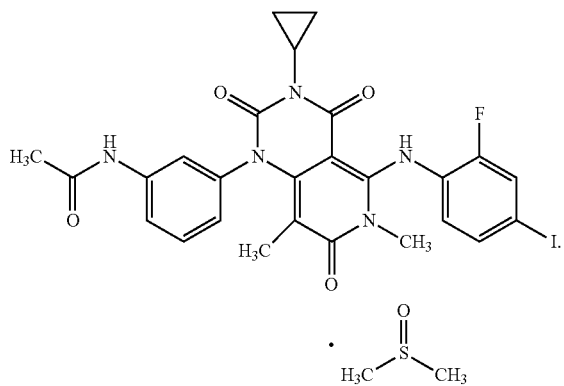

In one embodiment, the second active agent used in the methods provided herein is an exportin 1 (XPO1) inhibitor. In one embodiment, the XPO1 inhibitor is selinexor, or a stereoisomer, mixture of stereoisomers, tautomer, isotopolog, or pharmaceutically acceptable salt thereof. In one embodiment, the XPO1 inhibitor is selinexor. Selinexor has a chemical name of (2Z)-3-{3-[3,5-bis(trifluoromethyl)phenyl]-1H-1,2,4-triazol-1-yl}-N'-(pyrazin-2-yl)prop-2-enehydrazide, and has the structure:

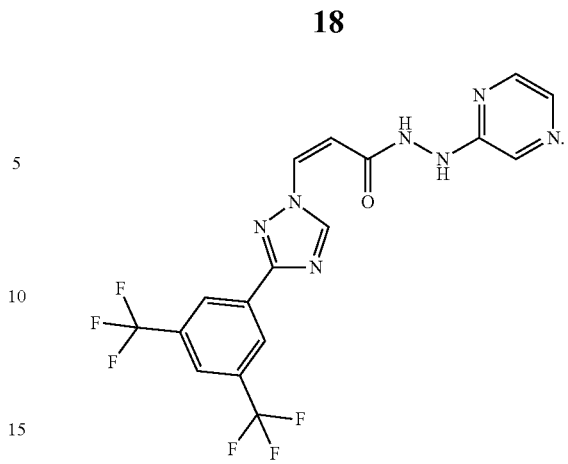

In one embodiment, the second active agent used in the methods provided herein is a disrupter of telomeric silencing 1-like (DOT1L) inhibitor. In one embodiment, the DOT1L inhibitor is SGC0946, or pinometostat, or a stereoisomer, mixture of stereoisomers, tautomer, isotopolog, or pharmaceutically acceptable salt thereof. In one embodiment, the DOT1L inhibitor is SGC0946, or a stereoisomer, mixture of stereoisomers, tautomer, isotopolog, or pharmaceutically acceptable salt thereof. In one embodiment, the DOT1L inhibitor is SGC0946. SGC0946 has a chemical name of 5 bromo-7-[5-deoxy-5-[[3-[[[[4-(1,1-dimethylethyl)phenyl]amino]carbonyl]amino]propyl](1-methylethyl)amino]-β-D-ribofuranosyl]-7H-pyrrolo[2,3-d]pyrimidin-4-amine, and has the structure:

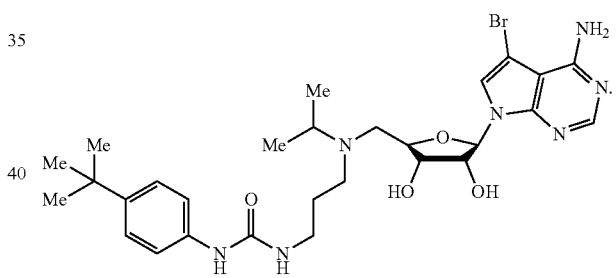

In one embodiment, the DOT1L inhibitor is pinometostat, or a stereoisomer, mixture of stereoisomers, tautomer, isotopolog, or pharmaceutically acceptable salt thereof. In one embodiment, the DOT1L inhibitor is pinometostat. Pinometostat (also known as EPZ-5676) has a chemical name of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol, and has the structure:

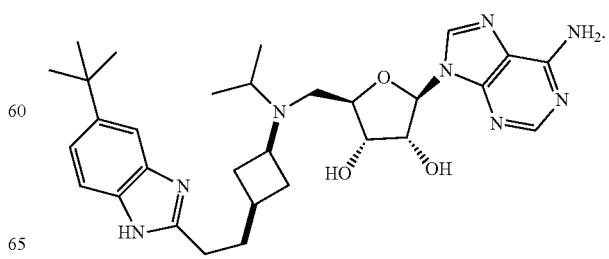

In one embodiment, the second active agent used in the methods provided herein is an enhancer of zeste homolog 2 (EZH2) inhibitor. In one embodiment, the EZH2 inhibitor is tazemetostat, 3-deazaneplanocin A (DZNep), EPZ005687, EI1, GSK126, UNC1999, CPI-1205, or sinefungin, or a stereoisomer, mixture of stereoisomers, tautomer, isotopolog, or pharmaceutically acceptable salt thereof. In one embodiment, the EZH2 inhibitor is tazemetostat, or a stereoisomer, mixture of stereoisomers, tautomer, isotopolog, or pharmaceutically acceptable salt thereof. In one embodiment, the EZH2 inhibitor is tazemetostat. In one embodiment, the EZH2 inhibitor is 3-deazaneplanocin A. In one embodiment, the EZH2 inhibitor is EPZ005687. In one embodiment, the EZH2 inhibitor is EI1. In one embodiment, the EZH2 inhibitor is GSK126. In one embodiment, the EZH2 inhibitor is sinefungin. Tazemetostat (also known as EPZ-6438) has a chemical name of N-[(1,2-dihydro-4,6-dimethyl-2-oxo-3-pyridinyl)methyl]-5-[ethyl(tetrahydro-2H-pyran-4-yl)amino]-4-methyl-4'-(4-morpholinylmethyl)-[1,1'-biphenyl]-3-carboxamide, and has the structure:

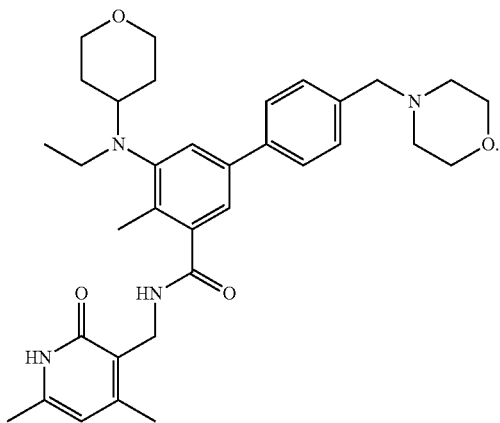 [SMILES: CCN(c1cc(-c2ccc(CN3CCOCC3)cc2)cc(C(=O)NCc2c(C)cc(C)[nH]c2=O)c1C)C1CCOCC1]

In one embodiment, the EZH2 inhibitor is UNC1999, or a tautomer, isotopolog, or pharmaceutically acceptable salt thereof. In one embodiment, the EZH2 inhibitor is UNC1999. UNC1999 has a chemical name of 1-Isopropyl-6-(6-(4-isopropylpiperazin-1-yl)pyridin-3-yl)-N-((6-methyl-2-oxo-4-propyl-1,2-dihydropyridin-3-yl)methyl)-1H-indazole-4-carboxamide, and has the structure:

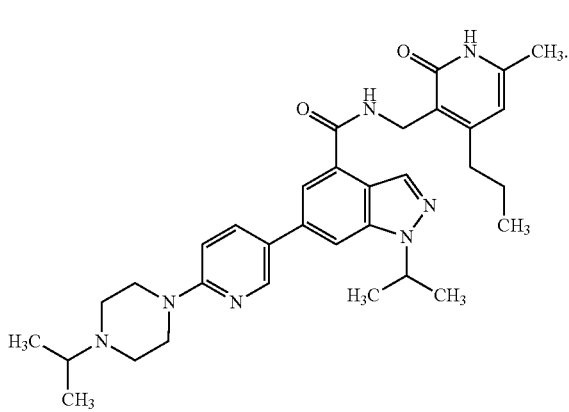 [SMILES: CCCc1cc(C)[nH]c(=O)c1CNC(=O)c1cc(-c2ccc(N3CCN(C(C)C)CC3)nc2)cc2c1cnn2C(C)C]

In one embodiment, the EZH2 inhibitor is CPI-1205, or a stereoisomer, mixture of stereoisomers, tautomer, isotopolog, or pharmaceutically acceptable salt thereof. In one embodiment, the EZH2 inhibitor is CPI-1205. CPI-1205 has a chemical name of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, and has the structure:

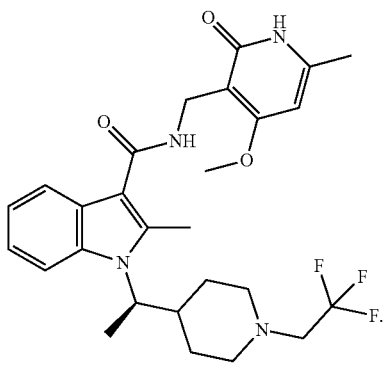 [SMILES: COc1cc(C)[nH]c(=O)c1CNC(=O)c1c(C)n([C@H](C)C2CCN(CC(F)(F)F)CC2)c2ccccc12]

In one embodiment, the second active agent used in the methods provided herein is a Janus kinase 2 (JAK2) inhibitor. In one embodiment, the JAK2 inhibitor is fedratinib, ruxolitinib, baricitinib, gandotinib, lestaurtinib, momelotinib, or pacritinib, or a stereoisomer, mixture of stereoisomers, tautomer, isotopolog, or pharmaceutically acceptable salt thereof. In one embodiment, the JAK2 inhibitor is fedratinib, or a tautomer, isotopolog, or pharmaceutically acceptable salt thereof. In one embodiment, the JAK2 inhibitor is fedratinib. In one embodiment, the JAK2 inhibitor is ruxolitinib. In one embodiment, the JAK2 inhibitor is baricitinib. In one embodiment, the JAK2 inhibitor is gandotinib. In one embodiment, the JAK2 inhibitor is lestaurtinib. In one embodiment, the JAK2 inhibitor is momelotinib. In one embodiment, the JAK2 inhibitor is pacritinib. Fedratinib has a chemical name of N-tert-butyl-3-[(5-methyl-2-{4-[2-(pyrrolidin-1-yl)ethoxy]anilino}pyrimidin-4-yl)amino]benzenesulfonamide, and has the structure:

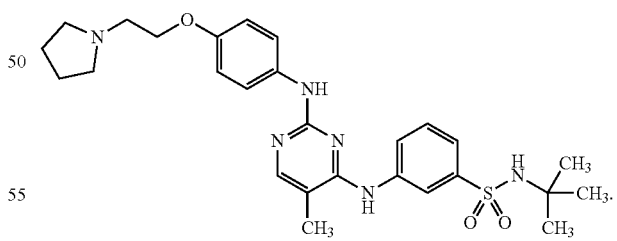

In one embodiment, the second active agent used in the methods provided herein is a bromodomain 4 (BRD4) inhibitor. In one embodiment, the BRD4 inhibitor is JQ1, or a stereoisomer, mixture of stereoisomers, tautomer, isotopolog, or pharmaceutically acceptable salt thereof. In one embodiment, the BRD4 inhibitor is JQ1. JQ1 has a chemical name of (S)-tert-butyl 2-(4-(4-chlorophenyl)-2,3,9-trimethyl-6H-thieno[3,2-J][1,2,4]triazolo[4,3-a][1,4]diazepin-6-yl)acetate, and has the structure:

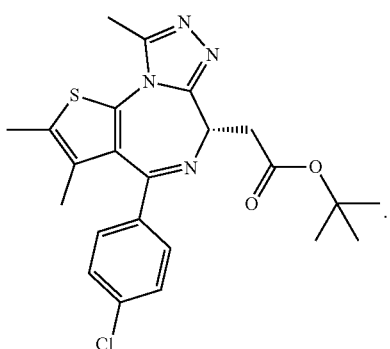 [SMILES: Cc1sc2c(c1C)C(c1ccc(Cl)cc1)=N[C@@H](CC(=O)OC(C)(C)C)c1nnc(C)n1-2]

In one embodiment, the second active agent used in the methods provided herein is a polo-like kinase 1 (PLK1) inhibitor. In one embodiment, the PLK1 inhibitor is BI2536, or a stereoisomer, mixture of stereoisomers, tautomer, isotopolog, or pharmaceutically acceptable salt thereof. In one embodiment, the PLK1 inhibitor is BI2536. BI2536 has a chemical name of (R)-4-((8-cyclopentyl-7-ethyl-5-methyl-6-oxo-5,6,7,8-tetrahydropteridin-2-yl)amino)-3-methoxy-N-(1-methylpiperidin-4-yl)benzamide, and has the structure:

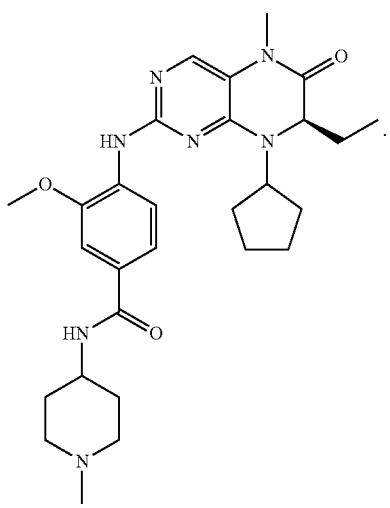 [SMILES: CC[C@@H]1C(=O)N(C)c2cnc(Nc3ccc(C(=O)NC4CCN(C)CC4)cc3OC)nc2N1C1CCCC1]

In one embodiment, the second active agent used in the methods provided herein is a serine/threonine-protein kinase (NEK2) inhibitor. In one embodiment, the NEK2 inhibitor is JH295, or a tautomer, isotopolog, or pharmaceutically acceptable salt thereof. In one embodiment, the NEK2 inhibitor is JH295. JH295 has a chemical name of (Z)—N-(3-((2-ethyl-4-methyl-1H-imidazol-5-yl)methylene)-2-oxoindolin-5-yl)propiolamide, and has the structure:

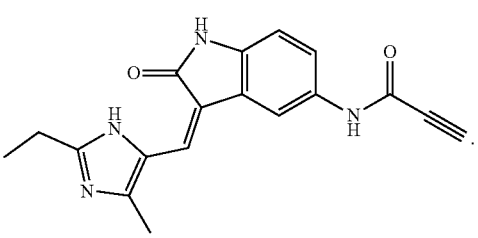 [SMILES: C#CC(=O)Nc1ccc2c(c1)/C(=C/c1[nH]c(CC)nc1C)C(=O)N2]

In one embodiment, the second active agent used in the methods provided herein is an Aurora kinase B (AURKB) inhibitor. In one embodiment, the AURKB inhibitor is barasertib (also known as AZD1152) or AZD1152-HQPA, or a tautomer, isotopolog, or pharmaceutically acceptable salt thereof. In one embodiment, the AURKB inhibitor is barasertib. In one embodiment, the AURKB inhibitor is AZD1152-HQPA. AZD1152-HQPA has a chemical name of 2-(3-((7-(3-(ethyl(2-hydroxyethyl)amino)propoxy)quinazolin-4-yl)amino)-1H-pyrazol-5-yl)-N-(3-fluorophenyl)acetamide, and has the structure:

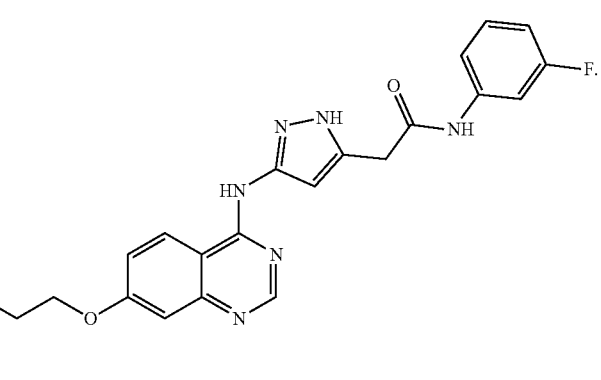

Barasertib is a dihydrogen phosphate prodrug of AZD1152-HQPA, and has the structure:

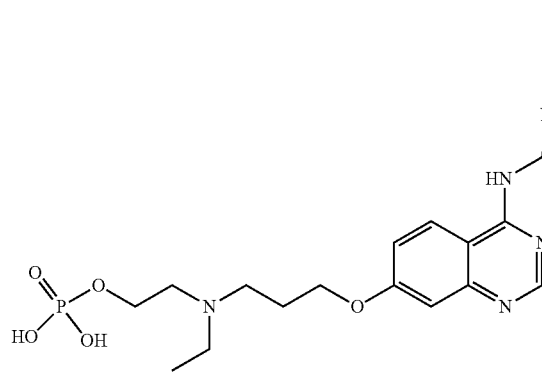

In one embodiment, the second active agent used in the methods provided herein is a survivin (also called baculoviral inhibitor of apoptosis repeat-containing 5 or BIRC5) inhibitor. In one embodiment, the BIRC5 inhibitor is YM155, or a tautomer, isotopolog, or pharmaceutically acceptable salt thereof. In one embodiment, the BIRC5 inhibitor is YM155. YM155 has a chemical name of 1-(2-methoxyethyl)-2-methyl-4,9-dioxo-3-(pyrazin-2-ylmethyl)-4,9-dihydro-1H-naphtho[2,3-d]imidazol-3-ium bromide, and has the structure:

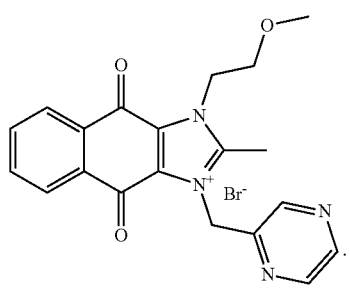 [SMILES: COCCn1c2c([n+](Cc3cnccn3)c1C)C(=O)c1ccccc1C2=O ; [Br-]]

In one embodiment, the second active agent used in the methods provided herein is a bromodomain and extra-terminal motif protein (BET) inhibitor. In one embodiment, the BET inhibitor is birabresib or Compound C, or a stereoisomer, mixture of stereoisomers, tautomer, isotopolog, or pharmaceutically acceptable salt thereof.

In one embodiment, the BET inhibitor is birabresib, or a stereoisomer, mixture of stereoisomers, tautomer, isotopolog, or pharmaceutically acceptable salt thereof. In one embodiment, the BET inhibitor is birabresib. Birabresib (also known as OTX015 or MK-8628) has a chemical name of (S)-2-(4-(4-chlorophenyl)-2,3,9-trimethyl-6H-thieno[3,2-f][1,2,4]triazolo[4,3-a][1,4]diazepin-6-yl)-N-(4-hydroxyphenyl)acetamide, and has the structure:

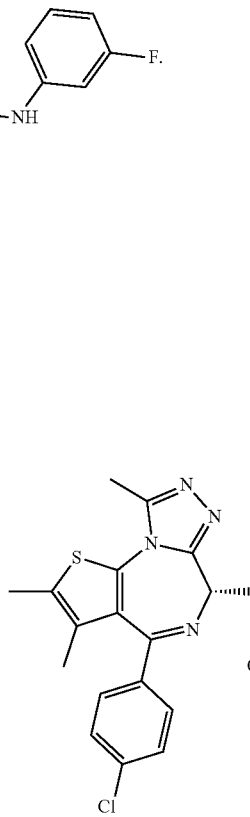

In one embodiment, the BET inhibitor is Compound C, or a tautomer, isotopolog, or pharmaceutically acceptable salt thereof. In one embodiment, the BET inhibitor is Compound C. Compound C has a chemical name of 4-[2-(cyclopropylmethoxy)-5-(methanesulfonyl)phenyl]-2-methylisoquinolin-1(2H)-one, and has the structure:

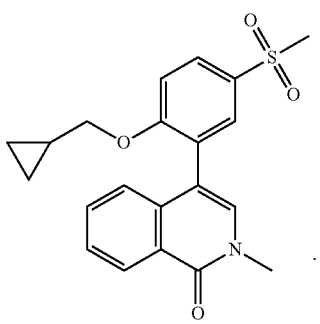 [SMILES: Cn1cc(-c2cc(S(C)(=O)=O)ccc2OCC2CC2)c2ccccc2c1=O]

In one embodiment, the second active agent used in the methods provided herein is a DNA methyltransferase inhibitor. In one embodiment, the DNA methyltransferase inhibitor is azacitidine, or a stereoisomer, mixture of stereoisomers, tautomer, isotopolog, or pharmaceutically acceptable salt thereof. In one embodiment, the hypomethylating agent is azacitidine. Azacitidine (also known as azacytidine or 5-azacytidine) has a chemical name of 4-amino-1-β-D-ribofuranosyl-1,3,5-triazin-2(1H)-one, and has the structure:

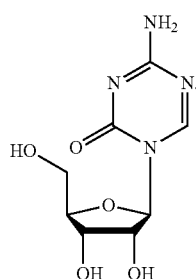

F. Methods of Treatment and Prevention

In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine). In one embodiment, provided herein is Compound 1, or an enantiomer, mixture of enantiomers, tautomer, isotopolog, or pharmaceutically acceptable salt thereof, for use in a method of treating multiple myeloma, wherein the method comprises administering to a patient a therapeutically effective amount of said compound in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine).

In one embodiment, provided herein is a method of treating multiple myeloma, which comprises administering to a patient a therapeutically effective amount of Compound 2, or a tautomer, isotopolog, or pharmaceutically acceptable salt thereof, in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine). In one embodiment, provided herein is Compound 2, or a tautomer, isotopolog, or pharmaceutically acceptable salt thereof, for use in a method of treating multiple myeloma, wherein the method comprises administering to a patient a therapeutically effective amount of said compound in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine).

In one embodiment, provided herein is a method of treating multiple myeloma, which comprises administering to a patient a therapeutically effective amount of Compound 3, or a tautomer, isotopolog, or pharmaceutically acceptable salt thereof, in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine). In one embodiment, provided herein is Compound 3, or a tautomer, isotopolog, or pharmaceutically acceptable salt thereof, for use in a method of treating multiple myeloma, wherein the method comprises administering to a patient said compound in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine).

In one embodiment, provided herein is a method of preventing multiple myeloma, which comprises administering to a patient a compound provided herein, e.g., Compound 1, Compound 2 or Compound 3, or an enantiomer, mixture of enantiomers, tautomer, isotopolog, or pharmaceutically acceptable salt thereof, in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine). In one embodiment, provided herein is a compound provided herein, e.g., Compound 1, Compound 2 or Compound 3, or an enantiomer, mixture of enantiomers, tautomer, isotopolog, or pharmaceutically acceptable salt thereof, for use in a method of preventing multiple myeloma, wherein the method comprises administering to a patient said compound in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine).

In another embodiment, provided herein is a method of managing multiple myeloma, which comprises administering to a patient a compound provided herein, e.g., Compound 1, Compound 2 or Compound 3, or an enantiomer, mixture of enantiomers, tautomer, isotopolog, or pharmaceutically acceptable salt thereof, in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine). In one embodiment, provided herein is a compound provided herein, e.g., Compound 1, Compound 2 or Compound 3, or an enantiomer, mixture of enantiomers, tautomer, isotopolog, or pharmaceutically acceptable salt thereof, for use in a method of managing multiple myeloma, wherein the method comprises administering to a patient said compound in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine).

In one embodiment, also provided herein are methods for inducing a therapeutic response assessed with the International Uniform Response Criteria for Multiple Myeloma (IURC) (see Durie B G M, Harousseau J-L, Miguel J S, et al. International uniform response criteria for multiple myeloma. *Leukemia,* 2006; (10) 10: 1-7) of a patient, comprising administering to a patient having multiple myeloma an effective amount of a compound described herein, e.g., Compound 1, Compound 2 or Compound 3, or an enantiomer, mixture of enantiomers, tautomer, isotopolog, or pharmaceutically acceptable salt thereof, in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine).

In another embodiment, provided herein are methods for achieving a stringent complete response, complete response, or very good partial response, as determined by the International Uniform Response Criteria for Multiple Myeloma (IURC) in a patient, comprising administering to a patient having multiple myeloma an effective amount of a compound described herein, e.g., Compound 1, Compound 2 or Compound 3, or an enantiomer, mixture of enantiomers, tautomer, isotopolog, or pharmaceutically acceptable salt thereof, in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine).

In another embodiment, provided herein are methods for achieving an increase in overall survival, progression-free survival, event-free survival, time to progression, or disease-free survival in a patient, comprising administering to a patient having multiple myeloma an effective amount of a compound described herein, e.g., Compound 1, Compound 2 or Compound 3, or an enantiomer, mixture of enantiomers, tautomer, isotopolog, or pharmaceutically acceptable salt thereof, in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine).

In another embodiment, provided herein are methods for achieving an increase in overall survival in a patient, comprising administering to a patient having multiple myeloma an effective amount of a compound described herein, e.g., Compound 1, Compound 2 or Compound 3, or an enantiomer, mixture of enantiomers, tautomer, isotopolog, or pharmaceutically acceptable salt thereof, in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine).

In another embodiment, provided herein are methods for achieving an increase in progression-free survival in a patient, comprising administering to a patient having multiple myeloma an effective amount of a compound described herein, e.g., Compound 1, Compound 2 or Compound 3, or an enantiomer, mixture of enantiomers, tautomer, isotopolog, or pharmaceutically acceptable salt thereof, in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine).

In another embodiment, provided herein are methods for achieving an increase in event-free survival in a patient, comprising administering to a patient having multiple myeloma an effective amount of a compound described herein, e.g., Compound 1, Compound 2 or Compound 3, or an enantiomer, mixture of enantiomers, tautomer, isotopolog, or pharmaceutically acceptable salt thereof, in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine).

In another embodiment, provided herein are methods for achieving an increase in time to progression in a patient, comprising administering to a patient having multiple myeloma an effective amount of a compound described herein, e.g., Compound 1, Compound 2 or Compound 3, or an enantiomer, mixture of enantiomers, tautomer, isotopolog, or pharmaceutically acceptable salt thereof, in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine).

In another embodiment, provided herein are methods for achieving an increase in disease-free survival in a patient, comprising administering to a patient having multiple myeloma an effective amount of a compound described herein, e.g., Compound 1, Compound 2 or Compound 3, or an enantiomer, mixture of enantiomers, tautomer, isotopolog, or pharmaceutically acceptable salt thereof, in combination with a second active agent, wherein the second active agent is one or more of a BTK inhibitor (e.g., ibrutinib), an mTOR inhibitor (e.g., everolimus), a PIM inhibitor (e.g., LGH-447), an IGF-1R inhibitor (e.g., linsitinib), an MEK inhibitor (e.g., trametinib), an XPO1 inhibitor (e.g., selinexor), a DOT1L inhibitor (e.g., SGC0946 or pinometostat), an EZH2 inhibitor (e.g., tazemetostat, UNC1999, or CPI-1205), a JAK2 inhibitor (e.g., fedratinib), a BRD4 inhibitor (e.g., JQ1), a PLK1 inhibitor (e.g., BI2536), an NEK2 inhibitor (e.g., JH295), an AURKB inhibitor (e.g., AZD1152), a BIRC5 inhibitor (e.g., YM155), a BET inhibitor (e.g., Compound C), or a DNA methyltransferase inhibitor (e.g., azacitidine).

In one embodiment, the second active agent used in the methods provided herein is a BTK inhibitor. In one embodiment, the BTK inhibitor is ibrutinib, or acalabrutinib, or a stereoisomer, mixture of stereoisomers, tautomer, isotopolog, or pharmaceutically acceptable salt thereof. In one embodiment, the BTK inhibitor is ibrutinib, or a stereoisomer, mixture of stereoisomers, tautomer, isotopolog, or pharmaceutically acceptable salt thereof. In one embodiment, the BTK inhibitor is ibrutinib. In one embodiment, the BTK inhibitor is acalabrutinib. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is ibrutinib, or a stereoisomer, mixture of stereoisomers, tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is ibrutinib. In one embodiment, the method additionally comprises administration of dexamethasone to the patient. In one embodiment, the method additionally comprises administration of bortezomib to the patient.

In one embodiment, the second active agent used in the methods provided herein is an mTOR inhibitor. In one embodiment, the mTOR inhibitor is rapamycin or an analog thereof (also termed rapalog). In one embodiment, the mTOR inhibitor is everolimus, or a stereoisomer, mixture of stereoisomers, tautomer, isotopolog, or pharmaceutically acceptable salt thereof. In one embodiment, the mTOR inhibitor is everolimus. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is everolimus, or a stereoisomer, mixture of stereoisomers, tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is everolimus. In one embodiment, the method additionally comprises administration of dexamethasone to the patient. In one embodiment, the method additionally comprises administration of bortezomib to the patient.

In one embodiment, the second active agent used in the methods provided herein is a PIM inhibitor. In one embodiment, the PIM inhibitor is a pan-PIM inhibitor. In one embodiment, the PIM inhibitor is LGH-447, AZD1208, SGI-1776, or TP-3654, or a stereoisomer, mixture of stereoisomers, tautomer, isotopolog, or pharmaceutically acceptable salt thereof. In one embodiment, the PIM inhibitor is LGH-447, or a stereoisomer, mixture of stereoisomers, tautomer, isotopolog, or pharmaceutically acceptable salt thereof. In one embodiment, the PIM inhibitor is LGH-447. In one embodiment, the PIM inhibitor is a pharmaceutically acceptable salt of LGH-447. In one embodiment, the PIM inhibitor is a hydrochloride salt of LGH-447. In one embodiment, the hydrochloride salt of LGH-447 is a di-hydrochloride salt. In one embodiment, the hydrochloride salt of LGH-447 is a mono-hydrochloride salt. In one embodiment, the PIM inhibitor is AZD1208. In one embodiment, the PIM inhibitor is SGI-1776. In one embodiment, the PIM inhibitor is TP-3654. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is LGH-447, or a stereoisomer, mixture of stereoisomers, tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is LGH-447. In one embodiment, the method additionally comprises administration of dexamethasone to the patient. In one embodiment, the method additionally comprises administration of bortezomib to the patient.

In one embodiment, the second active agent used in the methods provided herein is an IGF-1R inhibitor. In one embodiment, the IGF-1R inhibitor is linsitinib, or a stereoisomer, mixture of stereoisomers, tautomer, isotopolog, or pharmaceutically acceptable salt thereof. In one embodiment, the IGF-1R inhibitor is linsitinib. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is linsitinib, or a stereoisomer, mixture of stereoisomers, tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is linsitinib. In one embodiment, the method additionally comprises administration of dexamethasone to the patient. In one embodiment, the method additionally comprises administration of bortezomib to the patient.

In one embodiment, the second active agent used in the methods provided herein is an MEK inhibitor. In one embodiment, the MEK inhibitor is trametinib, trametinib dimethyl sulfoxide, cobimetinib, binimetinib, or selumetinib, or a stereoisomer, mixture of stereoisomers, tautomer, isotopolog, or pharmaceutically acceptable salt thereof. In one embodiment, the MEK inhibitor is trametinib or trametinib dimethyl sulfoxide, or a stereoisomer, mixture of stereoisomers, tautomer, isotopolog, or pharmaceutically acceptable salt thereof. In one embodiment, the MEK inhibitor is trametinib. In one embodiment, the MEK inhibitor is trametinib dimethyl sulfoxide. In one embodiment, the MEK inhibitor is cobimetinib. In one embodiment, the MEK inhibitor is binimetinib. In one embodiment, the MEK inhibitor is selumetinib. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is trametinib or trametinib dimethyl sulfoxide, or a stereoisomer, mixture of stereoisomers, tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is trametinib. In one embodiment, provided herein is a method of treating multiple myeloma, which comprises administering to a patient a therapeutically effective amount of Compound 2 in combination with a second active agent, wherein the second active agent is trametinib dimethyl sulfoxide. In one embodiment, the method additionally comprises administration of dexamethasone to the patient. In one embodiment, the method additionally comprises administration of bortezomib to the patient.

In one embodiment, the second active agent used in the methods provided herein is an XPO1 inhibitor. In one embodiment, the XPO1 inhibitor is selinexor, or a stereoisomer, mixture of stereoisomers, tautomer, isotopolog, or pharmaceutically acceptable salt thereof. In one embodiment, the XPO1 inhibitor is selinexor. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is selinexor, or a stereoisomer, mixture of stereoisomers, tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is selinexor. In one embodiment, the method additionally comprises administration of dexamethasone to the patient. In one embodiment, the method additionally comprises administration of bortezomib to the patient.

In one embodiment, the second active agent used in the methods provided herein is a DOT1L inhibitor. In one embodiment, the DOT1L inhibitor is SGC0946, or pinometostat, or a stereoisomer, mixture of stereoisomers, tautomer, isotopolog, or pharmaceutically acceptable salt thereof. In one embodiment, the DOT1L inhibitor is SGC0946, or a stereoisomer, mixture of stereoisomers, tautomer, isotopolog, or pharmaceutically acceptable salt thereof. In one embodiment, the DOT1L inhibitor is SGC0946. In one embodiment, the DOT1L inhibitor is pinometostat, or a stereoisomer, mixture of stereoisomers, tautomer, isotopolog, or pharmaceutically acceptable salt thereof. In one embodiment, the DOT1L inhibitor is pinometostat. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is SGC0946, or a stereoisomer, mixture of stereoisomers, tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is SGC0946. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is pinometostat, or a stereoisomer, mixture of stereoisomers, tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is pinometostat. In one embodiment, the method additionally comprises administration of dexamethasone to the patient. In one embodiment, the method additionally comprises administration of bortezomib to the patient.

In one embodiment, the second active agent used in the methods provided herein is an EZH2 inhibitor. In one embodiment, the EZH2 inhibitor is tazemetostat, 3-deazaneplanocin A (DZNep), EPZ005687, EI1, GSK126, UNC1999, CPI-1205, or sinefungin, or a stereoisomer, mixture of stereoisomers, tautomer, isotopolog, or pharmaceutically acceptable salt thereof. In one embodiment, the EZH2 inhibitor is tazemetostat, or a stereoisomer, mixture of stereoisomers, tautomer, isotopolog, or pharmaceutically acceptable salt thereof. In one embodiment, the EZH2 inhibitor is tazemetostat. In one embodiment, the EZH2 inhibitor is 3-deazaneplanocin A. In one embodiment, the EZH2 inhibitor is EPZ005687. In one embodiment, the EZH2 inhibitor is EI1. In one embodiment, the EZH2 inhibitor is GSK126. In one embodiment, the EZH2 inhibitor is UNC1999, or a tautomer, isotopolog, or pharmaceutically acceptable salt thereof. In one embodiment, the EZH2 inhibitor is UNC1999. In one embodiment, the EZH2 inhibitor is CPI-1205, or a stereoisomer, mixture of stereoisomers, tautomer, isotopolog, or pharmaceutically acceptable salt thereof. In one embodiment, the EZH2 inhibitor is CPI-1205. In one embodiment, the EZH2 inhibitor is sinefungin. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is tazemetostat, or a stereoisomer, mixture of stereoisomers, tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is tazemetostat. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is UNC1999, or a tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is UNC1999. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is CPI-1205, or a stereoisomer, mixture of stereoisomers, tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is CPI-1205. In one embodiment, the method additionally comprises administration of dexamethasone to the patient. In one embodiment, the method additionally comprises administration of bortezomib to the patient.

In one embodiment, the second active agent used in the methods provided herein is a JAK2 inhibitor. In one embodiment, the JAK2 inhibitor is fedratinib, ruxolitinib, baricitinib, gandotinib, lestaurtinib, momelotinib, or pacritinib, or a stereoisomer, mixture of stereoisomers, tautomer, isotopolog, or pharmaceutically acceptable salt thereof. In one embodiment, the JAK2 inhibitor is fedratinib, or a tautomer, isotopolog, or pharmaceutically acceptable salt thereof. In one embodiment, the JAK2 inhibitor is fedratinib. In one embodiment, the JAK2 inhibitor is ruxolitinib. In one embodiment, the JAK2 inhibitor is baricitinib. In one embodiment, the JAK2 inhibitor is gandotinib. In one embodiment, the JAK2 inhibitor is lestaurtinib. In one embodiment, the JAK2 inhibitor is momelotinib. In one embodiment, the JAK2 inhibitor is pacritinib. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is fedratinib, or a tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is fedratinib. In one embodiment, the method additionally comprises administration of dexamethasone to the patient. In one embodiment, the method additionally comprises administration of bortezomib to the patient.

In one embodiment, the second active agent used in the methods provided herein is a BRD4 inhibitor. In one embodiment, the BRD4 inhibitor is JQ1, or a stereoisomer, mixture of stereoisomers, tautomer, isotopolog, or pharmaceutically acceptable salt thereof. In one embodiment, the BRD4 inhibitor is JQ1. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is JQ1, or a stereoisomer, mixture of stereoisomers, tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is JQ1. In one embodiment, the method additionally comprises administration of dexamethasone to the patient. In one embodiment, the method additionally comprises administration of bortezomib to the patient.

In one embodiment, the second active agent used in the methods provided herein is a PLK1 inhibitor. In one embodiment, the PLK1 inhibitor is BI2536, or a stereoisomer, mixture of stereoisomers, tautomer, isotopolog, or pharmaceutically acceptable salt thereof. In one embodiment, the PLK1 inhibitor is BI2536. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is BI2536, or a stereoisomer, mixture of stereoisomers, tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is BI2536. In one embodiment, the method additionally comprises administration of dexamethasone to the patient. In one embodiment, the method additionally comprises administration of bortezomib to the patient.

In one embodiment, the second active agent used in the methods provided herein is an NEK2 inhibitor. In one embodiment, the NEK2 inhibitor is JH295, or a tautomer, isotopolog, or pharmaceutically acceptable salt thereof. In one embodiment, the NEK2 inhibitor is JH295. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is JH295, or a tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is JH295. In one embodiment, the method additionally comprises administration of dexamethasone to the patient. In one embodiment, the method additionally comprises administration of bortezomib to the patient.

In one embodiment, the second active agent used in the methods provided herein is an AURKB inhibitor. In one embodiment, the AURKB inhibitor is barasertib (AZD1152) or AZD1152-HQPA, or a tautomer, isotopolog, or pharmaceutically acceptable salt thereof. In one embodiment, the AURKB inhibitor is barasertib. In one embodiment, the AURKB inhibitor is AZD1152-HQPA. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is barasertib or AZD1152-HQPA, or a tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is barasertib. In one embodiment, provided herein is a method of treating multiple myeloma, which comprises administering to a patient a therapeutically effective amount of Compound 2 in combination with a second active agent, wherein the second active agent is AZD1152-HQPA. In one embodiment, the method additionally comprises administration of dexamethasone to the patient. In one embodiment, the method additionally comprises administration of bortezomib to the patient.

In one embodiment, the second active agent used in the methods provided herein is a BIRC5 inhibitor. In one embodiment, the BIRC5 inhibitor is YM155, or a tautomer, isotopolog, or pharmaceutically acceptable salt thereof. In one embodiment, the BIRC5 inhibitor is YM155. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is YM155, or a tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is YM155. In one embodiment, the method additionally comprises administration of dexamethasone to the patient. In one embodiment, the method additionally comprises administration of bortezomib to the patient.

In one embodiment, the second active agent used in the methods provided herein is a BET inhibitor. In one embodiment, the BET inhibitor is birabresib or Compound C, or a stereoisomer, mixture of stereoisomers, tautomer, isotopolog, or pharmaceutically acceptable salt thereof. In one embodiment, the BET inhibitor is birabresib, or a stereoisomer, mixture of stereoisomers, tautomer, isotopolog, or pharmaceutically acceptable salt thereof. In one embodiment, the BET inhibitor is birabresib. In one embodiment, the BET inhibitor is Compound C, or a tautomer, isotopolog, or pharmaceutically acceptable salt thereof. In one embodiment, the BET inhibitor is Compound C. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is birabresib, or a stereoisomer, mixture of stereoisomers, tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is birabresib. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is Compound C, or a tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is Compound C. In one embodiment, the method additionally comprises administration of dexamethasone to the patient. In one embodiment, the method additionally comprises administration of bortezomib to the patient.

In one embodiment, the second active agent used in the methods provided herein is a DNA methyltransferase inhibitor. In one embodiment, the DNA methyltransferase inhibitor is azacitidine, or a stereoisomer, mixture of stereoisomers, tautomer, isotopolog, or pharmaceutically acceptable salt thereof. In one embodiment, the DNA methyltransferase inhibitor is azacitidine. In one embodiment, provided herein is a method of treating multiple myeloma, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is azacitidine, or a stereoisomer, mixture of stereoisomers, tautomer, isotopolog, or pharmaceutically acceptable salt thereof. In one embodiment, provided herein is a method of treating multiple myeloma, which comprises administering to a patient a therapeutically effective amount of Compound 2 in combination with a second active agent, wherein the second active agent is azacitidine. In one embodiment, the method additionally comprises administration of dexamethasone to the patient. In one embodiment, the method additionally comprises administration of bortezomib to the patient.

Also provided herein are methods of treating patients who have been previously treated for multiple myeloma but are non-responsive to standard therapies, as well as those who have not previously been treated. Further encompassed are methods of treating patients who have undergone surgery in an attempt to treat multiple myeloma, as well as those who have not. Also provided herein are methods of treating patients who have been previously undergone transplant therapy, as well as those who have not.

The methods provided herein include treatment of multiple myeloma that is relapsed, refractory or resistant. The methods provided herein include prevention of multiple myeloma that is relapsed, refractory or resistant. The methods provided herein include management of multiple myeloma that is relapsed, refractory or resistant. In some such embodiments, the myeloma is primary, secondary, tertiary, quadruply or quintuply relapsed multiple myeloma. In one embodiment, the methods provided herein reduce, maintain or eliminate minimal residual disease (MRD). In one embodiment, provided herein is a method of increasing rate and/or durability of MRD negativity in multiple myeloma patients, comprising administering a therapeutically effective amount of Compound 1, or an enantiomer, mixture of enantiomers, tautomer, isotopolog, or pharmaceutically acceptable salt thereof, in combination with a second active agent provided herein. In one embodiment, provided herein is a method of increasing rate and/or durability of MRD negativity in multiple myeloma patients, comprising administering a therapeutically effective amount of Compound 2, or a tautomer, isotopolog, or pharmaceutically acceptable salt thereof, in combination with a second active agent provided herein. In one embodiment, methods provided herein encompass treating, preventing or managing various types of multiple myeloma, such as monoclonal gammopathy of undetermined significance (MGUS), low risk, intermediate risk, and high risk multiple myeloma, newly diagnosed multiple myeloma (including low risk, intermediate risk, and high risk newly diagnosed multiple myeloma), transplant eligible and transplant ineligible multiple myeloma, smoldering (indolent) multiple myeloma (including low risk, intermediate risk, and high risk smouldering multiple myeloma), active multiple myeloma, solitary plasmacytoma, extramedullary plasmacytoma, plasma cell leukemia, central nervous system multiple myeloma, light chain myeloma, non-secretory myeloma, Immunoglobulin D myeloma, and Immunoglobulin E myeloma, by administering a therapeutically effective amount of a compound described herein. In another embodiment, methods provided herein encompass treating, preventing or managing multiple myeloma characterized by genetic abnormalities, such as Cyclin D translocations (for example, t(11;14)(q13; q32); t(6;14)(p21;32); t(12; 14)(p13;q32); or t(6;20); MMSET translocations (for example, t(4; 14)(p16;q32)); MAF translocations (for example, t(14; 16)(q32;q32); t(20; 22); t(16; 22)(q11;q13); or t(14;20)(q32;q11)); or other chromosome factors (for example, deletion of 17p13, or chromosome 13; del(17/17p), nonhyperdiploidy, and gain (1q)), by administering a therapeutically effective amount of a compound described herein. In one embodiment, the multiple myeloma is characterized according to the multiple myeloma International Staging System (ISS). In one embodiment, the multiple myeloma is Stage I multiple myeloma as characterized by ISS (e.g., serum β2 microglobulin <3.5 mg/L and serum albumin ≥3.5 g/dL). In one embodiment, the multiple myeloma is Stage III multiple myeloma as characterized by ISS (e.g., serum β2 microglobulin >5.4 mg/L). In one embodiment, the multiple myeloma is Stage II multiple myeloma as characterized by ISS (e.g., not Stage I or III).

In one embodiment, the methods comprise administering a therapeutically effective amount of Compound 1, or an enantiomer, mixture of enantiomers, tautomer, isotopolog, or pharmaceutically acceptable salt thereof, in combination with a second active agent provided herein. In another embodiment, the methods comprise administering a therapeutically effective amount of Compound 2, or a tautomer, isotopolog, or pharmaceutically acceptable salt thereof, in combination with a second active agent provided herein. In another embodiment, the methods comprise administering a therapeutically effective amount of Compound 3, or a tautomer, isotopolog, or pharmaceutically acceptable salt thereof, in combination with a second active agent provided herein.

In some embodiments, the methods comprise administering a therapeutically effective amount of Compound 1, or an enantiomer, mixture of enantiomers, tautomer, isotopolog, or pharmaceutically acceptable salt thereof, in combination with a second active agent provided herein as induction therapy. In another embodiment, the methods comprise administering a therapeutically effective amount of Compound 2, or a tautomer, isotopolog, or pharmaceutically acceptable salt thereof, in combination with a second active agent provided herein as induction therapy. In another embodiment, the methods comprise administering a therapeutically effective amount of Compound 3, or a tautomer, isotopolog, or pharmaceutically acceptable salt thereof, in combination with a second active agent provided herein as induction therapy. In some embodiments, the methods comprise administering a therapeutically effective amount of Compound 1, or an enantiomer, mixture of enantiomers, tautomer, isotopolog, or pharmaceutically acceptable salt thereof, in combination with a second active agent provided herein as consolidation therapy. In another embodiment, the methods comprise administering a therapeutically effective amount of Compound 2, or a tautomer, isotopolog, or pharmaceutically acceptable salt thereof, in combination with a second active agent provided herein as consolidation therapy. In another embodiment, the methods comprise administering a therapeutically effective amount of Compound 3, or a tautomer, isotopolog, or pharmaceutically acceptable salt thereof, in combination with a second active agent provided herein as consolidation therapy. In some embodiments, the methods comprise administering a therapeutically effective amount of Compound 1, or an enantiomer, mixture of enantiomers, tautomer, isotopolog, or pharmaceutically acceptable salt thereof, in combination with a second active agent provided herein as maintenance therapy. In another embodiment, the methods comprise administering a therapeutically effective amount of Compound 2, or a tautomer, isotopolog, or pharmaceutically acceptable salt thereof, in combination with a second active agent provided herein as maintenance therapy. In another embodiment, the methods comprise administering a therapeutically effective amount of Compound 3, or a tautomer, isotopolog, or pharmaceutically acceptable salt thereof, in combination with a second active agent provided herein as maintenance therapy.

In one particular embodiment of the methods described herein, the multiple myeloma is plasma cell leukemia.

In one embodiment of the methods described herein, the multiple myeloma is high risk multiple myeloma. In some such embodiments, the high risk multiple myeloma is relapsed or refractory. In one embodiment, the high risk multiple myeloma is multiple myeloma that is relapsed within 12 months of first treatment. In yet another embodiment, the high risk multiple myeloma is multiple myeloma that is characterized by genetic abnormalities, for example, one or more of del(17/17p) and t(14;16)(q32;q32). In some such embodiments, the high risk multiple myeloma is relapsed or refractory to one, two or three previous treatments.

In one embodiment, the multiple myeloma is characterized by a p53 mutation. In one embodiment, the p53 mutation is a Q331 mutation. In one embodiment, the p53 mutation is an R273H mutation. In one embodiment, the p53 mutation is a K132 mutation. In one embodiment, the p53 mutation is a K132N mutation. In one embodiment, the p53 mutation is an R337 mutation. In one embodiment, the p53 mutation is an R337L mutation. In one embodiment, the p53 mutation is a W146 mutation. In one embodiment, the p53 mutation is an S261 mutation. In one embodiment, the p53 mutation is an S261T mutation. In one embodiment, the p53 mutation is an E286 mutation. In one embodiment, the p53 mutation is an E286K mutation. In one embodiment, the p53 mutation is an R175 mutation. In one embodiment, the p53 mutation is an R175H mutation. In one embodiment, the p53 mutation is an E258 mutation. In one embodiment, the p53 mutation is an E258K mutation. In one embodiment, the p53 mutation is an A161 mutation. In one embodiment, the p53 mutation is an A161T mutation.

In one embodiment, the multiple myeloma is characterized by homozygous deletion of p53. In one embodiment, the multiple myeloma is characterized by homozygous deletion of wild type p53.

In one embodiment, the multiple myeloma is characterized by wild type p53.

In one embodiment, the multiple myeloma is characterized by activation of one or more oncogenic drivers. In one embodiment, the one or more oncogenic drivers are selected from the group consisting of C-MAF, MAFB, FGFR3, MMset, Cyclin D1, and Cyclin D. In one embodiment, the multiple myeloma is characterized by activation of C-MAF. In one embodiment, the multiple myeloma is characterized by activation of MAFB. In one embodiment, the multiple myeloma is characterized by activation of FGFR3 and MMset. In one embodiment, the multiple myeloma is characterized by activation of C-MAF, FGFR3, and MMset. In one embodiment, the multiple myeloma is characterized by activation of Cyclin D1. In one embodiment, the multiple myeloma is characterized by activation of MAFB and Cyclin D1. In one embodiment, the multiple myeloma is characterized by activation of Cyclin D.

In one embodiment, the multiple myeloma is characterized by one or more chromosomal translocations. In one embodiment, the chromosomal translocation is t(14; 16). In one embodiment, the chromosomal translocation is t(14;20). In one embodiment, the chromosomal translocation is t(4; 14). In one embodiment, the chromosomal translocations are t(4;14) and t(14;16). In one embodiment, the chromosomal translocation is t(11;14). In one embodiment, the chromosomal translocation is t(6;20). In one embodiment, the chromosomal translocation is t(20;22). In one embodiment, the chromosomal translocations are t(6;20) and t(20;22). In one embodiment, the chromosomal translocation is t(16;22). In one embodiment, the chromosomal translocations are t(14; 16) and t(16;22). In one embodiment, the chromosomal translocations are t(14;20) and t(11;14).

In one embodiment, the multiple myeloma is characterized by a Q331 p53 mutation, by activation of C-MAF, and by a chromosomal translocation at t(14; 16). In one embodiment, the multiple myeloma is characterized by homozygous deletion of p53, by activation of C-MAF, and by a chromosomal translocation at t(14; 16). In one embodiment, the multiple myeloma is characterized by a K132N p53 mutation, by activation of MAFB, and by a chromosomal translocation at t(14;20). In one embodiment, the multiple myeloma is characterized by wild type p53, by activation of FGFR3 and MMset, and by a chromosomal translocation at t(4; 14). In one embodiment, the multiple myeloma is characterized by wild type p53, by activation of C-MAF, and by a chromosomal translocation at t(14;16). In one embodiment, the multiple myeloma is characterized by homozygous deletion of p53, by activation of FGFR3, MMset, and C-MAF, and by chromosomal translocations at t(4; 14) and t(14; 16). In one embodiment, the multiple myeloma is characterized by homozygous deletion of p53, by activation of Cyclin D1, and by a chromosomal translocation at t(11; 14). In one embodiment, the multiple myeloma is characterized by an R337L p53 mutation, by activation of Cyclin D1, and by a chromosomal translocation at t(11;14). In one embodiment, the multiple myeloma is characterized by a W146 p53 mutation, by activation of FGFR3 and MMset, and by a chromosomal translocation at t(4; 14). In one embodiment, the multiple myeloma is characterized by an S261T p53 mutation, by activation of MAFB, and by chromosomal translocations at t(6;20) and t(20;22). In one embodiment, the multiple myeloma is characterized by an E286K p53 mutation, by activation of FGFR3 and MMset, and by a chromosomal translocation at t(4; 14). In one embodiment, the multiple myeloma is characterized by an R175H p53 mutation, by activation of FGFR3 and MMset, and by a chromosomal translocation at t(4; 14). In one embodiment, the multiple myeloma is characterized by an E258K p53 mutation, by activation of C-MAF, and by chromosomal translocations at t(14;16) and t(16;22). In one embodiment, the multiple myeloma is characterized by wild type p53, by activation of MAFB and Cyclin D1, and by chromosomal translocations at t(14;20) and t(11;14). In one embodiment, the multiple myeloma is characterized by an A161T p53 mutation, by activation of Cyclin D, and by a chromosomal translocation at t(11;14).

In some embodiments of the methods described herein, the multiple myeloma is transplant eligible newly diagnosed multiple myeloma. In another embodiment, the multiple myeloma is transplant ineligible newly diagnosed multiple myeloma.

In yet other embodiments, the multiple myeloma is characterized by early progression (for example less than 12 months) following initial treatment. In still other embodiments, the multiple myeloma is characterized by early progression (for example less than 12 months) following autologous stem cell transplant. In another embodiment, the multiple myeloma is refractory to lenalidomide. In another embodiment, the multiple myeloma is refractory to pomalidomide. In some such embodiments, the multiple myeloma is predicted to be refractory to pomalidomide (for example, by molecular characterization). In another embodiment, the multiple myeloma is relapsed or refractory to 3 or more treatments and was exposed to a proteasome inhibitor (for example, bortezomib, carfilzomib, ixazomib, oprozomib, or marizomib) and an immunomodulatory compound (for example thalidomide, lenalidomide, pomalidomide, iberdomide, or avadomide), or double refractory to a proteasome inhibitor and an immunomodulatory compound. In still other embodiments, the multiple myeloma is relapsed or refractory to 3 or more prior therapies, including for example, a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide) or double refractory to a proteasome inhibitor or immunomodulatory compound and a CD38 mAb. In still other embodiments, the multiple myeloma is triple refractory, for example, the multiple myeloma is refractory to a proteasome inhibitor (for example, bortezomib, carfilzomib, ixazomib, oprozomib or marizomib), an immunomodulatory compound (for example thalidomide, lenalidomide, pomalidomide, iberdomide, or avadomide), and one other active agent, as described herein.

In certain embodiments, provided herein are methods of treating, preventing, and/or managing multiple myeloma, including relapsed/refractory multiple myeloma in patients with impaired renal function or a symptom thereof, comprising administering a therapeutically effective amount of Compound 1, Compound 2 or Compound 3, or an enantiomer, mixture of enantiomers, tautomer, isotopolog, or pharmaceutically acceptable salt thereof, in combination with a second active agent provided herein, to a patient having relapsed/refractory multiple myeloma with impaired renal function.

In certain embodiments, provided herein are methods of treating, preventing, and/or managing multiple myeloma, including relapsed or refractory multiple myeloma in frail patients or a symptom thereof, comprising administering a therapeutically effective amount of Compound 1, Compound 2 or Compound 3, or an enantiomer, mixture of enantiomers, tautomer, isotopolog, or pharmaceutically acceptable salt thereof, in combination with a second active agent provided herein, to a frail patient having multiple myeloma. In some such embodiments, the frail patient is characterized by ineligibility for induction therapy, or intolerance to dexamethasone treatment. In some such embodiment the frail patient is elderly, for example, older than 65 years old.

In certain embodiments, provided herein are methods of treating, preventing or managing multiple myeloma, comprising administering to a patient a therapeutically effective amount of Compound 1, or a tautomer, isotopolog, or pharmaceutically acceptable salt thereof, in combination with a second active agent provided herein, wherein the multiple myeloma is fourth line relapsed/refractory multiple myeloma. In certain embodiments, provided herein are methods of treating, preventing or managing multiple myeloma, comprising administering to a patient a therapeutically effective amount of Compound 2, or a tautomer, isotopolog, or pharmaceutically acceptable salt thereof, in combination with a second active agent provided herein, wherein the multiple myeloma is fourth line relapsed/refractory multiple myeloma. In certain embodiments, provided herein are methods of treating, preventing or managing multiple myeloma, comprising administering to a patient a therapeutically effective amount of Compound 3, or a tautomer, isotopolog, or pharmaceutically acceptable salt thereof, in combination with a second active agent provided herein, wherein the multiple myeloma is fourth line relapsed/refractory multiple myeloma.

In certain embodiments, provided herein are methods of treating, preventing or managing multiple myeloma, comprising administering to a patient a therapeutically effective amount of Compound 1, or a tautomer, isotopolog, or pharmaceutically acceptable salt thereof, in combination with a second active agent provided herein, as induction therapy, wherein the multiple myeloma is newly diagnosed, transplant-eligible multiple myeloma. In certain embodiments, provided herein are methods of treating, preventing or managing multiple myeloma, comprising administering to a patient a therapeutically effective amount of Compound 2, or a tautomer, isotopolog, or pharmaceutically acceptable salt thereof, in combination with a second active agent provided herein, as induction therapy, wherein the multiple myeloma is newly diagnosed, transplant-eligible multiple myeloma. In certain embodiments, provided herein are methods of treating, preventing or managing multiple myeloma, comprising administering to a patient a therapeutically effective amount of Compound 3, or a tautomer, isotopolog, or pharmaceutically acceptable salt thereof, in combination with a second active agent provided herein, as induction therapy, wherein the multiple myeloma is newly diagnosed, transplant-eligible multiple myeloma.

In certain embodiments, provided herein are methods of treating, preventing or managing multiple myeloma, comprising administering to a patient a therapeutically effective amount of Compound 1, or a tautomer, isotopolog, or pharmaceutically acceptable salt thereof, in combination with a second active agent provided herein, as maintenance therapy after other therapy or transplant, wherein the multiple myeloma is newly diagnosed, transplant-eligible multiple myeloma prior to the other therapy or transplant. In certain embodiments, provided herein are methods of treating, preventing or managing multiple myeloma, comprising administering to a patient a therapeutically effective amount of Compound 2, or a tautomer, isotopolog, or pharmaceutically acceptable salt thereof, in combination with a second active agent provided herein, as maintenance therapy after other therapy or transplant, wherein the multiple myeloma is newly diagnosed, transplant-eligible multiple myeloma prior to the other therapy or transplant. In certain embodiments, provided herein are methods of treating, preventing or managing multiple myeloma, comprising administering to a patient a therapeutically effective amount of Compound 3, or a tautomer, isotopolog, or pharmaceutically acceptable salt thereof, in combination with a second active agent provided herein, as maintenance therapy after other therapy or transplant, wherein the multiple myeloma is newly diagnosed, transplant-eligible multiple myeloma prior to the other therapy or transplant.

In certain embodiments, provided herein are methods of treating, preventing or managing multiple myeloma, comprising administering to a patient a therapeutically effective amount of Compound 1, or a tautomer, isotopolog, or pharmaceutically acceptable salt thereof, in combination with a second active agent provided herein, as maintenance therapy after other therapy or transplant. In some embodiments, the multiple myeloma is newly diagnosed, transplant-eligible multiple myeloma prior to the other therapy and/or transplant. In some embodiments, the other therapy prior to transplant is treatment with chemotherapy or Compound 1, Compound 2 or Compound 3. In certain embodiments, provided herein are methods of treating, preventing or managing multiple myeloma, comprising administering to a patient a therapeutically effective amount of Compound 2, or a tautomer, isotopolog, or pharmaceutically acceptable salt thereof, in combination with a second active agent provided herein, as maintenance therapy after other therapy or transplant. In some embodiments, the multiple myeloma is newly diagnosed, transplant-eligible multiple myeloma prior to the other therapy and/or transplant. In some embodiments, the other therapy prior to transplant is treatment with chemotherapy or Compound 1, Compound 2 or Compound 3. In certain embodiments, provided herein are methods of treating, preventing or managing multiple myeloma, comprising administering to a patient a therapeutically effective amount of Compound 3, or a tautomer, isotopolog, or pharmaceutically acceptable salt thereof, in combination with a second active agent provided herein, as maintenance therapy after other therapy or transplant. In some embodiments, the multiple myeloma is newly diagnosed, transplant-eligible multiple myeloma prior to the other therapy and/or transplant. In some embodiments, the other therapy prior to transplant is treatment with chemotherapy or Compound 1, Compound 2 or Compound 3.

In certain embodiments, provided herein are methods of treating, preventing or managing multiple myeloma, comprising administering to a patient a therapeutically effective amount of Compound 1, or a tautomer, isotopolog, or pharmaceutically acceptable salt thereof, in combination with a second active agent provided herein, wherein the multiple myeloma is high risk multiple myeloma, that is relapsed or refractory to one, two or three previous treatments. In certain embodiments, provided herein are methods of treating, preventing or managing multiple myeloma, comprising administering to a patient a therapeutically effective amount of Compound 2, or a tautomer, isotopolog, or pharmaceutically acceptable salt thereof, in combination with a second active agent provided herein, wherein the multiple myeloma is high risk multiple myeloma, that is relapsed or refractory to one, two or three previous treatments. In certain embodiments, provided herein are methods of treating, preventing or managing multiple myeloma, comprising administering to a patient a therapeutically effective amount of Compound 3, or a tautomer, isotopolog, or pharmaceutically acceptable salt thereof, in combination with a second active agent provided herein, wherein the multiple myeloma is high risk multiple myeloma, that is relapsed or refractory to one, two or three previous treatments.

In certain embodiments, provided herein are methods of treating, preventing or managing multiple myeloma, comprising administering to a patient a therapeutically effective amount of Compound 1, or a tautomer, isotopolog, or pharmaceutically acceptable salt thereof, in combination with a second active agent provided herein, wherein the multiple myeloma is newly diagnosed, transplant-ineligible multiple myeloma. In certain embodiments, provided herein are methods of treating, preventing or managing multiple myeloma, comprising administering to a patient a therapeutically effective amount of Compound 2, or a tautomer, isotopolog, or pharmaceutically acceptable salt thereof, in combination with a second active agent provided herein, wherein the multiple myeloma is newly diagnosed, transplant-ineligible multiple myeloma. In certain embodiments, provided herein are methods of treating, preventing or managing multiple myeloma, comprising administering to a patient a therapeutically effective amount of Compound 3, or a tautomer, isotopolog, or pharmaceutically acceptable salt thereof, in combination with a second active agent provided herein, wherein the multiple myeloma is newly diagnosed, transplant-ineligible multiple myeloma.

In certain embodiments, the patient to be treated with one of the methods provided herein has not been treated with multiple myeloma therapy prior to the administration of Compound 1, Compound 2 or Compound 3, or an enantiomer, mixture of enantiomers, tautomer, isotopolog, or pharmaceutically acceptable salt thereof, in combination with a second active agent provided herein. In certain embodiments, the patient to be treated with one of the methods provided herein has been treated with multiple myeloma therapy prior to the administration of Compound 1, Compound 2 or Compound 3, or an enantiomer, mixture of enantiomers, tautomer, isotopolog, or pharmaceutically acceptable salt thereof, in combination with a second active agent provided herein. In certain embodiments, the patient to be treated with one of the methods provided herein has developed drug resistance to the anti-multiple myeloma therapy. In some such embodiments, the patient has developed resistance to one, two, or three anti-multiple myeloma therapies, wherein the therapies are selected from a CD38 monoclonal antibody (CD38 mAb, for example, daratumumab or isatuximab), a proteasome inhibitor (for example, bortezomib, carfilzomib, ixazomib, or marizomib), and an immunomodulatory compound (for example thalidomide, lenalidomide, pomalidomide, iberdomide, or avadomide).

The methods provided herein encompass treating a patient regardless of patient's age. In some embodiments, the subject is 18 years or older. In other embodiments, the subject is more than 18, 25, 35, 40, 45, 50, 55, 60, 65, or 70 years old. In other embodiments, the subject is less than 65 years old. In other embodiments, the subject is more than 65 years old. In one embodiment, the subject is an elderly multiple myeloma subject, such as a subject older than 65 years old. In one embodiment, the subject is an elderly multiple myeloma subject, such as a subject older than 75 years old.

G. Dosing of Compound 1, Compound 2 or Compound 3

In certain embodiments, a therapeutically or prophylactically effective amount of Compound 1, Compound 2 or Compound 3 is from about 0.01 to about 25 mg per day, from about 0.01 to about 10 mg per day, from about 0.01 to about 5 mg per day, from about 0.01 to about 2 mg per day, from about 0.01 to about 1 mg per day, from about 0.01 to about 0.5 mg per day, from about 0.01 to about 0.25 mg per day, from about 0.1 to about 25 mg per day, from about 0.1 to about 10 mg per day, from about 0.1 to about 5 mg per day, from about 0.1 to about 2 mg per day, from about 0.1 to about 1 mg per day, from about 0.1 to about 0.5 mg per day, from about 0.1 to about 0.25 mg per day, from about 0.5 to about 25 mg per day, from about 0.5 to about 10 mg per day, from about 0.5 to about 5 mg per day, from about 0.5 to about 2 mg per day, from about 0.5 to about 1 mg per day, from about 1 to about 25 mg per day, from about 1 to about 10 mg per day, from about 1 to about 5 mg per day, from about 1 to about 2.5 mg per day, or from about 1 to about 2 mg per day. In one embodiment, a therapeutically or prophylactically effective amount of Compound 1, Compound 2 or Compound 3 is from about 0.1 mg per day to about 0.4 mg per day.

In certain embodiments, the therapeutically or prophylactically effective amount of Compound 1, Compound 2 or Compound 3 is about 0.1, about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 15, about 20, or about 25 mg per day. In some such embodiments, the therapeutically or prophylactically effective amount is about 0.1, about 0.2, about 0.3, about 0.4, about 0.5, about 0.6 or about 0.7 mg per day.

In one embodiment, the recommended daily dose range of Compound 1, Compound 2, or Compound 3 for the conditions described herein lie within the range of from about 0.1 mg to about 25 mg per day, preferably given as a single once-a-day dose, or in divided doses throughout a day. In other embodiments, the dosage ranges from about 0.1 to about 10 mg per day. Specific doses per day include 0.1, 0.2, 0.3, 0.4, 0.5, 1, 2, 3, 4, 5, 6, 7, 8, 9, 10, 11, 12, 13, 14, 15, 16, 17, 18, 19, 20, 21, 22, 23, 24, or 25 mg per day. More specific doses per day include 0.1, 0.2, 0.3, 0.4, or 0.5 mg per day.

In a specific embodiment, the recommended starting dosage of Compound 1, Compound 2, or Compound 3 may be 0.1, 0.2, 0.3, 0.4, 0.5, 1, 2, 3, 4, 5, 10, 15, 20, or 25 mg per day. In another embodiment, the recommended starting dosage may be 0.1, 0.2, 0.3, 0.4, or 0.5, mg per day. The dose may be escalated to 1, 2, 3, 4, or 5 mg per day.

In certain embodiments, the therapeutically or prophylactically effective amount of Compound 1, Compound 2, or Compound 3 is from about 0.001 to about 5 mg/kg/day, from about 0.001 to about 4 mg/kg/day, from about 0.001 to about 3 mg/kg/day, from about 0.001 to about 2 mg/kg/day, from about 0.001 to about 1 mg/kg/day, from about 0.001 to about 0.05 mg/kg/day, from about 0.001 to about 0.04 mg/kg/day, from about 0.001 to about 0.03 mg/kg/day, from about 0.001 to about 0.02 mg/kg/day, from about 0.001 to about 0.01 mg/kg/day, or from about 0.001 to about 0.005 mg/kg/day.

The administered dose can also be expressed in units other than mg/kg/day. For example, doses for parenteral administration can be expressed as mg/m$^2$/day. One of ordinary skill in the art would readily know how to convert doses from mg/kg/day to mg/m$^2$/day given either the height or weight of a subject or both (see, www.fda.gov/cder/cancer/animalframe.htm). For example, a dose of 1 mg/kg/day for a 65 kg human is approximately equal to 38 mg/m$^2$/day.

Depending on the state of the disease to be treated and the subject's condition, Compound 1, Compound 2, or Compound 3 provided herein, or an enantiomer, mixture of enantiomers, tautomer, isotopolog, or pharmaceutically acceptable salt thereof, may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. Compound 1, Compound 2 or Compound 3 provided herein, or an enantiomer, mixture of enantiomers, tautomer, isotopolog, or pharmaceutically acceptable salt thereof, may be formulated, alone or together, in suitable dosage unit with pharmaceutically acceptable excipients, carriers, adjuvants and vehicles, appropriate for each route of administration.

In one embodiment, Compound 1, Compound 2 or Compound 3 provided herein, or an enantiomer, mixture of enantiomers, tautomer, isotopolog, or pharmaceutically acceptable salt thereof, is administered orally. In another embodiment, the compound of Compound 1, Compound 2 or Compound 3 provided herein, or an enantiomer, mixture of enantiomers, tautomer, isotopolog, or pharmaceutically acceptable salt thereof, is administered parenterally. In yet another embodiment, the compound of Compound 1, Compound 2 or Compound 3 provided herein, or an enantiomer, mixture of enantiomers, tautomer, isotopolog, or pharmaceutically acceptable salt thereof, is administered intravenously.

Compound 1, Compound 2 or Compound 3 provided herein, or an enantiomer, mixture of enantiomers, tautomer, isotopolog, or pharmaceutically acceptable salt thereof, can be delivered as a single dose such as, e.g., a single bolus injection, or oral tablets or pills; or over time, such as, e.g., continuous infusion over time or divided bolus doses over time. The compounds as described herein can be administered repeatedly if necessary, for example, until the patient experiences stable disease or regression, or until the patient experiences disease progression or unacceptable toxicity. Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

Compound 1, Compound 2 or Compound 3 provided herein, or an enantiomer, mixture of enantiomers, tautomer, isotopolog, or pharmaceutically acceptable salt thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered once or more than once each day, for example, for a period of time. The term "continuous" is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered daily for an uninterrupted period of at least 7 days to 52 weeks. The term "intermittent" or "intermittently" as used herein is intended to mean stopping and starting at either regular or irregular intervals. For example, intermittent administration of Compound 1, Compound 2 or Compound 3 provided herein, or an enantiomer, mixture of enantiomers, tautomer, isotopolog, or pharmaceutically acceptable salt thereof, is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as Compound 1, Compound 2 or Compound 3 provided herein, or an enantiomer, mixture of enantiomers, tautomer, isotopolog, or pharmaceutically acceptable salt thereof, is administered daily or continuously but with a rest period. In some such embodiments, administration is once a day for two to six days, then a rest period with no administration for five to seven days.

In some embodiments, the frequency of administration of Compound 1, Compound 2, or Compound 3 is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, Compound 1, Compound 2 or Compound 3 provided herein, or an enantiomer, mixture of enantiomers, tautomer, isotopolog, or pharmaceutically acceptable salt thereof, is administered once a day. In another embodiment, Compound 1, Compound 2 or Compound 3 provided herein, or an enantiomer, mixture of enantiomers, tautomer, isotopolog, or pharmaceutically acceptable salt thereof, is administered twice a day. In yet another embodiment, Compound 1, Compound 2 or Compound 3 provided herein, or an enantiomer, mixture of enantiomers, tautomer, isotopolog, or pharmaceutically acceptable salt thereof, is administered three times a day. In still another embodiment, Compound 1, Compound 2 or Compound 3 provided herein, or an enantiomer, mixture of enantiomers, tautomer, isotopolog, or pharmaceutically acceptable salt thereof, is administered four times a day.

In one embodiment, a therapeutically effective amount of Compound 1, Compound 2 or Compound 3 is administered in a treatment cycle which includes an administration period of up to 21 days followed by a rest period. In one embodiment, a therapeutically effective amount of Compound 1, Compound 2 or Compound 3 is administered in a treatment cycle which includes an administration period of up to 20 days followed by a rest period. In one embodiment, a therapeutically effective amount of Compound 1, Compound 2 or Compound 3 is administered in a treatment cycle which includes an administration period of up to 15 days followed by a rest period. In one embodiment, a therapeutically effective amount of Compound 1, Compound 2 or Compound 3 is administered in a treatment cycle which includes an administration period of up to 10 days followed by a rest period. In one embodiment, a therapeutically effective amount of Compound 1, Compound 2 or Compound 3 is administered in a treatment cycle which includes an administration period of up to 7 days followed by a rest period. In one embodiment, a therapeutically effective amount of Compound 1, Compound 2 or Compound 3 is administered in a treatment cycle which includes an administration period of up to 5 days followed by a rest period. In one embodiment, a therapeutically effective amount of Compound 1, Compound 2 or Compound 3 is administered in a treatment cycle which includes an administration period of up to 4 days followed by a rest period. In one embodiment, a therapeutically effective amount of Compound 1, Compound 2 or Compound 3 is administered in a treatment cycle which includes an administration period of up to 3 days followed by a rest period.

In one embodiment, the treatment cycle with Compound 1, Compound 2 or Compound 3 includes an administration period of up to 14 days followed by a rest period. In one embodiment, the treatment cycle includes an administration period of up to 10 days followed by a rest period. In one embodiment, the treatment cycle includes an administration period of up to 7 days followed by a rest period. In one embodiment, the treatment cycle includes an administration period of up to 5 days followed by a rest period. In one embodiment, the treatment cycle includes an administration period of up to 4 days followed by a rest period. In one embodiment, the treatment cycle includes an administration period of up to 3 days followed by a rest period.

In one embodiment, the rest period is from about 2 days up to about 11 days. In one embodiment, the rest period is from about 2 days up to about 10 days. In one embodiment, the rest period is about 2 days. In one embodiment, the rest period is about 3 days. In one embodiment, the rest period is about 4 days. In one embodiment, the rest period is about 5 days. In one embodiment, the rest period is about 6 days. In another embodiment, the rest period is about 7 days. In another embodiment, the rest period is about 8 days. In another embodiment, the rest period is about 9 days. In another embodiment, the rest period is about 10 days. In another embodiment, the rest period is about 11 days.

In one embodiment, the treatment cycle with Compound 1, Compound 2 or Compound 3 includes an administration period of up to 15 days followed by a rest period from about 2 days up to about 10 days. In one embodiment, the treatment cycle includes an administration period of up to 10 days followed by a rest period from about 2 days up to about 10 days. In one embodiment, the treatment cycle includes an administration period of up to 7 days followed by a rest period from about 2 days up to about 10 days. In one embodiment, the treatment cycle includes an administration period of up to 5 days followed by a rest period from about 2 days up to about 10 days. In one embodiment, the treatment cycle includes an administration period of up to 3 days followed by a rest period from about 10 days up to about 15 days. In one embodiment, the treatment cycle includes an administration period of up to 3 days followed by a rest period from about 3 days up to about 15 days.

In one embodiment, the treatment cycle with Compound 1, Compound 2 or Compound 3 includes an administration period of up to 15 days followed by a rest period of 7 days. In one embodiment, the treatment cycle includes an administration period of up to 10 days followed by a rest period of 5 days. In one embodiment, the treatment cycle includes an administration period of up to 10 days followed by a rest period of 4 days. In one embodiment, the treatment cycle includes an administration period of up to 10 days followed by a rest period of 3 days. In one embodiment, the treatment cycle includes an administration period of up to 10 days followed by a rest period of 2 days. In one embodiment, the treatment cycle includes an administration period of up to 7 days followed by a rest period of 7 days. In one embodiment, the treatment cycle includes an administration period of up to 5 days followed by a rest period of 5 days. In one embodiment, the treatment cycle includes an administration period of up to 3 days followed by a rest period of 11 days.

In another embodiment, the treatment cycle includes an administration period of up to 5 days followed by a rest period of 9 days. In another embodiment, the treatment cycle includes an administration period of up to 5 days followed by a rest period of 2 days. In another embodiment, the treatment cycle includes an administration period of up to 3 days followed by a rest period of 4 days.

In one embodiment, the treatment cycle with Compound 1, Compound 2 or Compound 3 includes an administration of a therapeutically effective amount of Compound 1, Compound 2 or Compound 3 on days 1 to 5 of a 28 day cycle. In another embodiment, the treatment cycle includes an administration of Compound 1, Compound 2 or Compound 3 on days 1 to 10 of a 28 day cycle. In one embodiment, the treatment cycle includes an administration of a therapeutically effective amount of Compound 1, Compound 2 or Compound 3 on days 1 to 21 of a 28 day cycle. In another embodiment, the treatment cycle includes an administration of a therapeutically effective amount of Compound 1, Compound 2 or Compound 3 on days 1 to 5 of a 7 day cycle. In another embodiment, the treatment cycle includes an administration of a therapeutically effective amount of Compound 1, Compound 2 or Compound 3 on days 1 to 7 of a 7 day cycle. In one embodiment, the treatment cycle includes an administration of a therapeutically effective amount of Compound 1, Compound 2 or Compound 3 on days 1 to 10 and days 15 to 24 of a 28 day cycle (herein referred to as 20/28 dosing cycle). In one embodiment, the treatment cycle includes an administration of a therapeutically effective amount of Compound 1, Compound 2 or Compound 3 on days 1 to 3 and days 15 to 18 of a 28 day cycle. In one embodiment, the treatment cycle includes an administration of a therapeutically effective amount of Compound 1, Compound 2 or Compound 3 on days 1 to 7 and days 15 to 21 of a 28 day cycle (herein referred to as 14/28 dosing cycle). In one embodiment, the treatment cycle includes an administration of a therapeutically effective amount of Compound 1, Compound 2 or Compound 3 on days 1 to 5 and days 15 to 19 of a 28 day cycle (herein referred to as 10/28 dosing cycle). In one embodiment, the treatment cycle includes an administration of a therapeutically effective amount of Compound 1, Compound 2 or Compound 3 on days 1 to 3 and days 15 to 17 of a 28 day cycle (herein referred to as 6/28 dosing cycle).

In one embodiment, the treatment cycle with Compound 1, Compound 2 or Compound 3 includes an administration of a therapeutically effective amount of Compound 1, Compound 2 or Compound 3 on days 1 to 14 of a 21 day cycle. In another embodiment, the treatment cycle includes an administration of Compound 1, Compound 2 or Compound 3 on days 1 to 4 and 8 to 11 of a 21 day cycle. In one embodiment, the treatment cycle includes an administration of a therapeutically effective amount of Compound 1, Compound 2 or Compound 3 on days 1 to 5 and 8 to 12 of a 21 day cycle. In another embodiment, the treatment cycle includes an administration of a therapeutically effective amount of Compound 1, Compound 2 or Compound 3 on days 1 to 5 and 11 to 15 of a 21 day cycle. In another embodiment, the treatment cycle includes an administration of a therapeutically effective amount of Compound 1, Compound 2 or Compound 3 on days 1 to 5, 8 to 12 and 15 to 19 of a 21 day cycle. In another embodiment, the treatment cycle includes an administration of a therapeutically effective amount of Compound 1, Compound 2 or Compound 3 on days 1 to 4, 8 to 11 and 15 to 18 of a 21 day cycle. In another embodiment, the treatment cycle includes an administration of a therapeutically effective amount of Compound 1, Compound 2 or Compound 3 on days 1 to 4, 8 to 10 and 15 to 17 of a 21 day cycle. In another embodiment, the treatment cycle includes an administration of a therapeutically effective amount of Compound 1, Compound 2 or Compound 3 on days 1 to 3, and 8 to 11 of a 21 day cycle. In another embodiment, the treatment cycle includes an administration of a therapeutically effective amount of Compound 1, Compound 2 or Compound 3 on days 1 to 3 and 11 to 13 of a 21 day cycle.

Any treatment cycle described herein can be repeated for at least 2, 3, 4, 5, 6, 7, 8, or more cycles. In certain instances, the treatment cycle as described herein includes from 1 to about 24 cycles, from about 2 to about 16 cycles, or from about 2 to about 4 cycles. In certain instances a treatment cycle as described herein includes from 1 to about 4 cycles. In certain embodiments, cycle 1 to 4 are all 28 day cycles. In some embodiments, a therapeutically effective amount of Compound 1, Compound 2 or Compound 3 is administered for 1 to 13 cycles of 28 days (e.g. about 1 year). In certain instances, the cycling therapy is not limited to the number of cycles, and the therapy is continued until disease progression. Cycles can in certain instances include varying the duration of administration periods and/or rest periods described herein.

In one embodiment the treatment cycle includes administering Compound 1, Compound 2 or Compound 3 at a dosage amount of about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 2.0 mg/day, 5.0 mg/day, or 10 mg/day, administered once per day. In one embodiment the treatment cycle includes administering Compound 1, Compound 2 or Compound 3 at a dosage amount of about 0.1 mg/day, 0.2 mg/day, 0.3 mg/day, 0.4 mg/day, 0.5 mg/day, 0.6 mg/day, 0.7 mg/day, or 0.8 mg/day, administered once per day. In some such embodiments, the treatment cycle includes administering Compound 1, Compound 2 or Compound 3 once a day at a dosage amount of about 0.1 mg, 0.2 mg, 0.3 mg, 0.4 mg, or 0.5 mg on days 1 to 10 of a 28 day cycle. In some such embodiments, the treatment cycle includes administering Compound 1, Compound 2 or Compound 3 once a day at a dosage amount of about 0.1 mg, 0.2 mg, 0.3 mg, 0.4 mg, or 0.5 mg on days 1 to 10 and 15 to 24 of a 28 day cycle. In some such embodiments, the treatment cycle includes administering Compound 1, Compound 2 or Compound 3 once a day at a dosage amount of about 0.1 mg on days 1 to 10 and 15 to 24 of a 28 day cycle. In other embodiments, the treatment cycle includes administering Compound 1, Compound 2 or Compound 3 twice a day at a dosage amount of about 0.1 mg, 0.2 mg, 0.3 mg, 0.4 mg, or 0.5 mg on days 1 to 3 of a 28 day cycle. In other embodiments, the treatment cycle includes administering Compound 1, Compound 2 or Compound 3 twice a day at a dosage amount of about 0.1 mg, 0.2 mg, 0.3 mg, 0.4 mg, or 0.5 mg on days 1 to 3 and 15 to 19 of a 28 day cycle. In other embodiments, the treatment cycle includes administering Compound 1, Compound 2 or Compound 3 twice a day at a dosage amount of about 0.1 mg, 0.2 mg, 0.3 mg, 0.4 mg, or 0.5 mg on days 1 to 3 and 15 to 17 of a 28 day cycle. In other embodiments, the treatment cycle includes administering Compound 1, Compound 2 or Compound 3 twice a day at a dosage amount of about 0.2 mg on days 1 to 3 and 15 to 17 of a 28 day cycle. In one such embodiment, the compound is administered on days 1 to 3 (morning and evening), day 14 (evening only), days 15 and 16 (morning and evening), and day 17 (morning only) of a 28 day cycle, for example in Cycle 1.

H. Dosing of Second Active Agents

In one embodiment, the specific amount (dosage) of a second active agent provided herein as used in the methods provided herein is determined by factors such as the specific agent used, the type of multiple myeloma being treated or managed, the severity and stage of disease, the amount of Compound 1, Compound 2 or Compound 3, or an enantiomer, mixture of enantiomers, tautomer, isotopolog, or pharmaceutically acceptable salt thereof, and any optional additional active agents concurrently administered to the patient.

In one embodiment, the dosage of a second active agent provided herein as used in the methods provided herein is determined based on a commercial package insert of medicament (e.g., a label) as approved by the FDA or a similar regulatory agency of a country other than the USA for said active agent. In one embodiment, the dosage of a second active agent provided herein as used in the methods provided herein is a dosage approved by the FDA or a similar regulatory agency of a country other than the USA for said active agent. In one embodiment, the dosage of a second active agent provided herein as used in the methods provided herein is a dosage used in a human clinical trial for said active agent. In one embodiment, the dosage of a second active agent provided herein as used in the methods provided herein is lower than a dosage approved by the FDA or a similar regulatory agency of a country other than the USA for said active agent or a dosage used in a human clinical trial for said active agent, depending on, e.g., the synergistic effects between the second active agent and Compound 1, Compound 2 or Compound 3.

In one embodiment, the second active agent used in the methods provided herein is a BTK inhibitor. In one embodiment, the BTK inhibitor (e.g., ibrutinib) is administered at a dosage of in the range of from about 140 mg to about 700 mg, from about 280 mg to about 560 mg, or from about 420 mg to about 560 mg once daily. In one embodiment, the BTK inhibitor (e.g., ibrutinib) is administered at a dosage of no more than about 700 mg, no more than about 560 mg, no more than about 420 mg, no more than about 280 mg, or no more than about 140 mg once daily. In one embodiment, the BTK inhibitor (e.g., ibrutinib) is administered at a dosage of about 560 mg once daily. In one embodiment, the BTK inhibitor (e.g., ibrutinib) is administered at a dosage of about 420 mg once daily. In one embodiment, the BTK inhibitor (e.g., ibrutinib) is administered at a dosage of about 280 mg once daily. In one embodiment, the BTK inhibitor (e.g., ibrutinib) is administered at a dosage of about 140 mg once daily. In one embodiment, the BTK inhibitor (e.g., ibrutinib) is administered orally.

In one embodiment, the second active agent used in the methods provided herein is an mTOR inhibitor. In one embodiment, the mTOR inhibitor (e.g., everolimus) is administered at a dosage of in the range of from about 1 mg to about 20 mg, from about 2.5 mg to about 15 mg, or from about 5 mg to about 10 mg once daily. In one embodiment, the mTOR inhibitor (e.g., everolimus) is administered at a dosage of no more than about 20 mg, no more than about 15 mg, no more than about 10 mg, no more than about 5 mg, or no more than about 2.5 mg once daily. In one embodiment, the mTOR inhibitor (e.g., everolimus) is administered at a dosage of about 10 mg once daily. In one embodiment, the mTOR inhibitor (e.g., everolimus) is administered at a dosage of about 5 mg once daily. In one embodiment, the mTOR inhibitor (e.g., everolimus) is administered at a dosage of about 2.5 mg once daily. In one embodiment, the mTOR inhibitor (e.g., everolimus) is administered orally.

In one embodiment, the second active agent used in the methods provided herein is a PIM inhibitor. In one embodiment, the PIM inhibitor (e.g., LGH-447) is administered at a dosage of in the range of from about 30 mg to about 1000 mg, from about 70 mg to about 700 mg, from about 150 mg to about 500 mg, from about 200 mg to about 350 mg, or from about 250 mg to about 300 mg once daily. In one embodiment, the PIM inhibitor (e.g., LGH-447) is administered at a dosage of no more than about 700 mg, no more than about 500 mg, no more than about 350 mg, no more than about 300 mg, no more than about 250 mg, no more than about 200 mg, no more than about 150 mg, or no more than about 70 mg once daily. In one embodiment, the PIM inhibitor (e.g., LGH-447) is administered at a dosage of about 500 mg once daily. In one embodiment, the PIM inhibitor (e.g., LGH-447) is administered at a dosage of about 350 mg once daily. In one embodiment, the PIM inhibitor (e.g., LGH-447) is administered at a dosage of about 300 mg once daily. In one embodiment, the PIM inhibitor (e.g., LGH-447) is administered at a dosage of about 250 mg once daily. In one embodiment, the PIM inhibitor (e.g., LGH-447) is administered at a dosage of about 200 mg once daily. In one embodiment, the PIM inhibitor (e.g., LGH-447) is administered at a dosage of about 150 mg once daily. In one embodiment, the PIM inhibitor (e.g., LGH-447) is administered orally.

In one embodiment, the second active agent used in the methods provided herein is an IGF-1R inhibitor. In one embodiment, the IGF-1R inhibitor (e.g., linsitinib) is administered at a dosage of in the range of from about 100 mg to about 500 mg, from about 150 mg to about 450 mg, from about 200 mg to about 400 mg, or from about 250 mg to about 300 mg daily. In one embodiment, the IGF-1R inhibitor (e.g., linsitinib) is administered at a dosage of in the range of from about 50 mg to about 250 mg, from about 75 mg to about 225 mg, from about 100 mg to about 200 mg, or from about 125 mg to about 150 mg twice daily (BID). In one embodiment, the IGF-1R inhibitor (e.g., linsitinib) is administered at a dosage of no more than about 450 mg, no more than about 400 mg, no more than about 300 mg, no more than about 250 mg, no more than about 200 mg, or no more than about 150 mg daily. In one embodiment, the IGF-1R inhibitor (e.g., linsitinib) is administered at a dosage of no more than about 450 mg, no more than about 400 mg, no more than about 300 mg, no more than about 250 mg, no more than about 200 mg, or no more than about 150 mg daily. In one embodiment, the IGF-1R inhibitor (e.g., linsitinib) is administered at a dosage of no more than about 225 mg, no more than about 200 mg, no more than about 150 mg, no more than about 125 mg, no more than about 100 mg, or no more than about 75 mg twice daily. In one embodiment, the IGF-1R inhibitor (e.g., linsitinib) is administered at a dosage of about 450 mg, about 400 mg, about 300 mg, about 250 mg, about 200 mg, or about 150 mg daily. In one embodiment, the IGF-1R inhibitor (e.g., linsitinib) is administered at a dosage of about 225 mg, about 200 mg, about 150 mg, about 125 mg, about 100 mg, or about 75 mg twice daily. In one embodiment, the IGF-1R inhibitor (e.g., linsitinib) is administered on days 1 to 3 every 7 days. In one embodiment, the IGF-1R inhibitor (e.g., linsitinib) is administered orally.

In one embodiment, the second active agent used in the methods provided herein is an MEK inhibitor. In one embodiment, the MEK inhibitor (e.g., trametinib or trametinib dimethyl sulfoxide) is administered at a dosage of in the range of from about 0.25 mg to about 3 mg, from about 0.5 mg to about 2 mg, or from about 1 mg to about 1.5 mg once daily. In one embodiment, the MEK inhibitor (e.g., trametinib or trametinib dimethyl sulfoxide) is administered at a dosage of no more than about 2 mg, no more than about 1.5 mg, no more than about 1 mg, or no more than about 0.5 mg once daily. In one embodiment, the MEK inhibitor (e.g., trametinib or trametinib dimethyl sulfoxide) is administered at a dosage of about 2 mg once daily. In one embodiment, the MEK inhibitor (e.g., trametinib or trametinib dimethyl sulfoxide) is administered at a dosage of about 1.5 mg once daily. In one embodiment, the MEK inhibitor (e.g., trametinib or trametinib dimethyl sulfoxide) is administered at a dosage of about 1 mg once daily. In one embodiment, the MEK inhibitor (e.g., trametinib or trametinib dimethyl sulfoxide) is administered at a dosage of about 0.5 mg once daily. In one embodiment, the MEK inhibitor (e.g., trametinib or trametinib dimethyl sulfoxide) is administered orally.

In one embodiment, the second active agent used in the methods provided herein is an XPO1 inhibitor. In one embodiment, the XPO1 inhibitor (e.g., selinexor) is administered at a dosage of in the range of from about 30 mg to about 200 mg twice weekly, from about 45 mg to about 150 mg twice weekly, or from about 60 mg to about 100 mg twice weekly. In one embodiment, the XPO1 inhibitor (e.g., selinexor) is administered at a dosage of no more than about 100 mg, no more than about 80 mg, no more than about 60 mg, or no more than about 40 mg twice weekly. In one embodiment, the XPO1 inhibitor (e.g., selinexor) is administered at a dosage of about 20 mg, about 30 mg, about 40 mg, about 50 mg, about 60 mg, about 70 mg, about 80 mg, about 90 mg, or about 100 mg twice weekly. In one embodiment, the dosage is about 40 mg twice weekly. In one embodiment, the dosage is about 60 mg twice weekly. In one embodiment, the dosage is about 80 mg twice weekly. In one embodiment, the dosage is about 100 mg twice weekly. In one embodiment, the XPO1 inhibitor (e.g., selinexor) is administered orally.

In one embodiment, the second active agent used in the methods provided herein is a DOT1L inhibitor. In one embodiment, the DOT1L inhibitor (e.g., SGC0946) is administered at a dosage of in the range of from about 10 mg to about 500 mg, from about 25 mg to about 400 mg, from about 50 mg to about 300 mg, from about 75 mg to about 200 mg, or from about 100 mg to about 150 mg per day. In one embodiment, the DOT1L inhibitor (e.g., SGC0946) is administered at a dosage of no more than about 500 mg, no more than about 400 mg, no more than about 300 mg, no more than about 200 mg, no more than about 150 mg, no more than about 100 mg, no more than about 75 mg, no more than about 50 mg, or no more than about 25 mg per day. In one embodiment, the DOT1L inhibitor (e.g., SGC0946) is administered at a dosage of about 25 mg, about 50 mg, about 75 mg, about 100 mg, about 150 mg, about 200 mg, about 300 mg, about 400 mg, or about 500 mg. In one embodiment, the DOT1L inhibitor (e.g., SGC0946) is administered at a dosage of in the range of from about 18 mg/m$^2$ to about 126 mg/m$^2$, from about 36 mg/m$^2$ to about 108 mg/m$^2$, or from about 54 mg/m$^2$ to about 90 mg/m$^2$ per day. In one embodiment, the DOT1L inhibitor (e.g., SGC0946) is administered at a dosage of no more than about 126 mg/m$^2$, no more than about 108 mg/m$^2$, no more than about 90 mg/m$^2$, no more than about 72 mg/m$^2$, no more than about 54 mg/m$^2$, no more than about 36 mg/m$^2$, or no more than about 18 mg/m$^2$ per day. In one embodiment, the DOT1L inhibitor (e.g., SGC0946) is administered at a dosage of about 18 mg/m$^2$, about 36 mg/m$^2$, about 54 mg/m$^2$, about 72 mg/m$^2$, about 90 mg/m$^2$, about 108 mg/m$^2$, or about 126 mg/m$^2$ per day. In one embodiment, the DOT1L inhibitor (e.g., SGC0946) is administered orally. In one embodiment, the DOT1L inhibitor (e.g., SGC0946) is administered intravenously.

In one embodiment, the DOT1L inhibitor (e.g., pinometostat) is administered at a dosage of in the range of from about 18 mg/m$^2$ to about 108 mg/m$^2$, from about 36 mg/m$^2$ to about 90 mg/m$^2$, or from about 54 mg/m$^2$ to about 72 mg/m$^2$ per day. In one embodiment, the DOT1L inhibitor (e.g., pinometostat) is administered at a dosage of no more than about 108 mg/m$^2$, no more than about 90 mg/m$^2$, no more than about 72 mg/m$^2$, no more than about 54 mg/m$^2$, no more than about 36 mg/m$^2$, or no more than about 18 mg/m$^2$ per day. In one embodiment, the DOT1L inhibitor (e.g., pinometostat) is administered at a dosage of about 18 mg/m$^2$ per day. In one embodiment, the DOT1L inhibitor (e.g., pinometostat) is administered at a dosage of about 36 mg/m$^2$ per day. In one embodiment, the DOT1L inhibitor (e.g., pinometostat) is administered at a dosage of about 54 mg/m$^2$ per day. In one embodiment, the DOT1L inhibitor (e.g., pinometostat) is administered at a dosage of about 70 mg/m$^2$ per day. In one embodiment, the DOT1L inhibitor (e.g., pinometostat) is administered at a dosage of about 72 mg/m$^2$ per day. In one embodiment, the DOT1L inhibitor (e.g., pinometostat) is administered at a dosage of about 90 mg/m$^2$ per day. In one embodiment, the DOT1L inhibitor (e.g., pinometostat) is administered at a dosage of about 108 mg/m$^2$ per day. In one embodiment, the DOT1L inhibitor (e.g., pinometostat) is administered intravenously.

In one embodiment, the second active agent used in the methods provided herein is an EZH2 inhibitor. In one embodiment, the EZH2 inhibitor (e.g., tazemetostat) is administered at a dosage of in the range of from about 50 mg to about 1600 mg, from about 100 mg to about 800 mg, or from about 200 mg to about 400 mg twice daily (BID). In one embodiment, the EZH2 inhibitor (e.g., tazemetostat) is administered at a dosage of no more than about 800 mg, no more than about 600 mg, no more than about 400 mg, no more than about 200 mg, or no more than about 100 mg twice daily. In one embodiment, the EZH2 inhibitor (e.g., tazemetostat) is administered at a dosage of about 800 mg twice daily. In one embodiment, the EZH2 inhibitor (e.g., tazemetostat) is administered at a dosage of about 600 mg twice daily. In one embodiment, the EZH2 inhibitor (e.g., tazemetostat) is administered at a dosage of about 400 mg twice daily. In one embodiment, the EZH2 inhibitor (e.g., tazemetostat) is administered at a dosage of about 200 mg twice daily. In one embodiment, the EZH2 inhibitor (e.g., tazemetostat) is administered orally.

In one embodiment, the EZH2 inhibitor (e.g., CPI-1205) is administered at a dosage of in the range of from about 100 mg to about 3200 mg, from about 200 mg to about 1600 mg, or from about 400 mg to about 800 mg twice daily. In one embodiment, the EZH2 inhibitor (e.g., CPI-1205) is administered at a dosage of no more than about 3200 mg, no more than about 1600 mg, no more than about 800 mg, no more than about 400 mg, no more than about 200 mg, or no more than about 100 mg twice daily. In one embodiment, the EZH2 inhibitor (e.g., CPI-1205) is administered at a dosage of about 3200 mg twice daily. In one embodiment, the EZH2 inhibitor (e.g., CPI-1205) is administered at a dosage of about 1600 mg twice daily. In one embodiment, the EZH2 inhibitor (e.g., CPI-1205) is administered at a dosage of about 800 mg twice daily. In one embodiment, the EZH2 inhibitor (e.g., CPI-1205) is administered at a dosage of about 400 mg twice daily. In one embodiment, the EZH2 inhibitor (e.g., CPI-1205) is administered at a dosage of about 200 mg twice daily. In one embodiment, the EZH2 inhibitor (e.g., CPI-1205) is administered at a dosage of about 100 mg twice daily. In one embodiment, the EZH2 inhibitor (e.g., CPI-1205) is administered for one or more 28-day cycles. In one embodiment, the EZH2 inhibitor (e.g., CPI-1205) is administered orally.

In one embodiment, the second active agent used in the methods provided herein is a JAK2 inhibitor. In one embodiment, the JAK2 inhibitor (e.g., fedratinib) is administered at a dosage of in the range of from about 120 mg to about 680 mg, from about 240 mg to about 500 mg, or from about 300 mg to about 400 mg once daily. In one embodiment, the JAK2 inhibitor (e.g., fedratinib) is administered at a dosage of no more than about 680 mg, no more than about 500 mg, no more than about 400 mg, no more than about 300 mg, or no more than about 240 mg once daily. In one embodiment, the JAK2 inhibitor (e.g., fedratinib) is administered at a dosage of about 500 mg once daily. In one embodiment, the JAK2 inhibitor (e.g., fedratinib) is administered at a dosage of about 400 mg once daily. In one embodiment, the JAK2 inhibitor (e.g., fedratinib) is administered at a dosage of about 300 mg once daily.

In one embodiment, the second active agent used in the methods provided herein is a PLK1 inhibitor. In one embodiment, the PLK1 inhibitor (e.g., BI2536) is administered at a dosage of in the range of from about 20 mg to about 200 mg, from about 40 mg to about 100 mg, or from about 50 mg to about 60 mg per day. In one embodiment, the PLK1 inhibitor (e.g., BI2536) is administered at a dosage of no more than about 200 mg, no more than about 100 mg, no more than about 60 mg, no more than about 50 mg, no more than about 40 mg, or no more than about 20 mg per day. In one embodiment, the PLK1 inhibitor (e.g., BI2536) is administered at a dosage of about 200 mg, about 100 mg, about 60 mg, about 50 mg, about 40 mg, or about 20 mg per day. In one embodiment, the PLK1 inhibitor (e.g., BI2536) is administered at a dosage of about 200 mg once every 21-day cycle. In one embodiment, the PLK1 inhibitor (e.g., BI2536) is administered at a dosage of about 100 mg per day on days 1 and 8 of 21-day cycle. In one embodiment, the PLK1 inhibitor (e.g., BI2536) is administered at a dosage of about 50 mg per day on days 1 to 3 of 21-day cycle. In one embodiment, the PLK1 inhibitor (e.g., BI2536) is administered at a dosage of about 60 mg per day on days 1 to 3 of 21-day cycle. In one embodiment, the PLK1 inhibitor (e.g., BI2536) is administered intravenously.

In one embodiment, the second active agent used in the methods provided herein is an AURKB inhibitor. In one embodiment, the AURKB inhibitor (e.g., AZD1152) is administered at a dosage of in the range of from about 50 mg to about 200 mg, from about 75 mg to about 150 mg, or from about 100 mg to about 110 mg per day. In one embodiment, the AURKB inhibitor (e.g., AZD1152) is administered at a dosage of no more than about 200 mg, no more than about 150 mg, no more than about 110 mg, no more than about 100 mg, no more than about 75 mg, or no more than about 50 mg per day. In one embodiment, the AURKB inhibitor (e.g., AZD1152) is administered at a dosage of about 200 mg, about 150 mg, about 110 mg, about 100 mg, about 75 mg, or about 50 mg per day. In one embodiment, the AURKB inhibitor (e.g., AZD1152) is administered at a dosage described herein on days 1, 2, 15, and 16 of a 28-day cycle. In one embodiment, the AURKB inhibitor (e.g., AZD1152) is administered intravenously. In one embodiment, the AURKB inhibitor (e.g., AZD1152) is administered at a dosage of about 150 mg as a 48-hour continuous infusion every 14 days out of a 28-day cycle. In one embodiment, the AURKB inhibitor (e.g., AZD1152) is administered at a dosage of about 220 mg as 2×2-hour infusions every 14 days out of a 28-day cycle (e.g., 110 mg/day on days 1, 2, 15, and 16). In one embodiment, the AURKB inhibitor (e.g., AZD1152) is administered at a dosage of about 200 mg as a 2-hour infusion every 7 days. In one embodiment, the AURKB inhibitor (e.g., AZD1152) is administered at a dosage of about 450 mg as a 2-hour infusion every 14 days.

In one embodiment, the second active agent used in the methods provided herein is a BIRC5 inhibitor. In one embodiment, the BIRC5 inhibitor (e.g., YM155) is administered at a dosage of in the range of from about 2 mg/m$^2$ to about 15 mg/m$^2$, or from about 4 mg/m$^2$ to about 10 mg/m$^2$ per day. In one embodiment, the BIRC5 inhibitor (e.g., YM155) is administered at a dosage of no more than about 15 mg/m$^2$, no more than about 10 mg/m$^2$, no more than about 4.8 mg/m$^2$, no more than about 4 mg/m$^2$, or no more than about 2 mg/m$^2$ per day. In one embodiment, the BIRC5 inhibitor (e.g., YM155) is administered at a dosage of about 15 mg/m$^2$ per day. In one embodiment, the BIRC5 inhibitor (e.g., YM155) is administered at a dosage of about 10 mg/m$^2$ per day. In one embodiment, the BIRC5 inhibitor (e.g., YM155) is administered at a dosage of about 4.8 mg/m$^2$ per day. In one embodiment, the BIRC5 inhibitor (e.g., YM155) is administered at a dosage of about 4 mg/m$^2$ per day. In one embodiment, the BIRC5 inhibitor (e.g., YM155) is administered at a dosage of about 2 mg/m$^2$ per day. In one embodiment, the BIRC5 inhibitor (e.g., YM155) is administered intravenously. In one embodiment, the BIRC5 inhibitor (e.g., YM155) is administered at a dosage of about 4.8 mg/m$^2$/day by about 168 hours continuous IV infusion every 3 weeks. In one embodiment, the BIRC5 inhibitor (e.g., YM155) is administered at a dosage of about 5 mg/m$^2$/day by about 168 hours continuous IV infusion every 3 weeks. In one embodiment, the BIRC5 inhibitor (e.g., YM155) is administered at a dosage of about 10 mg/m$^2$/day by about 72 hours continuous IV infusion every 3 weeks.

In one embodiment, the second active agent used in the methods provided herein is an BET inhibitor. In one embodiment, the BET inhibitor (e.g., birabresib) is administered at a dosage of in the range of from about 10 mg to about 160 mg, from about 20 mg to about 120 mg, or from about 40 mg to about 80 mg once daily. In one embodiment, the BET inhibitor (e.g., birabresib) is administered at a dosage of no more than about 160 mg, no more than about 120 mg, no more than about 80 mg, no more than about 40 mg, no more than about 20 mg, or no more than about 10 mg once daily. In one embodiment, the BET inhibitor (e.g., birabresib) is administered at a dosage of about 160 mg once daily. In one embodiment, the BET inhibitor (e.g., birabresib) is administered at a dosage of about 120 mg once daily. In one embodiment, the BET inhibitor (e.g., birabresib) is administered at a dosage of about 80 mg once daily. In one embodiment, the BET inhibitor (e.g., birabresib) is administered at a dosage of about 40 mg once daily. In one embodiment, the BET inhibitor (e.g., birabresib) is administered at a dosage of about 20 mg once daily. In one embodiment, the BET inhibitor (e.g., birabresib) is administered at a dosage of about 10 mg once daily. In one embodiment, the BET inhibitor (e.g., birabresib) is administered at a dosage described herein on Days 1 to 7 of a 21-day cycle. In one embodiment, the BET inhibitor (e.g., birabresib) is administered at a dosage described herein on Days 1 to 14 of a 21-day cycle. In one embodiment, the BET inhibitor (e.g., birabresib) is administered at a dosage described herein on Days 1 to 21 of a 21-day cycle. In one embodiment, the BET inhibitor (e.g., birabresib) is administered at a dosage described herein on Days 1 to 5 of a 7-day cycle. In one embodiment, the BET inhibitor (e.g., birabresib) is administered orally.

In one embodiment, the second active agent used in the methods provided herein is a DNA methyltransferase inhibitor. In one embodiment, the DNA methyltransferase inhibitor (e.g., azacitidine) is administered at a dosage of in the range of from about 25 mg/m$^2$ to about 150 mg/m$^2$, from about 50 mg/m$^2$ to about 125 mg/m$^2$, or from about 75 mg/m$^2$ to about 100 mg/m$^2$ daily. In one embodiment, the DNA methyltransferase inhibitor (e.g., azacitidine) is administered at a dosage of no more than about 150 mg/m$^2$, no more than about 125 mg/m$^2$, no more than about 100 mg/m$^2$, no more than about 75 mg/m$^2$, no more than about 50 mg/m$^2$, or no more than about 25 mg/m$^2$ daily. In one embodiment, the DNA methyltransferase inhibitor (e.g., azacitidine) is administered at a dosage of about 150 mg/m$^2$ daily. In one embodiment, the DNA methyltransferase inhibitor (e.g., azacitidine) is administered at a dosage of about 125 mg/m$^2$ daily. In one embodiment, the DNA methyltransferase inhibitor (e.g., azacitidine) is administered at a dosage of about 100 mg/m$^2$ daily. In one embodiment, the DNA methyltransferase inhibitor (e.g., azacitidine) is administered at a dosage of about 75 mg/m$^2$ daily. In one embodiment, the DNA methyltransferase inhibitor (e.g., azacitidine) is administered at a dosage of about 50 mg/m$^2$ daily. In one embodiment, the DNA methyltransferase inhibitor (e.g., azacitidine) is administered at a dosage of about 25 mg/m$^2$ daily. In one embodiment, the DNA methyltransferase inhibitor (e.g., azacitidine) is administered subcutaneously. In one embodiment, the DNA methyltransferase inhibitor (e.g., azacitidine) is administered intravenously.

In one embodiment, the DNA methyltransferase inhibitor (e.g., azacitidine) is administered at a dosage of in the range of from about 100 mg to about 500 mg, or from about 200 mg to about 400 mg once daily. In one embodiment, the DNA methyltransferase inhibitor (e.g., azacitidine) is administered at a dosage of no more than about 500 mg, no more than about 400 mg, no more than about 300 mg, no more than about 200 mg, or no more than about 100 mg once daily. In one embodiment, the DNA methyltransferase inhibitor (e.g., azacitidine) is administered at a dosage of about 500 mg once daily. In one embodiment, the DNA methyltransferase inhibitor (e.g., azacitidine) is administered at a dosage of about 400 mg once daily. In one embodiment, the DNA methyltransferase inhibitor (e.g., azacitidine) is administered at a dosage of about 300 mg once daily. In one embodiment, the DNA methyltransferase inhibitor (e.g., azacitidine) is administered at a dosage of about 200 mg once daily. In one embodiment, the DNA methyltransferase inhibitor (e.g., azacitidine) is administered at a dosage of about 100 mg once daily. In one embodiment, the DNA methyltransferase inhibitor (e.g., azacitidine) is administered at a dosage of in the range of from about 100 mg to about 300 mg, or from about 150 mg to about 250 mg twice daily. In one embodiment, the DNA methyltransferase inhibitor (e.g., azacitidine) is administered at a dosage of no more than about 300 mg, no more than about 250 mg, no more than about 200 mg, no more than about 150 mg, or no more than about 100 mg twice daily. In one embodiment, the DNA methyltransferase inhibitor (e.g., azacitidine) is administered at a dosage of about 300 mg twice daily. In one embodiment, the DNA methyltransferase inhibitor (e.g., azacitidine) is administered at a dosage of about 250 mg twice daily. In one embodiment, the DNA methyltransferase inhibitor (e.g., azacitidine) is administered at a dosage of about 200 mg twice daily. In one embodiment, the DNA methyltransferase inhibitor (e.g., azacitidine) is administered at a dosage of about 150 mg twice daily. In one embodiment, the DNA methyltransferase inhibitor (e.g., azacitidine) is administered at a dosage of about 100 mg twice daily. In one embodiment, the DNA methyltransferase inhibitor (e.g., azacitidine) is administered at a dosage described herein on Days 1 to 14 of a 28-day cycle. In one embodiment, the DNA methyltransferase inhibitor (e.g., azacitidine) is administered at a dosage described herein on Days 1 to 21 of a 28-day cycle. In one embodiment, the DNA methyltransferase inhibitor (e.g., azacitidine) is administered orally.

I. Combination Therapy with Additional Active Agent

The combined use of a compound provided herein (e.g., Compound 1, Compound 2 or Compound 3, or an enantiomer, mixture of enantiomers, tautomer, isotopolog, or pharmaceutically acceptable salt thereof) and a second active agent provided herein (e.g., one or more of ibrutinib, everolimus, LGH-447, linsitinib, trametinib, trametinib dimethyl sulfoxide, selinexor, SGC0946, pinometostat, tazemetostat, UNC1999, CPI-1205, fedratinib, JQ1, BI2536, JH295, barasertib, AZD1152-HQPA, YM155, Compound C, or azacitidine, or a stereoisomer, mixture of stereoisomers, tautomer, isotopolog, or pharmaceutically acceptable salt thereof) can also be further combined or used in conjunction with (e.g. before, during, or after) conventional therapy including, but not limited to, surgery, biological therapy (including immunotherapy, for example with checkpoint inhibitors), radiation therapy, chemotherapy, stem cell transplantation, cell therapy, or other non-drug based therapy presently used to treat, prevent or manage multiple myeloma. The combined use of the compound provided herein, the second active agent provided herein, and conventional therapy may provide a unique treatment regimen that is unexpectedly effective in certain patients. Without being limited by theory, it is believed that Compound 1, Compound 2 or Compound 3 and a second active agent provided herein may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, biological therapy and immunotherapy. A compound provided herein, e.g., Compound 1, Compound 2 or Compound 3, or an enantiomer, mixture of enantiomers, tautomer, isotopolog, or pharmaceutically acceptable salt thereof, a second active agent provided herein, and an additional active ingredient can be administered to a patient prior to, during, or after the occurrence of the adverse effect associated with conventional therapy. In one such embodiment, the additional active agent is dexamethasone.

The combined use of a compound provided herein (e.g., Compound 1, Compound 2 or Compound 3, or an enantiomer, mixture of enantiomers, tautomer, isotopolog, or pharmaceutically acceptable salt thereof) and a second active agent provided herein (e.g., one or more of ibrutinib, everolimus, LGH-447, linsitinib, trametinib, trametinib dimethyl sulfoxide, selinexor, SGC0946, pinometostat, tazemetostat, UNC1999, CPI-1205, fedratinib, JQ1, BI2536, JH295, barasertib, AZD1152-HQPA, YM155, Compound C, or azacitidine, or a stereoisomer, mixture of stereoisomers, tautomer, isotopolog, or pharmaceutically acceptable salt thereof) can also be further combined or used in combination with other therapeutic agents useful in the treatment and/or prevention of multiple myeloma described herein. In one such embodiment, the additional active agent is dexamethasone.

In one embodiment, provided herein is a method of treating, preventing, or managing multiple myeloma, comprising administering to a patient Compound 1, Compound 2 or Compound 3, or an enantiomer, mixture of enantiomers, tautomer, isotopolog, or pharmaceutically acceptable salt thereof, in combination with a second active agent provided herein, further in combination with one or more additional active agents, and optionally further in combination with radiation therapy, blood transfusions, or surgery.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein, e.g., Compound 1, Compound 2 or Compound 3, or an enantiomer, mixture of enantiomers, tautomer, isotopolog, or pharmaceutically acceptable salt thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second active agent provided herein, e.g., one or more of ibrutinib, everolimus, LGH-447, linsitinib, trametinib, trametinib dimethyl sulfoxide, selinexor, SGC0946, pinometostat, tazemetostat, UNC1999, CPI-1205, fedratinib, JQ1, B12536, JH295, barasertib, AZD1152-HQPA, YM155, Compound C, or azacitidine, or a stereoisomer, mixture of stereoisomers, tautomer, isotopolog, or pharmaceutically acceptable salt thereof) to the subject. The first therapy and the second therapy independently can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a third therapy (e.g., an additional prophylactic or therapeutic agent) to the subject. Quadruple therapy is also contemplated herein, as is quintuple therapy. In one embodiment, the third therapy is dexamethasone.

Administration of Compound 1, Compound 2 or Compound 3, or an enantiomer, mixture of enantiomers, tautomer, isotopolog, or pharmaceutically acceptable salt thereof, a second active agent provided herein, and one or more additional active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream).

The route of administration of Compound 1, Compound 2 or Compound 3, or an enantiomer, mixture of enantiomers, tautomer, isotopolog, or pharmaceutically acceptable salt thereof, is independent of the route of administration of a second active agent provided herein as well as an additional therapy. In one embodiment, Compound 1, Compound 2 or Compound 3, or an enantiomer, mixture of enantiomers, tautomer, isotopolog, or pharmaceutically acceptable salt thereof, is administered orally. In another embodiment, Compound 1, Compound 2 or Compound 3 is administered intravenously. In one embodiment, a second active agent provided herein is administered orally. In one embodiment, a second active agent provided herein is administered intravenously. Thus, in accordance with these embodiments, Compound 1, Compound 2 or Compound 3, or an enantiomer, mixture of enantiomers, tautomer, isotopolog, or pharmaceutically acceptable salt thereof, is administered orally or intravenously, a second active agent provided herein is administered orally or intravenously, and the additional therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, Compound 1, Compound 2 or Compound 3, or an enantiomer, mixture of enantiomers, tautomer, isotopolog, or pharmaceutically acceptable salt thereof, a second active agent provided herein, and an additional therapy are administered by the same mode of administration, orally or by IV. In another embodiment, Compound 1, Compound 2 or Compound 3, or an enantiomer, mixture of enantiomers, tautomer, isotopolog, or pharmaceutically acceptable salt thereof, is administered by one mode of administration, e.g., by IV, whereas a second active agent provided herein or the additional agent (an anti-multiple myeloma agent) is administered by another mode of administration, e.g., orally.

In one embodiment, the additional active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the additional active agent will depend on the specific agent used, the type of multiple myeloma being treated or managed, the severity and stage of disease, the amount of Compound 1, Compound 2 or Compound 3, or an enantiomer, mixture of enantiomers, tautomer, isotopolog, or pharmaceutically acceptable salt thereof, the amount of a second active agent provided herein, and any optional additional active agents concurrently administered to the patient.

One or more additional active ingredients or agents can be used together with Compound 1, Compound 2 or Compound 3 and a second active agent provided herein in the methods and compositions provided herein. Additional active agents can be large molecules (e.g., proteins), small molecules (e.g., synthetic inorganic, organometallic, or organic molecules), or cell therapies (e.g., CAR cells).

Examples of additional active agents that can be used in the methods and compositions described herein include one or more of melphalan, vincristine, cyclophosphamide, etoposide, doxorubicin, bendamustine, obinutuzmab, a proteasome inhibitor (for example, bortezomib, carfilzomib, ixazomib, oprozomib or marizomib), a histone deacetylase inhibitor (for example, panobinostat, ACY241), a BET inhibitor (for example, GSK525762A, OTX015, BMS-986158, TEN-010, CPI-0610, INCB54329, BAY1238097, FT-1101, ABBV-075, BI 894999, GS-5829, GSK1210151A (I-BET-151), CPI-203, RVX-208, XD46, MS436, PFI-1, RVX2135, ZEN3365, XD14, ARV-771, MZ-1, PLX5117, 4-[2-(cyclopropylmethoxy)-5-(methanesulfonyl)phenyl]-2-methylisoquinolin-1(2H)-one, EP11313 and EP11336), a BCL2 inhibitor (for example, venetoclax or navitoclax), an MCL-1 inhibitor (for example, AZD5991, AMG176, MIK665, S64315, or S63845), an LSD-1 inhibitor (for example, ORY-1001, ORY-2001, INCB-59872, IMG-7289, TAK-418, GSK-2879552, 4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile or a salt thereof), a corticosteroid (for example, prednisone), dexamethasone; an antibody (for example, a CS1 antibody, such as elotuzumab; a CD38 antibody, such as daratumumab or isatuximab; or a BCMA antibody or antibody-conjugate, such as GSK2857916 or BI 836909), a checkpoint inhibitor (as described herein), or CAR cells (as described herein).

In one embodiment, the additional active agent used together with Compound 1, Compound 2 or Compound 3, or an enantiomer, mixture of enantiomers, tautomer, isotopolog, or pharmaceutically acceptable salt thereof, and a second active agent provided herein in the methods and compositions described herein is dexamethasone.

In some embodiments, the dexamethasone is administered at a 4 mg dose on days 1 and 8 of a 21 day cycle. In some other embodiments, the dexamethasone is administered at a 4 mg dose on days 1, 4, 8 and 11 of a 21 day cycle. In some embodiments, the dexamethasone is administered at a 4 mg dose on days 1, 8, and 15 of a 28 day cycle. In some other embodiments, the dexamethasone is administered at a 4 mg dose on days 1, 4, 8, 11, 15 and 18 of a 28 day cycle. In some embodiments, the dexamethasone is administered at a 4 mg dose on days 1, 8, 15, and 22 of a 28 day cycle. In one such embodiment, the dexamethasone is administered at a 4 mg dose on days 1, 10, 15, and 22 of Cycle 1. In some embodiments, the dexamethasone is administered at a 4 mg dose on days 1, 3, 15, and 17 of a 28 day cycle. In one such embodiment, the dexamethasone is administered at a 4 mg dose on days 1, 3, 14, and 17 of Cycle 1.

In some other embodiments, the dexamethasone is administered at an 8 mg dose on days 1 and 8 of a 21 day cycle. In some other embodiments, the dexamethasone is administered at an 8 mg dose on days 1, 4, 8 and 11 of a 21 day cycle. In some embodiments, the dexamethasone is administered at an 8 mg dose on days 1, 8, and 15 of a 28 day cycle. In some other embodiments, the dexamethasone is administered at an 8 mg dose on days 1, 4, 8, 11, 15 and 18 of a 28 day cycle. In some embodiments, the dexamethasone is administered at an 8 mg dose on days 1, 8, 15, and 22 of a 28 day cycle. In one such embodiment, the dexamethasone is administered at an 8 mg dose on days 1, 10, 15, and 22 of Cycle 1. In some embodiments, the dexamethasone is administered at an 8 mg dose on days 1, 3, 15, and 17 of a 28 day cycle. In one such embodiment, the dexamethasone is administered at an 8 mg dose on days 1, 3, 14, and 17 of Cycle 1.

In some embodiments, the dexamethasone is administered at a 10 mg dose on days 1 and 8 of a 21 day cycle. In some other embodiments, the dexamethasone is administered at a 10 mg dose on days 1, 4, 8 and 11 of a 21 day cycle. In some embodiments, the dexamethasone is administered at a 10 mg dose on days 1, 8, and 15 of a 28 day cycle. In some other embodiments, the dexamethasone is administered at a 10 mg dose on days 1, 4, 8, 11, 15 and 18 of a 28 day cycle. In some embodiments, the dexamethasone is administered at a 10 mg dose on days 1, 8, 15, and 22 of a 28 day cycle. In one such embodiment, the dexamethasone is administered at a 10 mg dose on days 1, 10, 15, and 22 of Cycle 1. In some embodiments, the dexamethasone is administered at a 10 mg dose on days 1, 3, 15, and 17 of a 28 day cycle. In one such embodiment, the dexamethasone is administered at a 10 mg dose on days 1, 3, 14, and 17 of Cycle 1.

In some embodiments, the dexamethasone is administered at a 20 mg dose on days 1 and 8 of a 21 day cycle. In some other embodiments, the dexamethasone is administered at a 20 mg dose on days 1, 4, 8 and 11 of a 21 day cycle. In some embodiments, the dexamethasone is administered at a 20 mg dose on days 1, 8, and 15 of a 28 day cycle. In some other embodiments, the dexamethasone is administered at a 20 mg dose on days 1, 4, 8, 11, 15 and 18 of a 28 day cycle. In some embodiments, the dexamethasone is administered at a 20 mg dose on days 1, 8, 15, and 22 of a 28 day cycle. In one such embodiment, the dexamethasone is administered at a 20 mg dose on days 1, 10, 15, and 22 of Cycle 1. In some embodiments, the dexamethasone is administered at a 20 mg dose on days 1, 3, 15, and 17 of a 28 day cycle. In one such embodiment, the dexamethasone is administered at a 20 mg dose on days 1, 3, 14, and 17 of Cycle 1.

In some embodiments, the dexamethasone is administered at a 40 mg dose on days 1 and 8 of a 21 day cycle. In some other embodiments, the dexamethasone is administered at a 40 mg dose on days 1, 4, 8 and 11 of a 21 day cycle. In some embodiments, the dexamethasone is administered at a 40 mg dose on days 1, 8, and 15 of a 28 day cycle. In one such embodiment, the dexamethasone is administered at a 40 mg dose on days 1, 10, 15, and 22 of Cycle 1. In some other embodiments, the dexamethasone is administered at a 40 mg dose on days 1, 4, 8, 11, 15 and 18 of a 28 day cycle. In other such embodiments, the dexamethasone is administered at a 40 mg dose on days 1, 8, 15, and 22 of a 28 day cycle. In other such embodiments, the dexamethasone is administered at a 40 mg dose on days 1, 3, 15, and 17 of a 28 day cycle. In one such embodiment, the dexamethasone is administered at a 40 mg dose on days 1, 3, 14, and 17 of Cycle 1.

In another embodiment, the additional active agent used together with Compound 1, Compound 2 or Compound 3, or an enantiomer, mixture of enantiomers, tautomer, isotopolog, or pharmaceutically acceptable salt thereof, and a second active agent provided herein in the methods and compositions described herein is bortezomib. In yet another embodiment, the additional active agent used together with Compound 1, Compound 2 or Compound 3, or an enantiomer, mixture of enantiomers, tautomer, isotopolog, or pharmaceutically acceptable salt thereof, and a second active agent provided herein in the methods and compositions described herein is daratumumab. In some such embodiments, the methods additionally comprise administration of dexamethasone. In some embodiments, the methods comprise administration of Compound 1, Compound 2 or Compound 3, or an enantiomer, mixture of enantiomers, tautomer, isotopolog, or pharmaceutically acceptable salt thereof, and a second active agent provided herein with a proteasome inhibitor as described herein, a CD38 inhibitor as described herein and a corticosteroid as described herein.

In certain embodiments, Compound 1, Compound 2 or Compound 3, or an enantiomer, mixture of enantiomers, tautomer, isotopolog, or pharmaceutically acceptable salt thereof, and a second active agent provided herein are administered in combination with checkpoint inhibitors. In one embodiment, one checkpoint inhibitor is used in combination with Compound 1, Compound 2 or Compound 3, or an enantiomer, mixture of enantiomers, tautomer, isotopolog, or pharmaceutically acceptable salt thereof, and a second active agent provided herein in connection with the methods provided herein. In another embodiment, two checkpoint inhibitors are used in combination with Compound 1, Compound 2 or Compound 3, or an enantiomer, mixture of enantiomers, tautomer, isotopolog, or pharmaceutically acceptable salt thereof, and a second active agent provided herein in connection with the methods provided herein. In yet another embodiment, three or more checkpoint inhibitors are used in combination with Compound 1, Compound 2 or Compound 3, or an enantiomer, mixture of enantiomers, tautomer, isotopolog, or pharmaceutically acceptable salt thereof, and a second active agent provided herein in connection with the methods provided herein.

As used herein, the term "immune checkpoint inhibitor" or "checkpoint inhibitor" refers to molecules that totally or partially reduce, inhibit, interfere with or modulate one or more checkpoint proteins. Without being limited by a particular theory, checkpoint proteins regulate T-cell activation or function. Numerous checkpoint proteins are known, such as CTLA-4 and its ligands CD80 and CD86; and PD-1 with its ligands PD-L1 and PD-L2 (Pardoll, Nature Reviews Cancer, 2012, 12, 252-264). These proteins appear responsible for co-stimulatory or inhibitory interactions of T-cell responses. Immune checkpoint proteins appear to regulate and maintain self-tolerance and the duration and amplitude of physiological immune responses. Immune checkpoint inhibitors include antibodies or are derived from antibodies.

In one embodiment, the checkpoint inhibitor is a CTLA-4 inhibitor. In one embodiment, the CTLA-4 inhibitor is an anti-CTLA-4 antibody. Examples of anti-CTLA-4 antibodies include, but are not limited to, those described in U.S. Pat. Nos. 5,811,097; 5,811,097; 5,855,887; 6,051,227; 6,207,157; 6,682,736; 6,984,720; and 7,605,238, all of which are incorporated herein in their entireties. In one embodiment, the anti-CTLA-4 antibody is tremelimumab (also known as ticilimumab or CP-675,206). In another embodiment, the anti-CTLA-4 antibody is ipilimumab (also known as MDX-010 or MDX-101). Ipilimumab is a fully human monoclonal IgG antibody that binds to CTLA-4. Ipilimumab is marketed under the trade name Yervoy™.

In one embodiment, the checkpoint inhibitor is a PD-1/PD-L1 inhibitor. Examples of PD-1/PD-L1 inhibitors include, but are not limited to, those described in U.S. Pat. Nos. 7,488,802; 7,943,743; 8,008,449; 8,168,757; 8,217,149, and PCT Patent Application Publication Nos. WO2003042402, WO2008156712, WO2010089411, WO2010036959, WO2011066342, WO2011159877, WO2011082400, and WO2011161699, all of which are incorporated herein in their entireties.

In one embodiment, the checkpoint inhibitor is a PD-1 inhibitor. In one embodiment, the PD-1 inhibitor is an anti-PD-1 antibody. In one embodiment, the anti-PD-1 antibody is BGB-A317, nivolumab (also known as ONO-4538, BMS-936558, or MDX1106) or pembrolizumab (also known as MK-3475, SCH 900475, or lambrolizumab). In one embodiment, the anti-PD-1 antibody is nivolumab. Nivolumab is a human IgG4 anti-PD-1 monoclonal antibody, and is marketed under the trade name Opdivo™. In another embodiment, the anti-PD-1 antibody is pembrolizumab. Pembrolizumab is a humanized monoclonal IgG4 antibody and is marketed under the trade name Keytruda™. In yet another embodiment, the anti-PD-1 antibody is CT-011, a humanized antibody. CT-011 administered alone has failed to show response in treating acute myeloid leukemia (AML) at relapse. In yet another embodiment, the anti-PD-1 antibody is AMP-224, a fusion protein. In another embodiment, the PD-1 antibody is BGB-A317. BGB-A317 is a monoclonal antibody in which the ability to bind Fc gamma receptor I is specifically engineered out, and which has a unique binding signature to PD-1 with high affinity and superior target specificity.

In one embodiment, the checkpoint inhibitor is a PD-L1 inhibitor. In one embodiment, the PD-L1 inhibitor is an anti-PD-L1 antibody. In one embodiment, the anti-PD-L1 antibody is MEDI4736 (durvalumab). In another embodiment, the anti-PD-L1 antibody is BMS-936559 (also known as MDX-1105-01). In yet another embodiment, the PD-L1 inhibitor is atezolizumab (also known as MPDL3280A, and Tecentriq®).

In one embodiment, the checkpoint inhibitor is a PD-L2 inhibitor. In one embodiment, the PD-L2 inhibitor is an anti-PD-L2 antibody. In one embodiment, the anti-PD-L2 antibody is rHIgM12B7A.

In one embodiment, the checkpoint inhibitor is a lymphocyte activation gene-3 (LAG-3) inhibitor. In one embodiment, the LAG-3 inhibitor is IMP321, a soluble Ig fusion protein (Brignone et al., J. Immunol., 2007, 179, 4202-4211). In another embodiment, the LAG-3 inhibitor is BMS-986016.

In one embodiment, the checkpoint inhibitors is a B7 inhibitor. In one embodiment, the B7 inhibitor is a B7-H3 inhibitor or a B7-H4 inhibitor. In one embodiment, the B7-H3 inhibitor is MGA271, an anti-B7-H3 antibody (Loo et al., Clin. Cancer Res., 2012, 3834).

In one embodiment, the checkpoint inhibitors is a TIM3 (T-cell immunoglobulin domain and mucin domain 3) inhibitor (Fourcade et al., J. Exp. Med., 2010, 207, 2175-86; Sakuishi et al., J. Exp. Med., 2010, 207, 2187-94).

In one embodiment, the checkpoint inhibitor is an OX40 (CD134) agonist. In one embodiment, the checkpoint inhibitor is an anti-OX40 antibody. In one embodiment, the anti-OX40 antibody is anti-OX-40. In another embodiment, the anti-OX40 antibody is MEDI6469.

In one embodiment, the checkpoint inhibitor is a GITR agonist. In one embodiment, the checkpoint inhibitor is an anti-GITR antibody. In one embodiment, the anti-GITR antibody is TRX518.

In one embodiment, the checkpoint inhibitor is a CD137 agonist. In one embodiment, the checkpoint inhibitor is an anti-CD137 antibody. In one embodiment, the anti-CD137 antibody is urelumab. In another embodiment, the anti-CD137 antibody is PF-05082566.

In one embodiment, the checkpoint inhibitor is a CD40 agonist. In one embodiment, the checkpoint inhibitor is an anti-CD40 antibody. In one embodiment, the anti-CD40 antibody is CF-870,893.

In one embodiment, the checkpoint inhibitor is recombinant human interleukin-15 (rhIL-15).

In one embodiment, the checkpoint inhibitor is an IDO inhibitor. In one embodiment, the IDO inhibitor is INCB024360. In another embodiment, the IDO inhibitor is indoximod.

In certain embodiments, the combination therapies provided herein include two or more of the checkpoint inhibitors described herein (including checkpoint inhibitors of the same or different class). Moreover, the combination therapies described herein can be used in combination with one or more second active agents as described herein where appropriate for treating diseases described herein and understood in the art.

In certain embodiments, Compound 1, Compound 2 or Compound 3 and a second active agent provided herein can be used in combination with one or more immune cells expressing one or more chimeric antigen receptors (CARs) on their surface (e.g., a modified immune cell). Generally, CARs comprise an extracellular domain from a first protein (e.g., an antigen-binding protein), a transmembrane domain, and an intracellular signaling domain. In certain embodiments, once the extracellular domain binds to a target protein such as a tumor-associated antigen (TAA) or tumor-specific antigen (TSA), a signal is generated via the intracellular signaling domain that activates the immune cell, e.g., to target and kill a cell expressing the target protein.

Extracellular domains: The extracellular domains of the CARs bind to an antigen of interest. In certain embodiments, the extracellular domain of the CAR comprises a receptor, or a portion of a receptor, that binds to said antigen. In certain embodiments, the extracellular domain comprises, or is, an antibody or an antigen-binding portion thereof. In specific embodiments, the extracellular domain comprises, or is, a single chain Fv (scFv) domain. The single-chain Fv domain can comprise, for example, a $V_L$ linked to $V_H$ by a flexible linker, wherein said $V_L$ and $V_H$ are from an antibody that binds said antigen.

In certain embodiments, the antigen recognized by the extracellular domain of a polypeptide described herein is a tumor-associated antigen (TAA) or a tumor-specific antigen (TSA). In various specific embodiments, the tumor-associated antigen or tumor-specific antigen is, without limitation, Her2, prostate stem cell antigen (PSCA), alpha-fetoprotein (AFP), carcinoembryonic antigen (CEA), cancer antigen-125 (CA-125), CA19-9, calretinin, MUC-1, B cell maturation antigen (BCMA), epithelial membrane protein (EMA), epithelial tumor antigen (ETA), tyrosinase, melanoma-24 associated antigen (MAGE), CD19, CD22, CD27, CD30, CD34, CD45, CD70, CD99, CD117, EGFRvIII (epidermal growth factor variant III), mesothelin, PAP (prostatic acid phosphatase), prostein, TARP (T cell receptor gamma alternate reading frame protein), Trp-p8, STEAPI (six-transmembrane epithelial antigen of the prostate 1), chromogranin, cytokeratin, desmin, glial fibrillary acidic protein (GFAP), gross cystic disease fluid protein (GCDFP-15), HMB-45 antigen, protein melan-A (melanoma antigen recognized by T lymphocytes; MART-I), myo-D1, muscle-specific actin (MSA), neurofilament, neuron-specific enolase (NSE), placental alkaline phosphatase, synaptophysis, thyroglobulin, thyroid transcription factor-1, the dimeric form of the pyruvate kinase isoenzyme type M2 (tumor M2-PK), an abnormal ras protein, or an abnormal p53 protein. In certain other embodiments, the TAA or TSA recognized by the extracellular domain of a CAR is integrin $\alpha v\beta 3$ (CD61), galactin, or Ral-B.

In certain embodiments, the TAA or TSA recognized by the extracellular domain of a CAR is a cancer/testis (CT) antigen, e.g., BAGE, CAGE, CTAGE, FATE, GAGE, HCA661, HOM-TES-85, MAGEA, MAGEB, MAGEC, NA88, NY-ESO-1, NY-SAR-35, OY-TES-1, SPANXBI, SPA17, SSX, SYCPI, or TPTE.

In certain other embodiments, the TAA or TSA recognized by the extracellular domain of a CAR is a carbohydrate or ganglioside, e.g., fuc-GMI, GM2 (oncofetal antigen-immunogenic-1; OFA-I-1); GD2 (OFA-I-2), GM3, GD3, and the like.

In certain other embodiments, the TAA or TSA recognized by the extracellular domain of a CAR is alpha-actinin-4, Bage-1, BCR-ABL, Bcr-Abl fusion protein, beta-catenin, CA 125, CA 15-3 (CA 27.29\BCAA), CA 195, CA 242, CA-50, CAM43, Casp-8, cdc27, cdk4, cdkn2a, CEA, coa-1, dek-can fusion protein, EBNA, EF2, Epstein Barr virus antigens, ETV6-AML1 fusion protein, HLA-A2, HLA-All, hsp70-2, KIAA0205, Mart2, Mum-1, 2, and 3, neo-PAP, myosin class I, OS-9, pml-RAR$\alpha$ fusion protein, PTPRK, K-ras, N-ras, triosephosphate isomerase, Gage 3,4,5,6,7, GnTV, Herv-K-mel, Lage-1, NA-88, NY-Eso-1/Lage-2, SP17, SSX-2, TRP2-Int2, gp00 (Pmel17), tyrosinase, TRP-1, TRP-2, MAGE-1, MAGE-3, RAGE, GAGE-1, GAGE-2, p15(58), RAGE, SCP-1, Hom/Mel-40, PRAME, p53, HRas, HER-2/neu, E2A-PRL, H4-RET, IGH-IGK, MYL-RAR, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, 13-Catenin, Mum-1, p16, TAGE, PSMA, CT7, telomerase, 43-9F, 5T4, 791Tgp72, 13HCG, BCA225, BTAA, CD68\KP1, CO-029, FGF-5, G250, Ga733 (EpCAM), HTgp-175, M344, MA-50, MG7-Ag, MOV18, NB\70K, NY-CO-1, RCAS1, SDCCAG16, TA-90, TAAL6, TAG72, TLP, or TPS.

In various specific embodiments, the tumor-associated antigen or tumor-specific antigen is an AML-related tumor antigens, as described in S. Anguille et al, *Leukemia* (2012), 26, 2186-2196.

Other tumor-associated and tumor-specific antigens are known to those in the art.

Receptors, antibodies, and scFvs that bind to TSAs and TAAs, useful in constructing chimeric antigen receptors, are known in the art, as are nucleotide sequences that encode them.

In certain specific embodiments, the antigen recognized by the extracellular domain of a chimeric antigen receptor is an antigen not generally considered to be a TSA or a TAA, but which is nevertheless associated with tumor cells, or damage caused by a tumor. In certain embodiments, for example, the antigen is, e.g., a growth factor, cytokine or interleukin, e.g., a growth factor, cytokine, or interleukin associated with angiogenesis or vasculogenesis. Such growth factors, cytokines, or interleukins can include, e.g., vascular endothelial growth factor (VEGF), basic fibroblast growth factor (bFGF), platelet-derived growth factor (PDGF), hepatocyte growth factor (HGF), insulin-like growth factor (IGF), or interleukin-8 (IL-8). Tumors can also create a hypoxic environment local to the tumor. As such, in other specific embodiments, the antigen is a hypoxia-associated factor, e.g., HIF-1$\alpha$, HIF-1$\beta$, HIF-2$\alpha$, HIF-2$\beta$, HIF-3$\alpha$, or HIF-3$\beta$. Tumors can also cause localized damage to normal tissue, causing the release of molecules known as damage associated molecular pattern molecules (DAMPs; also known as alarmins). In certain other specific embodiments, therefore, the antigen is a DAMP, e.g., a heat shock protein, chromatin-associated protein high mobility group box 1 (HMGB 1), S100A8 (MRP8, calgranulin A), S100A9 (MRP14, calgranulin B), serum amyloid A (SAA), or can be a deoxyribonucleic acid, adenosine triphosphate, uric acid, or heparin sulfate.

Transmembrane domain: In certain embodiments, the extracellular domain of the CAR is joined to the transmembrane domain of the polypeptide by a linker, spacer or hinge polypeptide sequence, e.g., a sequence from CD28 or a sequence from CTLA4. The transmembrane domain can be obtained or derived from the transmembrane domain of any transmembrane protein, and can include all or a portion of such transmembrane domain. In specific embodiments, the transmembrane domain can be obtained or derived from, e.g., CD8, CD16, a cytokine receptor, and interleukin receptor, or a growth factor receptor, or the like.

Intracellular signaling domains: In certain embodiments, the intracellular domain of a CAR is or comprises an intracellular domain or motif of a protein that is expressed on the surface of T cells and triggers activation and/or proliferation of said T cells. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3ζ) or ITAM-containing portions thereof. In a specific embodiment, the intracellular domain is a CD3ζ intracellular signaling domain. In other specific embodiments, the intracellular domain is from a lymphocyte receptor chain, a TCR/CD3 complex protein, an Fc receptor subunit or an IL-2 receptor subunit. In certain embodiments, the CAR additionally comprises one or more co-stimulatory domains or motifs, e.g., as part of the intracellular domain of the polypeptide. The one or more co-stimulatory domains or motifs can be, or can comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif, or any combination thereof.

The CAR may also comprise a T cell survival motif. The T cell survival motif can be any polypeptide sequence or motif that facilitates the survival of the T lymphocyte after stimulation by an antigen. In certain embodiments, the T cell survival motif is, or is derived from, CD3, CD28, an intracellular signaling domain of IL-7 receptor (IL-7R), an intracellular signaling domain of IL-12 receptor, an intracellular signaling domain of IL-15 receptor, an intracellular signaling domain of IL-21 receptor, or an intracellular signaling domain of transforming growth factor β (TGFβ) receptor.

The modified immune cells expressing the CARs can be, e.g., T lymphocytes (T cells, e.g., CD4+ T cells or CD8+ T cells), cytotoxic lymphocytes (CTLs) or natural killer (NK) cells. T lymphocytes used in the compositions and methods provided herein may be naive T lymphocytes or MHC-restricted T lymphocytes. In certain embodiments, the T lymphocytes are tumor infiltrating lymphocytes (TILs). In certain embodiments, the T lymphocytes have been isolated from a tumor biopsy, or have been expanded from T lymphocytes isolated from a tumor biopsy. In certain other embodiments, the T cells have been isolated from, or are expanded from T lymphocytes isolated from, peripheral blood, cord blood, or lymph. Immune cells to be used to generate modified immune cells expressing a CAR can be isolated using art-accepted, routine methods, e.g., blood collection followed by apheresis and optionally antibody-mediated cell isolation or sorting.

The modified immune cells are preferably autologous to an individual to whom the modified immune cells are to be administered. In certain other embodiments, the modified immune cells are allogeneic to an individual to whom the modified immune cells are to be administered. Where allogeneic T lymphocytes or NK cells are used to prepare modified T lymphocytes, it is preferable to select T lymphocytes or NK cells that will reduce the possibility of graft-versus-host disease (GVHD) in the individual. For example, in certain embodiments, virus-specific T lymphocytes are selected for preparation of modified T lymphocytes; such lymphocytes will be expected to have a greatly reduced native capacity to bind to, and thus become activated by, any recipient antigens. In certain embodiments, recipient-mediated rejection of allogeneic T lymphocytes can be reduced by co-administration to the host of one or more immunosuppressive agents, e.g., cyclosporine, tacrolimus, sirolimus, cyclophosphamide, or the like.

T lymphocytes, e.g., unmodified T lymphocytes, or T lymphocytes expressing CD3 and CD28, or comprising a polypeptide comprising a CD3ζ signaling domain and a CD28 co-stimulatory domain, can be expanded using antibodies to CD3 and CD28, e.g., antibodies attached to beads; see, e.g., U.S. Pat. Nos. 5,948,893; 6,534,055; 6,352,694; 6,692,964; 6,887,466; and 6,905,681.

The modified immune cells, e.g., modified T lymphocytes, can optionally comprise a "suicide gene" or "safety switch" that enables killing of substantially all of the modified immune cells when desired. For example, the modified T lymphocytes, in certain embodiments, can comprise an HSV thymidine kinase gene (HSV-TK), which causes death of the modified T lymphocytes upon contact with gancyclovir. In another embodiment, the modified T lymphocytes comprise an inducible caspase, e.g., an inducible caspase 9 (icaspase9), e.g., a fusion protein between caspase 9 and human FK506 binding protein allowing for dimerization using a specific small molecule pharmaceutical. See Straathof et al., Blood 1 05(11):4247-4254 (2005).

In certain embodiments, Compound 1, Compound 2 or Compound 3 as provided herein and a second active agent provided herein are administered to patients with various types or stages of multiple myeloma in combination with chimeric antigen receptor (CAR) T-cells. In certain embodiments the CAR T cell in the combination targets B cell maturation antigen (BCMA), and in more specific embodiments, the CAR T cell is bb2121 or bb21217. In some embodiments, the CAR T cell is JCARH125.

J. Pharmaceutical Compositions

The pharmaceutical compositions provided herein contain therapeutically effective amounts of one or more of compounds provided herein and/or a second active agent provided herein, and optionally a pharmaceutically acceptable carrier, diluent or excipient.

The compounds can be formulated into suitable pharmaceutical preparations such as solutions, suspensions, tablets, dispersible tablets, pills, capsules, powders, sustained release formulations or elixirs, for oral administration or in sterile solutions or suspensions for ophthalmic or parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Seventh Edition 1999).

In the compositions, effective concentrations of one or more compounds or pharmaceutically acceptable salts is (are) mixed with a suitable pharmaceutical carrier or vehicle. In certain embodiments, the concentrations of the compounds in the compositions are effective for delivery of an amount, upon administration, that treats, prevents, or ameliorates one or more of the symptoms and/or progression of multiple myeloma.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as known in the art. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, tissue distribution, inactivation, metabolism and excretion rates of the active compound, the physicochemical characteristics of the compound, the dosage schedule, and amount administered as well as other factors known to those of skill in the art. For example, the amount that is delivered is sufficient to ameliorate one or more of the symptoms of cancer, including solid tumors and blood borne tumors.

Solutions or suspensions used for parenteral, intradermal, subcutaneous, or topical application can include any of the following components: a sterile diluent, such as water for injection, saline solution, fixed oil, polyethylene glycol, glycerine, propylene glycol, dimethyl acetamide or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, pens, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil water emulsions containing suitable quantities of the compounds or pharmaceutically acceptable salts thereof. The pharmaceutically therapeutically active compounds and salts thereof are formulated and administered in unit dosage forms or multiple dosage forms. Unit dose forms as used herein refer to physically discrete units suitable for human and animal subjects and packaged individually as is known in the art. Each unit dose contains a predetermined quantity of the therapeutically active compound sufficient to produce the desired therapeutic effect, in association with the required pharmaceutical carrier, vehicle or diluent. Examples of unit dose forms include ampules and syringes and individually packaged tablets or capsules. Unit dose forms may be administered in fractions or multiples thereof. A multiple dose form is a plurality of identical unit dosage forms packaged in a single container to be administered in segregated unit dose form. Examples of multiple dose forms include vials, bottles of tablets or capsules or bottles of pints or gallons. Hence, multiple dose form is a multiple of unit doses which are not segregated in packaging.

Dosage forms or compositions containing active ingredient in the range of 0.005% to 100% with the balance made up from non toxic carrier may be prepared. For oral administration, a pharmaceutically acceptable non toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art.

The active compounds or pharmaceutically acceptable salts may be prepared with carriers that protect the compound against rapid elimination from the body, such as time release formulations or coatings.

The compositions may include other active compounds to obtain desired combinations of properties. The compounds provided herein, or pharmaceutically acceptable salts thereof as described herein, may also be advantageously administered for therapeutic or prophylactic purposes together with another pharmacological agent known in the general art to be of value in treating one or more of the diseases or medical conditions referred to hereinabove, such as diseases related to oxidative stress. It is to be understood that such combination therapy constitutes a further aspect of the compositions and methods of treatment provided herein.

K. Evaluation of the Activity and Properties of the Combination

Standard physiological, pharmacological and biochemical procedures are available for testing the compounds to identify those that possess the desired properties, including anti-multiple myeloma proliferative activity and adequate safety profile. Such assays include, for example, biochemical assays such as binding assays, radioactivity incorporation assays, as well as a variety of cell based assays.

Isoindolinone derivatives and their therapeutic uses have been described in for example, U.S. Pat. No. 8,518,972. Surprisingly, Compound 1, Compound 2 and Compound 3 exhibit unexpected and beneficial properties, as shown in the Examples section. These beneficial properties include significantly increased anti-multiple myeloma potency, increased levels of apoptosis, and the more potent and efficacious combination response with dexamethasone, and surprisingly an improved safety profile, as shown by reduced functional activity at the α1 adrenergic and D2 dopamine receptors (in vitro, as well as in vivo), improved cell killing selectivity (as shown by reduced killing of non-myeloma cells), and reduced CYP3A4 inhibition. Additionally, Compound 1, Compound 2 and Compound 3 exhibit unexpected synergy when used in combination with the second active agents, as shown in the Examples section.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

5. EXAMPLES

Certain embodiments of the invention are illustrated by the following non-limiting examples.

Abbreviations

AcN/ACN Acetonitrile

AIBN Azobisisobutyronitrile

Boc tert-Butyloxycarbonyl $Boc_2O$ di-tert-Butyl dicarbonate tBuOK Potassium tert-butoxide DIEA Diisopropylethylamine DMF N,N'-Dimethylformamide DMSO Dimethylsulfoxide EtOAc Ethyl acetate IPA Isopropanol or 2-propanol MeOH Methanol MM Multiple Myeloma NBS N-bromosuccinimide, NMR Nuclear Magentic Resonance PBMC Human peripheral blood mononuclear cell i-PrOAc Isopropyl acetate TBS tert-Butyl dimethylsilyl TBSCl tert-Butyl dimethylsilylchloride THF Tetrahydrofuran TLC Thin layer chromatography TMSCl Trimethylsilyl chloride Example 1: Synthesis of (S)-4-(4-(4-(((2-(2,6-di-oxopiperidin-3-yl)-1-oxoisoindolin-4-yl)oxy)methyl)benzyl)piperazin-1-yl)-3-fluorobenzonitrile (Compound 2)

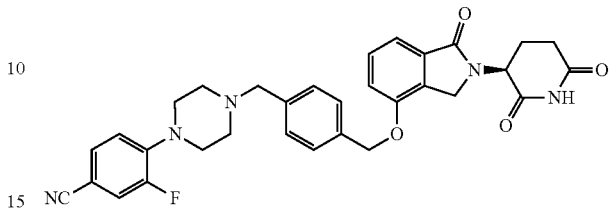

tert-Butyl (4S)-5-amino-4-(benzyloxycarbonylamino)-5-oxo-pentanoate

To a solution of (2S)-2-(benzyloxycarbonylamino)-5-tert-butoxy-5-oxo-pentanoic acid (150 g, 445 mmol) in 1,4-dioxane (1.50 L) was added di-tert-butyl dicarbonate (155 g, 711 mmol), pyridine (70.3 g, 889 mmol) and ammonium bicarbonate (105 g, 1.33 mol). The reaction mixture was stirred at 18° C. for 16 h and then concentrated. The residue was dissolved in ethyl acetate (5.0 L) and water (5.0 L), the organic layer was separated and washed with HCl (3.0 mL, 1 N), saturated sodium bicarbonate (3.0 L), brine (3.0 L), dried over anhydrous sodium sulfate, filtered and concentrated to give crude tert-butyl (4S)-5-amino-4-(benzyloxycarbonylamino)-5-oxo-pentanoate (450 g, crude) as a white solid, which was used in the next step without further purification. $^1$H NMR 400 MHz DMSO-$d_6$ δ: 7.35-7.30 (m, 5H), 7.02 (s, 1H), 5.01 (d, J=3.2 Hz, 1H), 3.93-3.90 (m, 1H), 2.20 (t, J=8.0 Hz, 2H), 1.88-1.84 (m, 1H), 1.72-1.69 (m, 1H), 1.35 (s, 9H).

tert-Butyl (4S)-4,5-diamino-5-oxo pentanoate. To a solution of tert-butyl (4S)-5-amino-4-(benzyloxycarbonylamino)-5-oxo-pentanoate (112 g, 333 mmol) in methanol (1.0 L) was added 10% palladium on carbon (15 g) under nitrogen. The suspension was degassed under vacuum and purged with hydrogen several times. The mixture was stirred under hydrogen gas (40 psi) at 30° C. for 16 h. The reaction mixture was filtered and the filtrate was concentrated to give crude tert-butyl (4S)-4,5-diamino-5-oxo-pentanoate as a colorless oil. $^1$H NMR 400 MHz DMSO-$d_6$ δ: 7.30 (s, 1H), 6.95 (s, 1H), 3.10-3.07 (m, 1H), 2.27-2.23 (m, 2H), 1.69-1.78 (m, 1H), 1.59-1.55 (m, 1H), 1.38 (s, 9H).

Methyl 3-hydroxy-2-methyl-benzoate

Four batches (200 g each) were run in parallel. To a solution of 3-hydroxy-2-methyl-benzoic acid (200 g, 1.31 mol) in methanol (4.0 L) was added concentrated sulfuric acid (47.7 g, 486 mmol). The reaction mixture was stirred at 60° C. for 17 h. The reaction mixture was concentrated to 800 mL. The resulting mixture was cooled to 20° C. and slowly poured into water (400 mL) over 30 mins. Water (1200 mL) was added at 20° C. over 3 h and the resulting mixture was stirred at 20° C. for 1 h. The precipitated solid was collected by vacuum filtration (four batches combined) and was washed three times with water/methanol (1000 mL, 9:1) or until the filtrate had pH >3. The solid was dried under vacuum at 45° C. to give methyl 3-hydroxy-2-methyl-benzoate (700 g, 80.4% yield) as a gray solid. $^1$H NMR: 400 MHz DMSO-$d_6$ δ: 9.70 (s, 1H), 7.18 (t, J=6.8 Hz, 1H), 7.09 (t, J=7.6 Hz, 1H), 7.00 (t, J=6.8 Hz, 1H), 3.81 (s, 3H), 2.29 (s, 3H).

Methyl 3-[tert-butyl(dimethyl)silyl]oxy-2-methyl-benzoate

Two batches (240 g each) were run in parallel. To a solution of methyl 3-hydroxy-2-methyl-benzoate (240 g, 1.44 mol) in N,N-dimethylformamide (1.40 L) were added imidazole (246 g, 3.61 mol) and tert-butyl dimethylsilyl chloride (238 g, 1.58 mol) at 5° C. After addition, the mixture was warmed up to 20° C. and stirred for 6 h. Isopropyl acetate (1700 mL) was added, and then water (2000 mL) was slowly added while the temperature was kept under 30° C. The resulting mixture was stirred followed by separation of the organic phase. The combined organics (two batches combined) were washed with water (1700 mL×3) and concentrated to ~1500 mL (KF<0.05%). The product was stored as an isopropyl acetate solution which was used in the next step without further purification.

Methyl 2-(bromomethyl)-3-[tert-butyl(dimethyl)silyl]oxy-benzoate

Two batches (~375 g each) were run in parallel. To the isopropyl acetate solution of methyl 3-[tert-butyl(dimethyl)silyl]oxy-2-methyl-benzoate (~375 g, 1.34 mol) was added N-bromosuccinimide (274 g, 1.54 mol) and azobisisobutyronitrile (4.40 g, 26.8 mmol). The reaction mixture was heated to 70° C. over at least 1 h and stirred at 70° C. for 4 h. The reaction mixture was cooled to 20° C. and held at 20° C. for at least 1 h. The two batches of solid (succinimide) were removed by filtration and washed with isopropyl acetate (700 mL). The filtrate was washed with solution of sodium sulfite (700 g) in water (6000 mL), followed by water (1500 mL). The organic layer was distilled under vacuum at 45° C. to dryness to give methyl 2-(bromomethyl)-3-[tert-butyl(dimethyl)silyl]oxy-benzoate (920 g, 95.5% yield) as dark orange oil. $^1$H NMR: 400 MHz DMSO-$d_6$ δ: 7.45 (d, J=6.8 Hz, 1H), 7.36 (t, J=8.0 Hz, 1H), 7.13 (t, J=7.2 Hz, 1H), 4.95 (s, 2H), 1.02 (s, 9H), 0.29 (s, 6H).

tert-Butyl (4S)-5-amino-4-[4-[tert-butyl(dimethyl)silyl]oxy-1-oxo-isoindolin-2-yl]-5-oxo-pentanoate To a solution of tert-Butyl (4S)-4,5-diamino-5-oxo-pentanoate (130 g, 643 mmol) in acetonitrile (4.0 L) was added methyl 2-(bromomethyl)-3-[tert-butyl(dimethyl)silyl]oxy-benzoate (210 g, 584 mmol) and diisopropylethylamine (113 g, 877 mmol). The reaction mixture was stirred at 50° C. for 16 h. The reaction mixture was concentrated to remove most of the acetonitrile, the residue was dissolved in methyl tert-butyl ether (2.0 L) and water (1.5 L), the organic layer was washed with saturated monopotassium phosphate (1.0 L×2), brine (1.0 L), dried over anhydrous sodium sulfate, filtered and concentrated to give crude tert-butyl (4S)-5-amino-4-[4-[tert-butyl(dimethyl)silyl]oxy-1-oxo-isoindolin-2-yl]-5-oxo-pentanoate (524 g), which was used into next step without further purification.

tert-Butyl (4S)-5-amino-4-(4-hydroxy-1-oxo-isoindolin-2-yl)-5-oxo-pentanoate

To a solution of tert-butyl (4S)-5-amino-4-[4-[tert-butyl(dimethyl)silyl]oxy-1-oxo-isoindolin-2-yl]-5-oxo-pentanoate (275 g, 613 mmol) in methanol (2.0 L) was added tetrabutylammonium fluoride trihydrate (38.7 g, 123 mmol). The mixture was stirred at 18° C. for 16 h. The reaction mixture was concentrated to remove most of the methanol, and the residue was dissolved in dichloromethane/water (3 L/2 L). The organic layer was separated and washed with brine (1.0 L), dried over anhydrous sodium sulfate, filtered, and concentrated to give crude product, which was purified by silica gel column to give product (260 g). Product was added into acetonitrile (750 mL) and the mixture was stirred at 60° C. for 2 h, cooled to 18° C., and stirred for another 2 h. The solid was filtered and the cake was dried to give tert-butyl (4S)-5-amino-4-(4-hydroxy-1-oxo-isoindolin-2-yl)-5-oxo-pentanoate (248 g, 60.5% yield) as a gray solid. $^1$H NMR 400 MHz DMSO-$d_6$ δ: 10.00 (s, 1H), 7.54 (s, 1H), 7.29 (t, J=7.6 Hz, 1H), 7.14 (d, J=4.8 Hz, 2H), 4.72-4.68 (m, 1H), 4.49-4.28 (m, 2H), 2.17-1.97 (m, 4H), 1.31 (s, 9H).

4-(4-(4-(chloromethyl)benzyl)piperazin-1-yl)-3-fluorobenzonitrile 1,4-bis(chloromethyl)benzene (51.2 g, 292 mmol) was placed in a flask with acetonitrile (195 mL) and N,N-dimethylformamide (195 mL). The reaction mixture was stirred at ambient temperature until all the solids dissolved. Diisopropylamine (51.1 mL, 292 mmol) was then added along with 3-fluoro-4-(piperazin-1-yl)benzonitrile (20 g, 97 mmol). The reaction was heated to 60° C. for 1 h. The acetonitrile was removed under reduced pressure. The remaining mixture was partitioned between ethyl acetate (1.0 L), water (700 mL), and brine (300 mL). The organic layer was separated and the aqueous layer was extracted with ethyl acetate twice. Volatile organics were combined and removed under reduced pressure. The solid was dissolved in minimal dichloromethane and purified on silica gel column (0-100% ethyl acetate in hexanes over 3 L). Fractions containing desired product were combined and volatile organics were removed under reduced pressure. The residue was dissolved in minimal dichloromethane and purified a second time on silica gel column (10% isocratic ethyl acetate in hexanes over 800 mL followed by 20-80% ethyl acetate in hexanes over 4 L). Fractions containing desired product were combined and volatile organics were removed under reduced pressure to afford 4-(4-(4-(chloromethyl)benzyl)piperazin-1-yl)-3-fluorobenzonitrile (22.7 g, 66.0 mmol, 67.7% yield) as an off-white solid. $^1$H NMR (400 MHz, CDCl$_3$) δ ppm 7.33-7.39 (m, 5H) 7.29 (d, J=1.96 Hz, 1H) 7.25 (d, J=1.96 Hz, 1H) 6.91 (t, J=8.56 Hz, 1H) 4.60 (s, 2H) 3.58 (s, 2H) 3.19-3.27 (m, 4H) 2.58-2.66 (m, 4H). MS (ESI) m/z 344.2 [M+1]$^+$.

(S)-tert-butyl 5-amino-4-(4-((4-((4-(4-cyano-2-fluorophenyl)piperazin-1-yl)methyl)benzyl)oxy)-1-oxoisoindolin-2-yl)-5-oxopentanoate (S)-tert-butyl 5-amino-4-(4-hydroxy-1-oxoisoindolin-2-yl)-5-oxopentanoate (22.05 g, 65.9 mmol) was placed in a flask with 4-(4-(4-(chloromethyl)benzyl)piperazin-1-yl)-3-fluorobenzonitrile (22.67 g, 65.9 mmol), potassium carbonate (18.23 g, 132 mmol), and N,N-dimethylformamide (330 mL). The reaction mixture was heated to 45° C. for 16 h. The reaction was diluted with ethyl acetate (50 mL) and filtered. The filtrate was partitioned with ethyl acetate (900 mL) and water (600 mL) and brine (200 mL). The organic layer was isolated and washed with water (600 mL). The organic layer was dried over sodium sulfate, and volatiles were removed under reduced pressure. The residue was treated with 20% ethyl acetate in hexanes and volatiles were removed under reduced pressure to afford (S)-tert-butyl 5-amino-4-(4-((4-((4-(4-cyano-2-fluorophenyl)piperazin-1-yl)methyl)benzyl)oxy)-1-oxoisoindolin-2-yl)-5-oxopentanoate (44.02 g, 68.6 mmol, 104% yield) as an off-white solid. Yield was slightly over quantitative as some DMF remained. $^1$H NMR (400 MHz, CDCl$_3$) δ ppm 7.43-7.49 (m, 2H) 7.40 (s, 4H) 7.36 (dd, J=8.38, 1.28 Hz, 1H) 7.29 (d, J=1.96 Hz, 1H) 7.26 (d, J=1.83 Hz, 1H) 7.11 (dd, J=7.64, 1.16 Hz, 1H) 6.92 (t, J=8.50 Hz, 1H) 6.23 (br s, 1H) 5.24-5.32 (m, 1H) 5.15 (s, 2H) 4.86-4.94 (m, 1H) 4.38-4.55 (m, 2H) 3.61 (s, 2H) 3.18-3.32 (m, 4H) 2.58-2.70 (m, 4H) 2.09-2.47 (m, 4H) 1.43 (s, 8H). MS (ESI) m/z 642.4 [M+1]$^+$.

(S)-4-(4-(4-(((2-(2,6-Dioxopiperidin-3-yl)-1-oxoisoindolin-4-yl)oxy)methyl)benzyl)piperazin-1-yl)-3-fluorobenzonitrile (Compound 2)

(S)-tert-butyl 5-amino-4-(4-((4-((4-(4-cyano-2-fluorophenyl)piperazin-1-yl)methyl)benzyl)oxy)-1-oxoisoindolin-2-yl)-5-oxopentanoate (12.1 g, 18.86 mmol) was placed in a vial with acetonitrile (189 mL) and benzenesulfonic acid (3.96 g, 24.51 mmol). The reaction mixture was placed under vacuum and purged with nitrogen. This was repeated once more and the mixture was then heated to 85° C. overnight under a nitrogen atmosphere. The warm reaction mixture was poured directly into 2 separatory funnels containing dichloromethane (1000 mL) and ethyl acetate (300 mL). To this mixture a saturated solution of sodium bicarbonate (900 mL), water (100 mL), and brine (450 mL) was added. The organic layer was isolated and the aqueous layer was extracted with dichloromethane (800 mL) and ethyl acetate (200 mL). The combined organic layers were dried over anhydrous magnesium sulfate, and concentrated. Purification by standard methods provided the title compound. $^1$H NMR (400 MHz, DMSO-d$_6$) δ ppm 10.96 (s, 1H) 7.68 (dd, J=13.45, 1.83 Hz, 1H) 7.56 (dd, J=8.44, 1.83 Hz, 1H) 7.43-7.52 (m, 3H) 7.29-7.39 (m, 4H) 7.11 (t, J=8.80 Hz, 1H) 5.24 (s, 2H) 5.11 (dd, J=13.20, 5.14 Hz, 1H) 4.22-4.46 (m, 2H) 3.54 (s, 2H) 3.12-3.22 (m, 4H) 2.85-2.97 (m, 1H) 2.53-2.62 (m, 2H) 2.38-2.48 (m, 2H) 1.93-2.03 (m, 1H). MS (ESI) m/z 568.2 [M+1]$^+$.

Example 2: Antiproliferative Effects on Multiple Myeloma

Cell Culture Materials: Human multiple myeloma cell lines were purchased from the vendors and cultured at 37° C. with 5% CO$_2$ in the media as indicated in Table 1. Lenalidomide and pomalidomide resistant cell lines were obtained by methods as generally described previously (Lopez-Girona et al Leukemia 2012; 26(11): 2335). All cell lines were kept in log phase, and cell density and viability were monitored by trypan blue exclusion using the Vi-cell XR cell viability analyzer (Beckman Coulter, Brea, Calif.).

TABLE 1

Multiple Myeloma Cell Lines Tested

| MM Cell Line | Vendor/Source | Catalog Number | Culture Conditions |
|---|---|---|---|
| NCI-H929 | ATCC (Manassas, VA) | CRL-9068 | RPMI-1640, 10% FBS |
| NCI-H929-1051 | developed in-house, made resistant to lenalidomide | NA | RPMI-1640, 10% FBS |
| OPM2 | DSMZ (Braunschweig, Germany) | ACC-50 | RPMI-1640, 10% FBS |
| OPM2-P10 | developed in-house, made resistant to 10 μM pomalidomide | NA | RPMI-1640, 10% FBS |

Preparation of Solutions of Test Article:
Compounds were plated into black 384-well plates (Corning Inc.) to a final DMSO volume of 0.1% assuming a maximal volume of 50 μL. A 10-point dose response starting at 10 μM with a 1:3 dilution was printed in duplicate by acoustic dispense using the EDC ATS-100 platform. Alternatively, the 10-point dose response starting at 10 μM with a 1:10 dilution, or starting at 100 nM with a 1:3 dilutions were used.

Cell Proliferation Assays:
The effect of compounds on the proliferation/viability of the hematological cell lines (Table 1), was assessed after 120 h incubation using CTG (Promega), according to manufacturer's instructions. Hematological cell lines were dispensed into compound plates by a Multidrop Combi Reagent Dispenser (Thermo Scientific, Waltham, Mass.) at a concentration of 0.1×10$^6$ cells per mL in a 50 μL total volume. At 120 h, 25 μL per well of CTG was dispensed by a Multidrop Combi Reagent Dispenser and adenosine triphosphate (ATP) release by viable cells was measured as relative luminescence units after 30 minutes using the Envision platform.

Results. Compound 1 and Compound 2 Demonstrate Antiproliferative Activity Against MM Cell Lines.

The MM cell lines selected for this study were lines sensitive and resistant to lenalidomide and/or pomalidomide (Table 1), two agents used in the clinic to treat myeloma patients. Proliferation was assessed using the CellTitre-Glo® assay. Results for cultures incubated with the compounds were normalized to results for control cultures for each cell line. The IC$_{50}$ for inhibition of cell growth by the compounds was determined for each cell line using ActivityBase software. Compound 1 and Compound 2 potently inhibited cell proliferation in the four cell lines, as determined by the quantitative assessment of ATP levels present in the media after 120 h. The antiproliferative IC$_{50}$ values of Compound 1 and Compound 2 ranged between 0.07 nM and 19 nM (Table 2). Compound 1 and Compound 2 showed very potent multiple myeloma anti-proliferative activity even on cell lines that were lenalidomide- and/or pomalidomide-resistant.

TABLE 2

Inhibition of Cell Growth by Compound 1 and Compound 2 in a MM Cell Lines in Liquid Culture

| Compd. No. | NCI-H929 120 h IC$_{50}$ | NCI-H929.1051 120 h IC$_{50}$ | OPM-2 120 h IC$_{50}$ | OPM-2.P10 120 h IC$_{50}$ |
|---|---|---|---|---|
| 1 | <0.5 nM | 2.5 nM | <0.5 nM | 19 nM |
| 2 | 0.07 nM | 1.0 nM | 0.07 nM | 4.3 nM |

Example 3: Off-Target Effects of Compound 1/Compound 2 and Implications

α1 Adrenergic and Dopamine D2 Receptors.

Methods: Binding and functional assays for α1 adrenergic and dopamine D2 receptors were performed by Eurofins Cerep according to their methods.

α1 Adrenergic Receptor. Binding at 10 μM.

The binding assay evaluated the affinity of test article for the non-selective α1 adrenergic receptor in rat cerebral cortex. Membrane homogenates of cerebral cortex were incubated in duplicate for 60 minutes at room temperature with 0.25 nM [$^3$H]prazosin in the absence or presence of test articles at 10 μM. After the incubation period, samples were filtered through glass fiber filters, the filters dried and then counted for radioactivity using a scintillation counter. Results are expressed as mean percent inhibition of control radioligand binding.

Binding $IC_{50}$. To determine the binding $IC_{50}$ for the non-selective α1 adrenergic receptor, varying concentrations of test article were incubated in duplicate with 0.25 nM [$^3$H]prazosin. Previously reported compound 3-(4-((4-((4-(2,4-difluorophenyl)piperazin-1-yl)methyl)benzyl)oxy)-1-oxoisoindolin-2-yl)piperidine-2,6-dione (Example 5.285 in U.S. Pat. No. 8,518,972) (Compound A) was tested at 0.01-30 μM. Compound B, the S-enantiomer of Compound A, was tested at 0.0003-10 μM. Compound 1 and Compound 2, the S-enantiomer of Compound 1, were assayed at 0.03-100 μM. Radioactivity was measured as described above. The $IC_{50}$ was defined as the concentration causing a half-maximum inhibition of control specific binding.

Antagonist activity. The antagonistic effects of test compounds on the $α_{1A}$ and $α_{1B}$ adrenergic receptors were measured using human receptor-transfected Chinese hamster ovary (CHO) cells. Antagonist activity was determined by measuring compound effect on agonist (epinephrine)-induced calcium mobilization in the $α_{1A}$ receptor assay or cAMP levels in the $α_{1B}$ receptor assay. In these experiments, CHO cells were incubated in duplicate at room temperature with test article and epinephrine at 3 nM in the $α_{1A}$ receptor assays or at 3000 nM in the $α_{1B}$ receptor assay. Compound A was tested in the $α_{1A}$ receptor assay at 0.01-30 μM. Compound B was tested in the $α_{1A}$ and $α_{1B}$ receptor assays at 0.0003-30 μM. Compound 1 and Compound 2 were assayed at 0.03 to 30 μM in the $α_{1A}$ receptor assay and 0.03 to 100 μM in the $α_{1B}$ receptor assay. In the $α_{1A}$ receptor assay, cytosolic calcium levels were measured fluorometrically using the fluorescent probe, Fluo4 Direct. Intracellular cAMP levels in the $α_{1B}$ adrenergic receptor assay were measured by homogenous time-resolved fluorescence (HTRF). The antagonism $IC_{50}$ was defined as the concentration causing a half-maximum inhibition of control agonist response.

Dopamine D2 Receptor.

Binding at 10 μM. The binding assay evaluated the affinity of test articles for the dopamine D2 receptor in transfected human embryonic kidney (HEK)-293 cells. For determining the binding in the $D_{2S}$ receptor assay, test article was incubated with 0.3 nM [$^3$H] methylspiperone or 1 nM [$^3$H] 7-hydroxy-2-N,N-dipropylaminotetralin (7-OH-DPAT). [$^3$H] Methylspiperone at 0.3 nM also was used as control ligand in the $D_{2L}$ binding assay. Cell membrane homogenates were incubated in duplicate at room temperature for 60 minutes with ligand in the absence or presence of test articles at 10 μM. After the incubation period, samples were filtered through glass fiber filters, the filters dried and then counted for radioactivity using a scintillation counter. Results are expressed as mean percent inhibition of control radioligand binding.

Binding $IC_{50}$. To determine the binding $IC_{50}$ in the D2 receptor assays, HEK-293 were tested as described above but with varying concentrations of test article. Compound A was tested at 0.01-30 μM in the $D_{2S}$ radioligand binding assay. Compound B was tested at 0.0003-10 μM in both the $D_{2S}$ and $D_{2L}$ binding assays. Compound 1 was assayed at 0.03-100 μM in both the $D_{2S}$ and $D_{2L}$ assays, while Compound 2 was tested at 0.03-100 μM in the $D_{2S}$ assay and 0.01-100 μM in the $D_{2L}$ assays. The $IC_{50}$ was defined as the concentration causing a half-maximum inhibition of control specific binding.

Agonist activity. The agonism of test compounds on the dopamine $D_{2S}$ receptor was assessed using human receptor-transfected HEK-293 cells. Agonist activity was determined by measuring compound effect on impedance modulation. In these experiments, HEK-293 cells were incubated in duplicate at 28° C. with test article. Compound A was tested at 0.01-30 μM. Compound B was tested at 0.0003-10 μM, while Compound 1 and Compound 2 were assayed at 0.01-10 μM. Dopamine (3 μM) was used as an agonist control. Impedance measurements were monitored for 10 minutes after ligand addition using cellular dielectric spectroscopy. The $EC_{50}$ was defined as the concentration causing a half-maximum response, compared to the control agonist (dopamine) response.

Results.

Binding at 10 μM at the α1 adrenergic and dopamine D2 receptors was evaluated for Compound 1, Compound 2, Compound A, Compound B and a number of compounds exemplified in U.S. Pat. No. 8,518,972 (as indicated by their example number Ex.) (Table 3). While the previously disclosed compounds fully inhibited binding of ligand at both receptors, surprisingly, Compound 1 and Compound 2 showed greatly diminished ability to inhibit ligand binding, showing only 67/62% (α1 adrenergic receptor) and 55/52% (dopamine $D_{2S}$) inhibition of ligand binding, respectively.

TABLE 3

Effects of Compound A, Compound B, Compound 1 and Compound 2 and previously reported compounds on α1 Adrenergic and Dopamine D2 Receptor

| Cmpd No. | $R^1$ | $R^2$ | X | Stereo | Adrenergic α1 % Inh. (@10 μm) | Dopamine $D_{2S}$ % Inh. (@10 μm) |
|---|---|---|---|---|---|---|
| 1 | CN | F | $CH_2$ | rac | 67 | 55 |
| 2 | CN | F | $CH_2$ | S | 62 | 52 |
| A | F | F | $CH_2$ | rac | 102 | 99 |
| B | F | F | $CH_2$ | S | 98 | 99 |
| Ex. 5.229 | H | H | $CH_2$ | rac | 98.3 | 98.7 |
| Ex. 5.273 | F | H | $CH_2$ | rac | 100.3 | 94.7 |
| Ex. 5.289 | F | H | CO | rac | 97.9 | 92.4 |

Example 4: Effect of Compound 2 in Combination with Small Molecule Inhibitors

The effect of combining treatment with Compound 2 and small molecule inhibitors with various mechanisms was evaluated in a panel of MM cell lines. Nine small molecule inhibitors were selected for combination studies with Compound 2 based on their preclinical and/or activity against MM. The cell lines H929-1051, KMS11, KMS-12PE, L363, OPM-P10, and RPMI8226 were selected for this study to represent the different genetic clustering groups across MM cell lines. Compound concentrations for the combination treatments were selected in the range of 1 log above and 2 logs below the $IC_{50}$ of the single agent. Combination agents were dosed in a 6 point dose-response curve (DRC) at a 1:3 dilution, Compound 2 was dosed in a 10 point DRC, also at a 1:3 dilution. The combination experiments were run twice, each time with replicate data on separate plates. Compounds were pre-spotted into the appropriate wells of 384-well plates using an acoustic dispenser. All MM cell lines were cultured in an incubator at 37° C. with 5% $CO_2$ using the indicated cell culture media containing 1× Penicillin-Streptomycin. Cells were added to the compound containing 384-well plates using a Multidrop Combi Reagent Dispenser and allowed to incubate for 3 days at 37° C. with 5% $CO_2$. After 3 days, cells were assessed for their level of ATP content via Cell Titer-Glo measured on a luminescence detector (PerkinElmer Envision).

The Highest Single Agent (HAS) method was used to detect synergy in the dose response curve data. Combinations were analyzed from a response surface perspective. A statistical framework (Van Der Borght, K., et al., BIGL: Biochemically Intuitive Generalized Loewe null model for prediction of the expected combined effect compatible with partial agonism and antagonism; *Scientific Reports*, 7 (1), 17935-1-17935-9 (2017)) was incorporated into the analysis on top of the HAS null model with two statistical tests: 1) Complete response surface differs from null model, 2) Single well differs from null model.

Results:

The effect of treatment with Compound 2 in combination with small molecule inhibitors was evaluated in a panel of multiple myeloma cell lines. Compound 2 was screened in combination with 9 compounds and the synergy was calculated across all wells for 6 cell lines, and the results are summarized in FIG. 1. Graph examples of data from selected studies are shown in FIG. 2A to FIG. 2I, respectively. PIM inhibitor LGH-447 showed synergy in combination with Compound 2 in all of the six cell lines tested. mTOR inhibitor everolimus showed synergy in combination with Compound 2 in five out of the six cell lines tested. IGF-1R inhibitor linsitinib showed synergy in combination with Compound 2 in four out of the six cell lines tested. Combination of Compound with BTK inhibitor ibrutinib, MEK inhibitor trametinib, XPO1 inhibitor selinexor, DOT L inhibitor SGC0946, EZH2 inhibitor EPZ-6438, and JAK2 inhibitor fedratinib showed synergy in one, two, or three out of the six cell lines tested. This data suggests that combination treatment with Compound 2 with the small molecule inhibitors tested represents a potential treatment paradigm for MM, including some with synergistic activity.

Example 5: Effect of Compound 2 in Combination with BRD4 Inhibitor

K12PE (parental) and K12PE-PR (pomalidomide resistant) cell lines were treated with various doses of Compound 2 in combination with increasing doses of a BRD4 inhibitor JQ1 for 3 days. Cell proliferation was analyzed using thymidine incorporation assays. Combination index values were calculated by Calcusyn and values below $10^0$ represented the synergy between the combination treatments. The results are shown in FIG. 3A (K12PE), FIG. 3B (K12PE combination index), FIG. 3C (K12PE-PR), and FIG. 3D (K12PE-PR combination index), respectively. BRD4 inhibitor (JQ1) demonstrates synergistic activity with Compound 2.

Example 6: Effect of Compound 2 in Combination with MEK Inhibitor

AMO1 (parental) and AMO1-PR (pomalidomide resistant) cell lines were treated with various doses of Compound 2 in combination with increasing doses of an MEK inhibitor trametinib for 3 days. Cell proliferation was analyzed using thymidine incorporation assays. Combination index values were calculated by Calcusyn and values below $10^0$ represented the synergy between the combination treatments. The results are shown in FIG. 4A (AMO1), FIG. 4B (AMO1 combination index), FIG. 4C (AMO1-PR), and FIG. 4D (AMO1-PR combination index), respectively. MEK inhibitor (trametinib) demonstrates synergistic activity with Compound 2.

Example 7: Effect of Compound 2 in Combination with EZH2 Inhibitor

H929 cell line was treated with various doses of Compound 2 in combination with increasing doses of an EZH2 inhibitor UNC1999 for 3 days. Cell proliferation was analyzed using thymidine incorporation assays. Combination index values were calculated by Calcusyn and values below $10^0$ represented the synergy between the combination treatments. The results are shown in FIG. 5A (H929) and FIG. 5B (H929 combination index). EZH2 inhibitor (UNC1999) demonstrates synergistic activity with Compound 2.

Example 8: Effect of Compound 2 in Combination with PLK1 Inhibitor

AMO1 and AMO1-PR (pomalidomide resistant) cell lines were treated with increasing doses of Compound 2 in combination with a PLK1 inhibitor (BI2536). Changes in cell proliferation were studied in response to monotherapy and combinations at Day 3 post treatment. Combination Index was calculated using Calcusyn based method. Combination index values were calculated by Calcusyn and values below $10^0$ represented the synergy between the combination treatments. PLK1 is one of the key target gene of MDMS8 (molecularly defined myeloma segment 8), a high risk cluster identified from myeloma genome project. The results are shown in FIG. 6A (AMO1), FIG. 6B (AMO1 combination index), FIG. 6C (AMO1-PR), and FIG. 6D (AMO1-PR combination index), respectively. Inhibition of MDMS8 target gene PLK1 with Compound 2 is synergistic in AMO1 and AMO1-PR cells.

Example 9: Effect of Compound 2 in Combination with NEK2 Inhibitor

AMO1 and AMO1-PR (pomalidomide resistant) cell lines were treated with increasing doses of Compound 2 in combination with an NEK2 inhibitor (JH295). Changes in cell proliferation were studied in response to monotherapy and combinations at Day 3 post treatment. Combination index values were calculated by Calcusyn and values below $10^0$ represented the synergy between the combination treatments. NEK2 is one of the key target gene of MDMS8 (molecularly defined myeloma segment 8), a high risk cluster identified from myeloma genome project. The results are shown in FIG. 7A (AMO1 combination index) and FIG. 7B (AMO1-PR combination index), respectively. Inhibition of MDMS8 target gene NEK2 with Compound 2 is synergistic in AMO1 and AMO1-PR cells.

Example 10: Effect of Compound 2 in Combination with AURKB Inhibitor

AMO1, AMO1-PR (pomalidomide resistant), K12PE and K12PE-PR (pomalidomide resistant) cell lines were treated with increasing doses of Compound 2 in combination with an AURKB inhibitor (AZD1152). Changes in cell proliferation were studied in response to monotherapy and combinations at Day 3 post treatment. Combination index values were calculated by Calcusyn and values below $10^0$ represented the synergy between the combination treatments. AUKKB is one of the key target gene of MDMS8 (molecularly defined myeloma segment 8), a high risk cluster identified from myeloma genome project. The results are shown in FIG. 8A (AMO1 combination index), FIG. 8B (K12PE combination index), FIG. 8C (AMO1-PR combination index), and FIG. 8D (K12PE-PR combination index), respectively. Inhibition of MDMS8 target gene AURKB with Compound 2 is synergistic in AMO1, AMO1-PR, K12PE, and K12PE-PR cells.

Example 11: Effect of Compound 2 in Combination with BIRC5 Inhibitor

AMO1, AMO1-PR (pomalidomide resistant) cell lines were treated with increasing doses of Compound 2 in combination with a BIRC5 inhibitor (YM155). Changes in cell proliferation were studied in response to monotherapy and combinations at Day 3 post treatment. Combination index values were calculated by Calcusyn and values below $10^0$ represented the synergy between the combination treatments. BIRC5 is one of the key target gene of MDMS8 (molecularly defined myeloma segment 8), a high risk cluster identified from myeloma genome project. The results are shown in FIG. 9A (AMO1), FIG. 9B (AMO1 combination index), FIG. 9C (AMO1-PR), and FIG. 9D (AMO1-PR combination index), respectively. Inhibition of MDMS8 target gene BIRC5 with Compound 2 is synergistic in AMO1 and AMO1-PR cells.

Example 12: Combination Studies with Additional Second Agents

Additional second agents, including DNA methyltransferase inhibitors, EZH2 inhibitors, DOT1L inhibitors, and BET inhibitors were selected for combination studies with Compound 2 in relapsed refractory multiple myeloma. Five MM cell lines with acquired or inherent resistance to lenalidomide or pomalidomide were included in the studies (OPM.2-P10, H929-1051, KMS12BM PR, L363, and JJN3). The effect of Compound 2 in combination with these second agents on MM cells were assessed in a 7 day in vitro assay. The MM cells were seeded at densities according to the growth rate of each cell line with the aim of achieving 50-100K cells by Day 7. The assay was performed in a 96-well plate. All MM cell lines were cultured in an incubator at 37° C. with 5% $CO_2$ using the indicated cell culture media containing 1× Penicillin-Streptomycin. The MM cells were primed for 3 days with these second agents at the single agent IC50 value. For compounds that did not achieve an IC50 value, 3 µM (the highest concentration tested) was used. Compound 2 was added to the cells at a dose range of +µM-0.00018 µM, depending on the cell line, for a 8 point dose response curve. The cells were incubated at 37° C. for an additional 4 days. At the end of the 7 day treatment, the MM cells were stained with Annexin V and 7-AAD and analyzed on a flow cytometer. Live MM cells were identified as Annexin V and 7-AAD double negative cells. In these experiments, synergy calculations were performed using the fractional product method (Webb, 1963). A combination was considered synergistic if synergy was present in one or more doses of Compound 2 with these second agents.

Results: The effect of combining Compound 2 with these second agents was assessed in a panel of MM cell lines in a 7 day assay. Compound 2 was tested in combination with azacitidine (DNA methyltransferase inhibitor), tazemetostat and CPI-1205 (EZH2 inhibitors), Compound C (BET inhibitors), and pinometostat (DOT1L inhibitor). Compound 2 in combination with BET inhibitors (Compound C) showed significant synergy in OPM-2.P10 and H929-1051 cells (FIG. 10A and FIG. 10B). Compound 2 in combination with azacitidine showed synergy in 4 of the cell lines tested (FIG. 11A to FIG. 11D). Combination with EZH2 inhibitors was synergistic in all 5 cell lines tested (FIG. 12A to FIG. 12D, FIG. 13A to FIG. 13D, FIG. 14A, and FIG. 14B) with dose dependent effect illustrated in FIG. 14A and FIG. 14B with the KMS12BM PR cells. Synergy was also evident with Compound 2 in combination with pinometostat (FIG. 15A to FIG. 15D).

Conclusions: Compound 2 in combination with the 6 second agents tested showed synergy in at least 2 or more of the cell lines tested. This data suggests that the combination of Compound 2 with these agents maybe a potential treatment paradigm for relapsed refractory MM.

The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating multiple myeloma comprising administering to a patient having multiple myeloma a therapeutically effective amount of a compound in combination with a second active agent, wherein the compound is Compound 1 having the formula

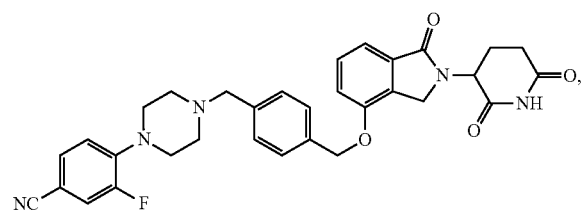

(1)

or an enantiomer, mixture of enantiomers, tautomer, isotopolog, or pharmaceutically acceptable salt thereof; and wherein the second active agent is a Bruton's tyrosine kinase (BTK) inhibitor, and wherein the BTK inhibitor is ibrutinib, or acalabrutinib, or a stereoisomer, mixture of stereoisomers, tautomer, isotopolog, or pharmaceutically acceptable salt thereof.

2. A method of treating multiple myeloma comprising administering to a patient having multiple myeloma a therapeutically effective amount of a compound in combination with a second active agent, wherein the compound is Compound 2 having the formula

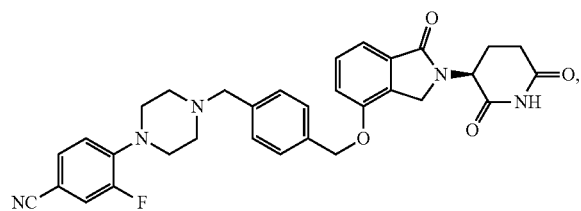

(2)

or a tautomer, isotopolog, or pharmaceutically acceptable salt thereof; and wherein the second active agent is a Bruton's tyrosine kinase (BTK) inhibitor, and wherein the BTK inhibitor is ibrutinib, or acalabrutinib, or a stereoisomer, mixture of stereoisomers, tautomer, isotopolog, or pharmaceutically acceptable salt thereof.

3. The method of claim 2, wherein the compound is Compound 2.

4. The method of claim 2, wherein the multiple myeloma is relapsed, refractory or resistant.

5. The method of claim 4, wherein the multiple myeloma is refractory or resistant to lenalidomide.

6. The method of claim 4, wherein the multiple myeloma is refractory or resistant to pomalidomide.

7. The method of claim 2, wherein the multiple myeloma is newly diagnosed multiple myeloma.

8. The method of claim 2, further comprising administering to the patient an additional active agent.

9. The method of claim 8, wherein the additional active agent is dexamethasone.

10. The method of claim 8, wherein the additional active agent is bortezomib.

11. The method of claim 2, wherein the BTK inhibitor is ibrutinib.

12. The method of claim 3, wherein the BTK inhibitor is ibrutinib.

13. The method of claim 3, wherein the multiple myeloma is relapsed, refractory or resistant.

14. The method of claim 13, wherein the multiple myeloma is refractory or resistant to lenalidomide.

15. The method of claim 13, wherein the multiple myeloma is refractory or resistant to pomalidomide.

16. The method of claim 3, wherein the multiple myeloma is newly diagnosed multiple myeloma.

17. The method of claim 3, further comprising administering to the patient an additional active agent.

18. The method of claim 17, wherein the additional active agent is dexamethasone.

19. The method of claim 17, wherein the additional active agent is bortezomib.

* * * * *